(12) United States Patent
Mukasa et al.

(10) Patent No.: US 8,072,008 B2
(45) Date of Patent: Dec. 6, 2011

(54) BIOSENSOR HAVING ULTRA FINE FIBER

(75) Inventors: Koichi Mukasa, Sapporo (JP); Kazuhisa Sueoka, Sapporo (JP); Seiji Takeda, Sapporo (JP); Satoshi Hattori, Nara (JP); Yoshiki Yamada, Sapporo (JP); Makoto Sawamura, Sapporo (JP); Hiroichi Ozaki, Kayama (JP); Atsushi Ishii, Sapporo (JP); Motonori Nakamura, Sapporo (JP); Hirotaka Hosoi, Sapporo (JP)

(73) Assignees: Mitsumi Electric Co., Ltd., Tokyo (JP); Koichi Mukasa, Hokkaido (JP); Kazuhisa Sueoka, Hokkaido (JP); Kenji Hijikata, Hokkaido (JP); Semicon Craft Technologies, Hokkaido (JP)

( * ) Notice: Subject to any disclaimer, the term of this patent is extended or adjusted under 35 U.S.C. 154(b) by 618 days.

(21) Appl. No.: 11/956,002

(22) Filed: Dec. 13, 2007

(65) Prior Publication Data

US 2008/0283875 A1 Nov. 20, 2008

Related U.S. Application Data

(63) Continuation of application No. PCT/JP2006/311871, filed on Jun. 13, 2006.

(30) Foreign Application Priority Data

| Jun. 14, 2005 | (JP) | 2005-174404 |
| Jun. 14, 2005 | (JP) | 2005-174408 |
| Aug. 17, 2005 | (JP) | 2005-237002 |
| Aug. 31, 2005 | (JP) | 2005-252506 |

(51) Int. Cl.
*G01N 27/403* (2006.01)
*H01L 23/48* (2006.01)
*H01L 23/52* (2006.01)
*H01L 23/40* (2006.01)
*A61B 5/00* (2006.01)
*C12Q 1/00* (2006.01)

(52) U.S. Cl. ........ 257/253; 257/778; 977/746; 977/747; 977/904; 977/920; 977/924; 977/957; 977/958; 977/959; 204/403.13; 204/403.14

(58) Field of Classification Search ................ None
See application file for complete search history.

(56) References Cited

U.S. PATENT DOCUMENTS 5,316,727 A 5/1994 Suzuki et al.
(Continued)

FOREIGN PATENT DOCUMENTS

JP 59-142453 8/1984
(Continued)

OTHER PUBLICATIONS

Takeda et al., "Application of carbon nanotubes for detecting anti-hemagglutinins based on antigen-antibody interaction", Biosensors and Bioelectronics. vol. 21, (2005) pp. 201-205, Available online Oct. 2, 2004.
Lee et al., "Single-electron spectroscopy in a coupled triple-dot system: Role of interdot electron-electron interactions", Physical Review B, vol. 62, No. 12, Sep. 15, 2000, pp. 7735-7738.
(Continued)

*Primary Examiner* — N Drew Richards
*Assistant Examiner* — Michael Jung
(74) *Attorney, Agent, or Firm* — Greenblum & Bernstein, P.L.C.

(57) ABSTRACT

A high-sensitivity field effect transistor using as a channel ultrafine fiber elements such as carbon nanotube, and a biosensor using it. The field effect transistor comprises a substrate, a source electrode and a drain electrode arranged on the substrate, a channel for electrically connecting the source electrode with the drain electrode, and a gate electrode causing polarization due to the movement of free electrons in the substrate. For example, the substrate has a support substrate consisting of semiconductor or metal, a first insulating film formed on a first surface of the support substrate, and a second insulating film formed on a second surface of the support substrate, the source electrode, the drain electrode, and the channel arranged on the first insulating film, the gate electrode disposed on the second insulating film.

2 Claims, 75 Drawing Sheets

U.S. PATENT DOCUMENTS

| | | | |
|---|---|---|---|
| 5,502,396 | A | 3/1996 | Desarzens et al. |
| 5,586,006 | A | 12/1996 | Seyama et al. |
| 7,064,345 | B2 | 6/2006 | Fix et al. |
| 7,157,050 | B2 | 1/2007 | Yazawa et al. |
| 2003/0159945 | A1 | 8/2003 | Miyazaki et al. |
| 2004/0121354 | A1 | 6/2004 | Yazawa et al. |
| 2006/0263255 | A1* | 11/2006 | Han et al. ............ 422/83 |
| 2006/0273356 | A1 | 12/2006 | Matsumoto et al. |
| 2007/0063304 | A1* | 3/2007 | Matsumoto et al. ...... 257/462 |
| 2007/0132043 | A1* | 6/2007 | Bradley et al. ......... 257/414 |

FOREIGN PATENT DOCUMENTS

| | | |
|---|---|---|
| JP | 1-112453 | 7/1989 |
| JP | 2-82152 | 3/1990 |
| JP | 2-082152 | 3/1990 |
| JP | 3-095432 | 4/1991 |
| JP | 3-259739 | 11/1991 |
| JP | 3-296274 | 12/1991 |
| JP | 4-280474 | 10/1992 |
| JP | 4-290473 | 10/1992 |
| JP | 5-243255 | 9/1993 |
| JP | 7-013611 | 2/1995 |
| JP | 7-58276 | 3/1995 |
| JP | 7-167812 | 7/1995 |
| JP | 2002-296229 | 10/2002 |
| JP | 2003-156469 | 5/2003 |
| JP | 2003-215086 | 7/2003 |
| JP | 2004-101253 | 4/2004 |
| JP | 2005-079342 | 3/2005 |
| JP | 2005-79342 | 3/2005 |
| JP | 2005-513802 | 5/2005 |
| WO | 2004/104568 | 12/2004 |
| WO | 2005/022134 * | 3/2005 |

OTHER PUBLICATIONS

Waser, "Nanoelectronics and information Technology—Advanced Electronic Materials and Novel Devices-", Germany, Wiley-VCH Verlag GmbH & Co. KGaA, Apr. 22, 2003, pp. 493.

Matsumoto, "Room-Temperature Single Electron Devices by Scanning Probe Process", Bulletin of the Electrotechnical Laboratory vol. 63, No. 6, 1999, pp. 25-30.

Matsumoto, "Application of Scanning Tunneling/Atomic Force Microscope Nano-Oxidation Process to Room Temperature Operated Single Electron Transistor and Other Devices", Scanning Microscopy, vol. 12, No. 1, 1998, pp. 61-69.

Cheng et al., "Heterodimensional FET With Split Drain", IEEE Electron Device Letters, vol. 25,, No. 11, Nov. 2004, pp. 737-739.

Yahiro et al., "Sinkikozo wo Motsu Yuuki FET no Sakusei to Hyoka (The preparation and characterization of the new structure organic field effect transistor)", Kyoto University Heisei-15 Nanotech Shienjigyo Seika Hokokusho, 2004, pp. 1-2.

Japan Office action, mail date is Dec. 21, 2010.

An English language abstract JP 3-296274, Year: 1991.

An English language abstract JP 2002-296229, Year: 2002.

Koichi Takekasa "Carbon Nanotube o Mochiita Jisedai Bio Sensor" Kagaku Kogyo, vol. 57, No. 1, Jan. 1, 2006, pp. 1-7, accompanied by a partial English language translation.

An English language abstract JP 2-82152, Year: 1990.

An English language abstract JP 2003-215086, Year: 2003.

K. Matsumoto "Application of Carbon Nanotube SET/FET to sensors," Brochure presented at electronic materials study committee, The Institute of Electrical Engineers of Japan, vol. EFM-03, Nos. 35-45, Dec. 19, 2003, pp. 47-50.

H. Kawarada "Ultra Microscopic Diamond Device by Surface Adsorbed Atom Control" presented in "Function, Control of Electrons, Photons, etc." representative of research adopted in fiscal year 1998, accompanied by a partial English language translation.

* cited by examiner

PRIOR ART

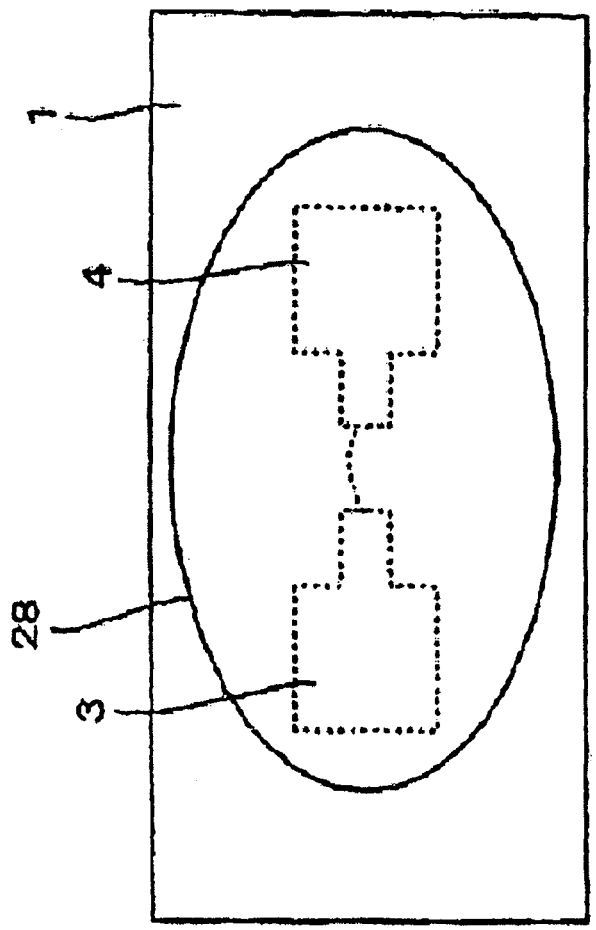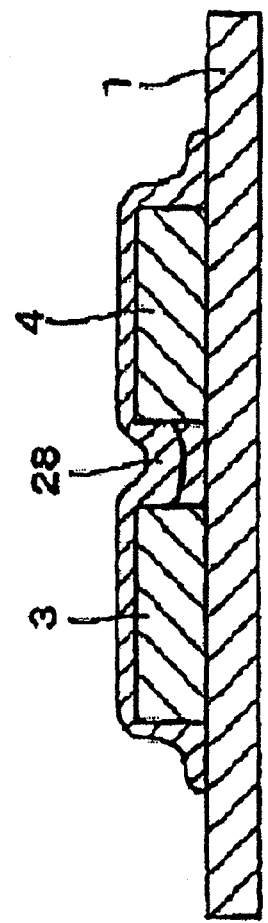
FIG.7A
FIG.7B

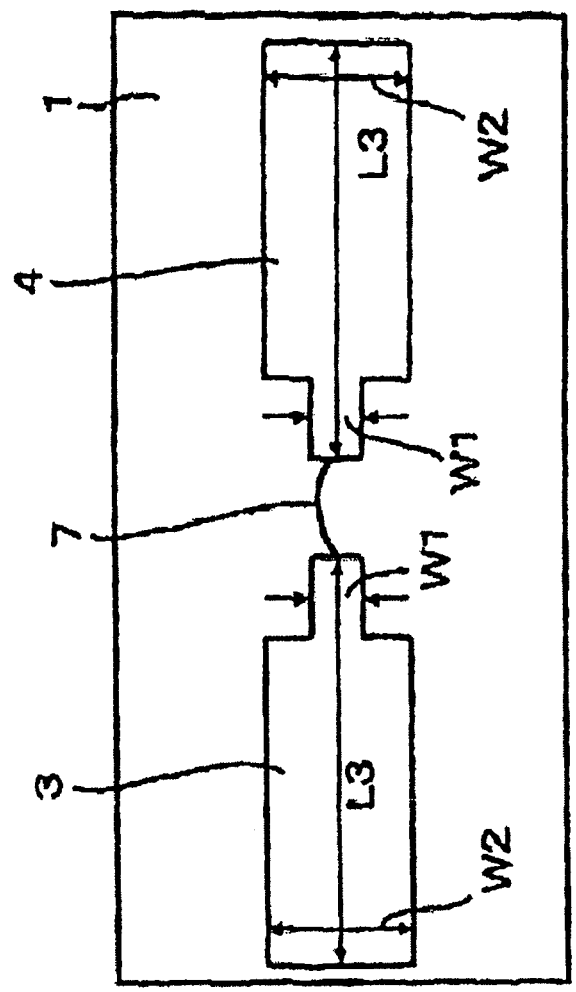
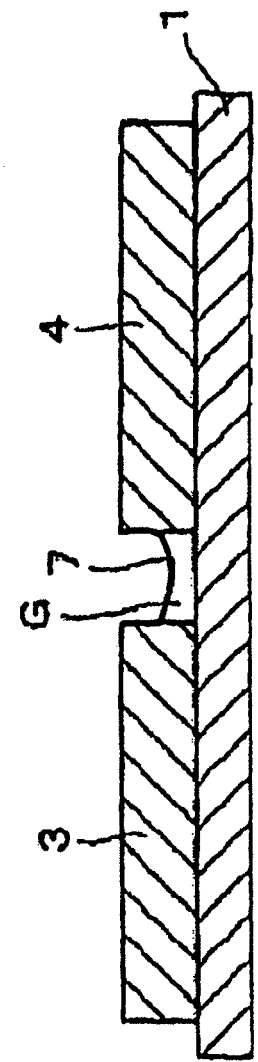
FIG.8A
FIG.8B

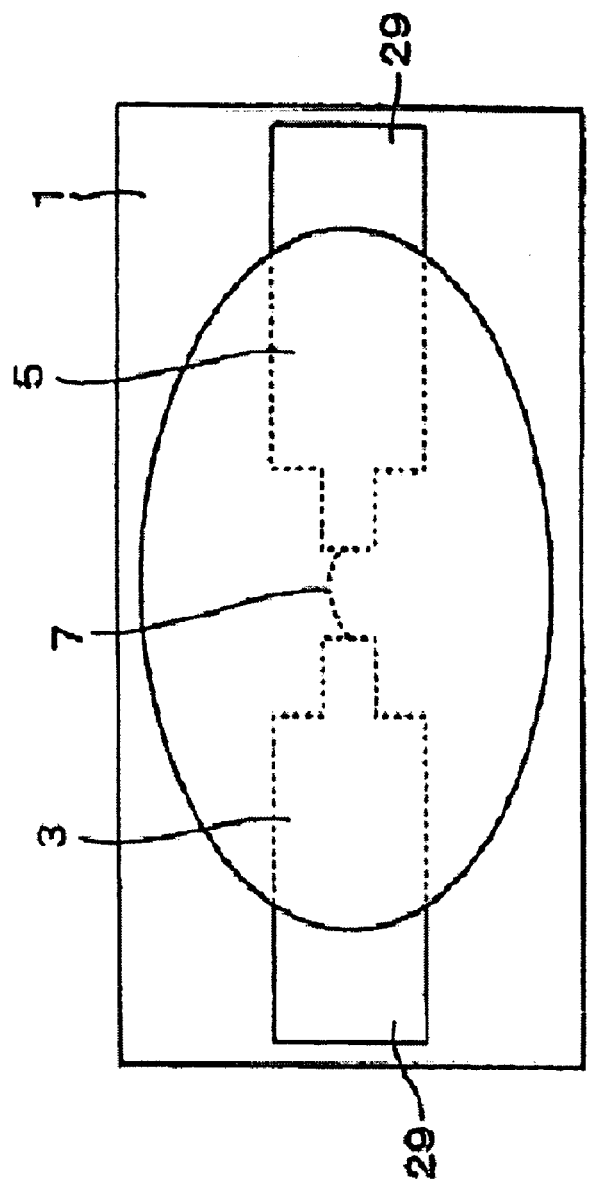
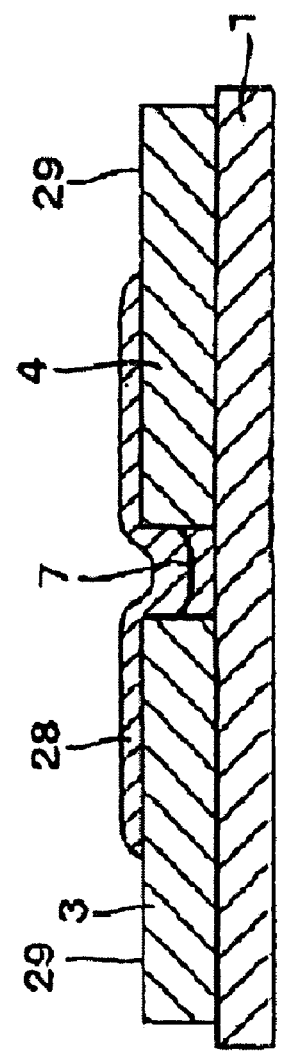
FIG.9A
FIG.9B

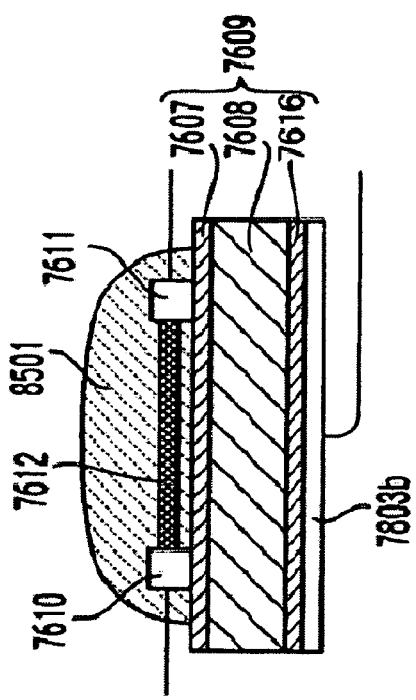
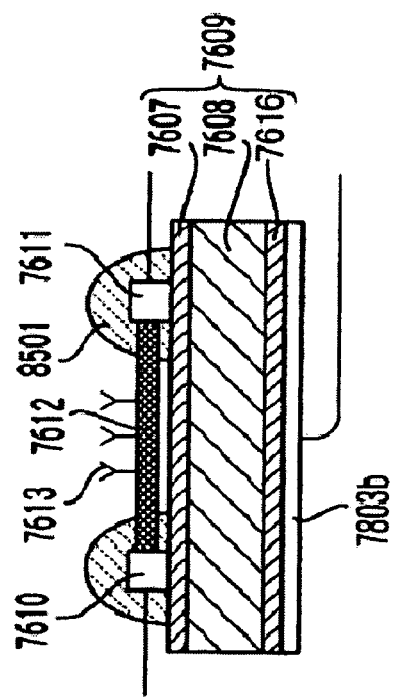
FIG.10A
FIG.10B

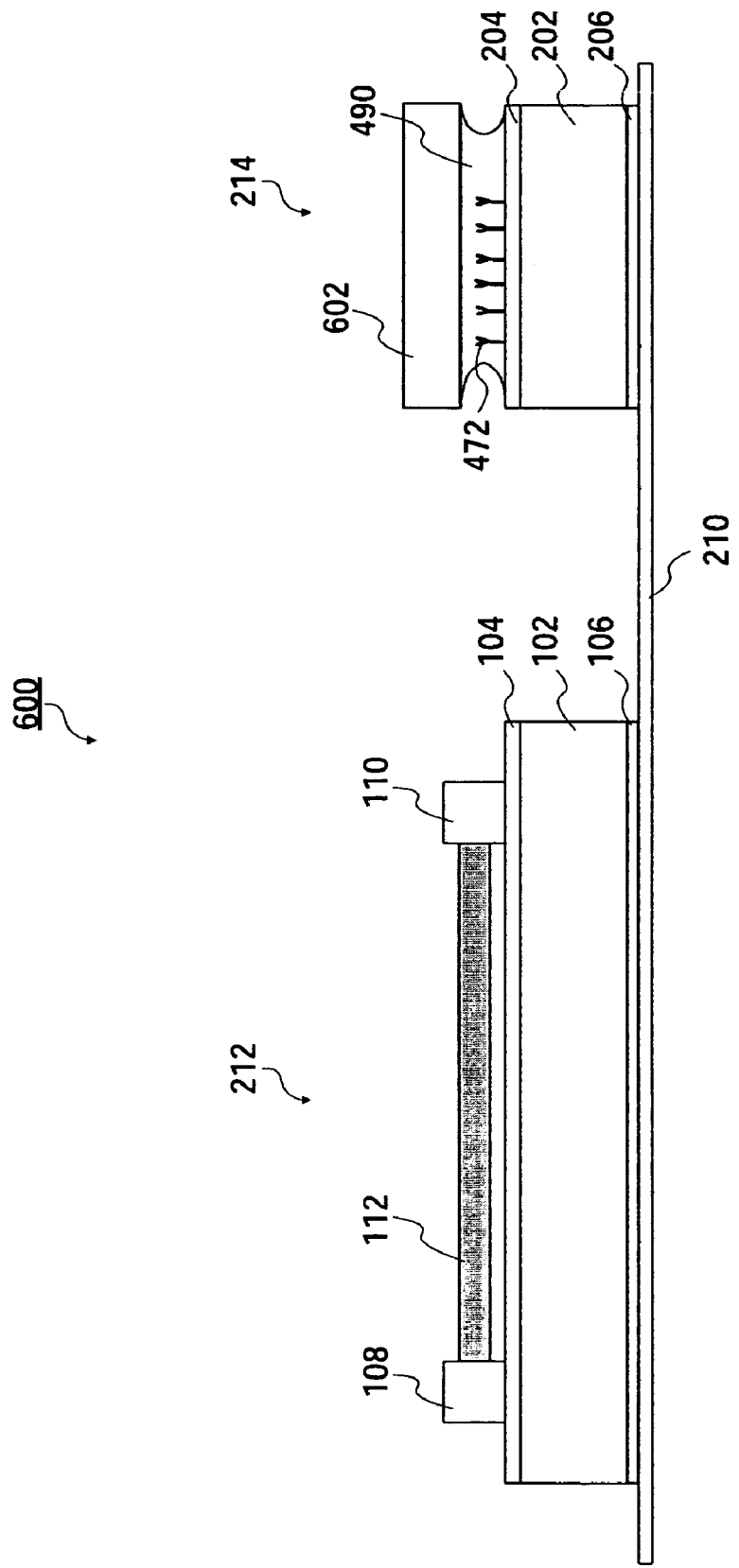

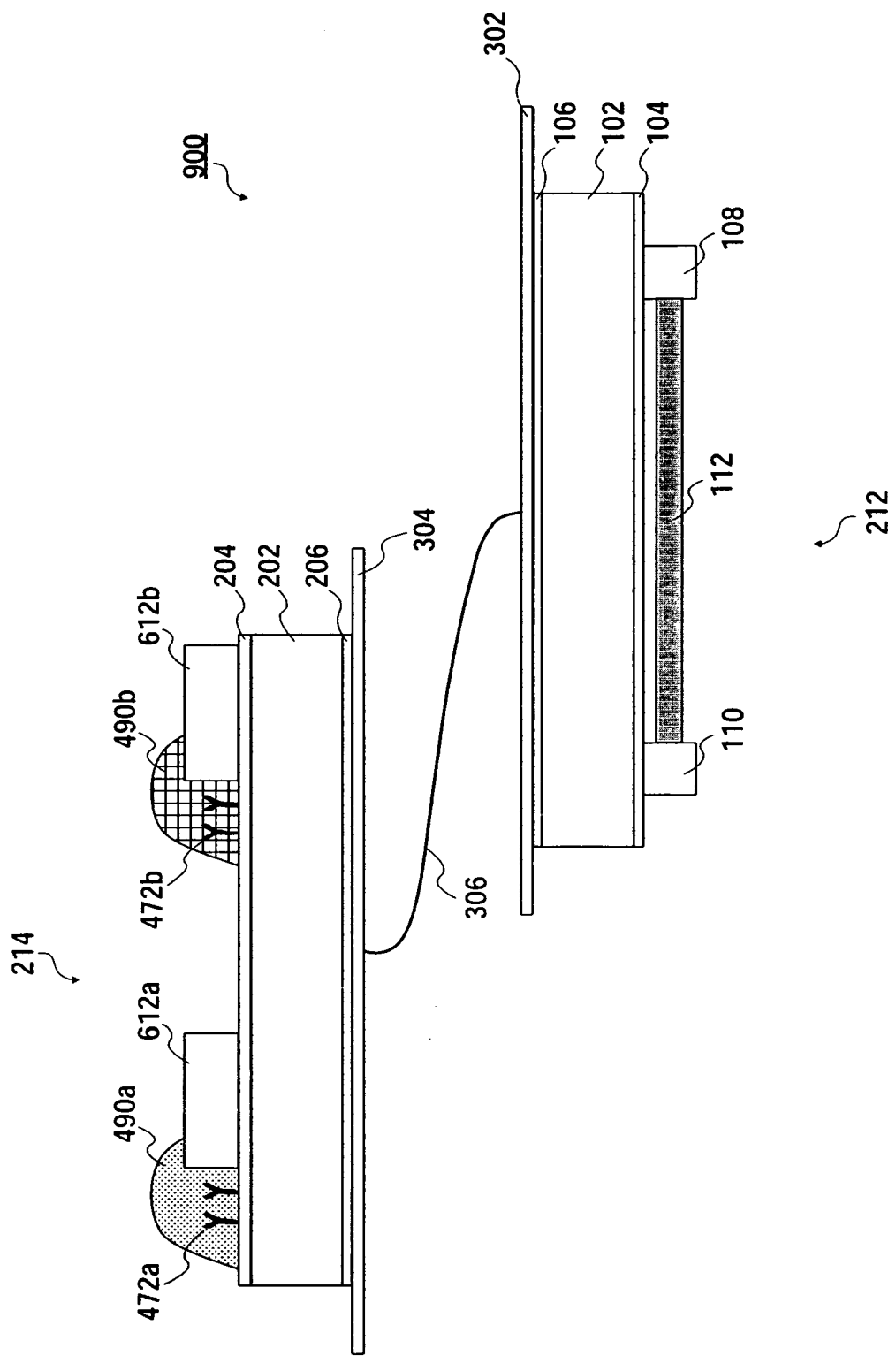

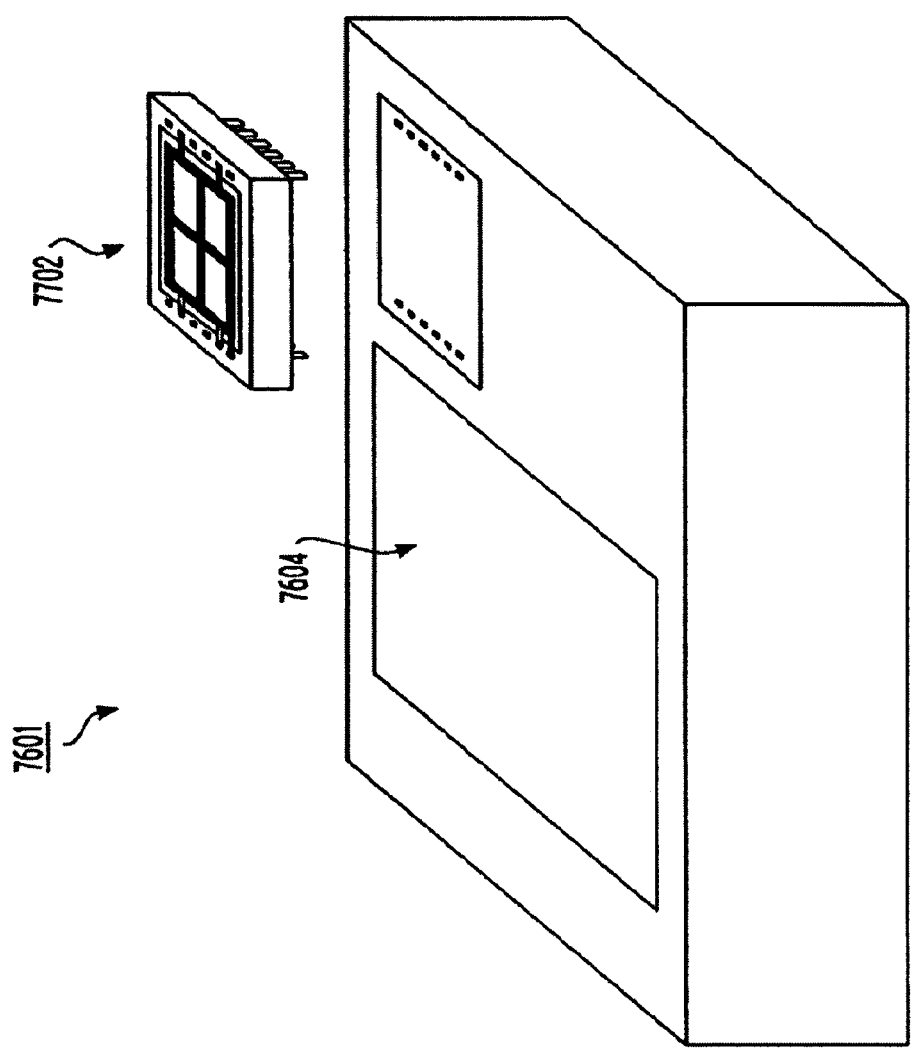

BIOSENSOR HAVING ULTRA FINE FIBER

TECHNICAL FIELD

The present invention relates to a field effect transistor. The present invention further relates to a biosensor including the same, and a method for detecting a detection target substance using the biosensor.

BACKGROUND ART

A field effect transistor (hereafter abbreviated as "FET") is a semiconductor element which includes three terminals of a source electrode, a drain electrode and a gate electrode, wherein electric current flowing a channel connected to the source electrode and the drain electrode is controlled by electric field generated by a voltage impressed to the gate electrode. For example, carbon nanotube field effect transistor (hereafter abbreviated as "CNT-FET"), in which a channel across the source electrode and the drain electrode is composed of carbon nanotube (hereafter abbreviated as "CNT"), is known.

As one example of CNT-FET, those shown in FIG. 1A and FIG. 1B are known (e.g., Non-patent document 1).

In CNT-FET shown in FIG. 1A, source electrode 3 and drain electrode 4, as well as a channel for connecting these electrodes are disposed on insulating film 1 formed on a first plane of substrate 2, and gate electrode 5 electrically connected to silicone substrate 2 is disposed on a second plane. FET with such a configuration is referred to as a back-gate field effect transistor (hereafter abbreviated as "back-gate FET").

With FET shown in FIG. 1B, source electrode 3, drain electrode 4, and gate electrode 5 are disposed on insulating film 1 formed on the first plane of substrate 2. FET of this sort is referred to as, based on arrangement of the gate electrode, side-gate field effect transistor (hereafter abbreviated as "side-gate FET").

Further, developments of sensors utilizing electric characteristics of CNT-FET have been promoted extensively (e.g., Patent Document 1). These sensors utilize the fact that electric characteristics of CNT that serves as a channel change depending on change of state of a molecule recognizing part bound or immobilized to CNT. For example, reaction between the molecule recognizing part and a detection target substance is detected by a change in electric current between source electrode and drain electrode of CNT-FET (hereafter referred to as "source-drain current") or in voltage (hereafter referred to as "source-drain voltage") via changes in electric characteristics of CNT induced by the reaction.

Patent Document 1: WO2004/104568 pamphlet
Non-patent Document 1: K. Matsumoto, "Application of carbon nanotube SET/FET to sensors", Brochure presented at electronic materials study committee, The Institute of Electrical Engineers of Japan, Vol. EFM-03, Nos. 35-45, Dec. 19, 2003, pp. 47-50

DISCLOSURE OF INVENTION

Problems to be Solved by the Invention

Since, with FET, source-drain current is controlled, a gate electrode for changing electric characteristics of a channel needed to be disposed in the vicinity of the channel.

With back-gate FET, the gate electrode can be brought close to the channel by causing the substrate to act as the back-gate electrode across an insulating film only formed on the substrate. Therefore, it was considered that the gate electrode should be electrically contacted with the substrate. In other words, it was considered that field changes close to the channel due to potential changes of the gate electrode, i.e., actions to the source-drain current, or to source-drain voltage should be enhanced as much as possible, by disposing the gate electrode electrically and directly to the substrate having electric conductivity.

Further, with side-gate FET, since source-drain current was controlled by the gate electrode, it was considered that the gate electrode needed to be disposed close to the channel. In other words, it was considered that actions to the source-drain current, or to source-drain voltage should be enhanced as much as possible, by bringing the gate electrode which is disposed on the same plane of the substrate where the source electrode, drain electrode and channel are disposed, close to the channel formed between the source electrode and the drain electrode in the order of nanometer level.

The present inventor attempted to develop a FET based on a new principle (principle of controlling source-drain current) by which, in FET, a source electrode, a drain electrode, and a channel are formed on insulating film(s); a support substrate, on which the insulating film is formed, is composed of materials which causes polarization by movements of free electrons; and a gate electrode is disposed so as to allow polarization by movements of free electrons in the support substrate.

The inventor found that, while investigating improvement of FET performances and application of FET to biosensors, when the gate electrode of FET is disposed on the reverse side of the substrate on which are disposed the source electrode, drain electrode and channel, the gate electrode of FET is capable of controlling source-drain current even if the insulating film is formed on the reverse side of the substrate, and completed the present invention.

Similarly, the present inventor found that, when the gate electrode of FET is disposed on the same surface of the substrate surface on which are disposed the source electrode, drain electrode and the channel, the gate electrode of FET is capable of controlling source-drain current even if being disposed apart to some extent from the source electrode, drain electrode and the channel, and completed the present invention.

Further, the present inventor found that, a gate electrode being disposed on a separate substrate, which is separated from the substrate on which are disposed the source electrode, drain electrode and channel, but is electrically connected thereto, is capable of controlling source-drain current, and completed the present invention.

Means for Solving the Problem

A first aspect of the present invention relates to a field effect transistor (FET) described below.

[1] A field effect transistor which includes a substrate, a source electrode and a drain electrode disposed on the substrate, a channel for electrically connecting the source electrode and drain electrode, a gate electrode for controlling electric current flowing the channel, wherein the channel includes an ultra fine fiber, the gate electrode effects the substrate to cause polarization due to movement of free electrons.

[2] The field effect transistor according to [1], wherein the ultra fine fiber is a carbon nanotube.

[3] The field effect transistor according to [1] or [2] wherein the substrate comprises a support substrate composed of semiconductor or metal, a first insulating film formed on a first plane of the support substrate, and a second insulating film formed on a second plane of the support substrate, wherein the source electrode, drain electrode, and channel are disposed on the first insulating film, the gate electrode is disposed on the second insulating film.

[4] The field effect transistor according to [3], wherein thickness of the second insulating film is 10 nm or more.

[5] The field effect transistor according to [1] or [2], wherein the substrate comprises a support substrate composed of semiconductor or metal, and a first insulating film formed on a first plane of the support substrate, and wherein the source electrode, drain electrode, channel and gate electrode are disposed on the first insulating film, and an interval between the gate electrode and the ultra fine fiber is 10 µm or more.

[6] The field effect transistor according to [5], wherein an interval between the gate electrode and the ultra fine fiber is 100 µm or more.

[7] The field effect transistor according to [1] or [2], further comprising a second substrate electrically connected to the substrate, wherein the substrate comprises a support substrate composed of semiconductor or metal and a first insulating film formed on a first plane of the support substrate, wherein the source electrode, drain electrode, and channel are disposed on the first insulating film, the gate electrode is disposed on a first plane of the second substrate.

[8] The field effect transistor according to [7], wherein the second substrate comprises a support substrate composed of semiconductor or metal, and a second insulating film formed on the first plane of the support substrate, wherein the gate electrode is disposed on the second insulating film.

[9] The field effect transistor according to [7] or [8], wherein a second plane of the substrate and a second plane of the second substrate are electrically connected by a conductive substrate or a conductive member.

The present invention further relates to a biosensor shown below.

[10] A biosensor device equipped with an element section having a field effect transistor in which a detection target substance capturing molecules are bound, wherein the field effect transistor is the field effect transistor according to [1] through [9].

[11] The biosensor device according to [10], wherein the element section is detachable to and from the biosensor device body, wherein the source electrode and drain electrode flow electric current to the channel, when the element section is mounted to the biosensor device body, wherein the gate electrode controls the electric current flowing the channel, when the element section is mounted to the biosensor device body.

[12] A biosensor device having the field effect transistor according to [7] through [9] comprising a biosensor device body which comprises the substrate, source electrode, drain electrode and channel, and an element section which comprises the second substrate, gate electrode and a detection target substance capturing molecule bound to the second substrate or gate electrode, wherein the element section is detachable to and from the biosensor device body, the gate electrode controls electric current flowing the channel, when the element section is mounted to the biosensor device body.

The present invention further relates to a chip shown below.

[13] A chip including the element section detachable to and from the biosensor device body according to [11] or [12].

The present invention further relates to a biosensor device shown below.

[14] The biosensor device according to [10] through [12], further comprising a storage section that stores a calibration curve which shows relationship between concentration of a detection target substance, and source-drain current or gate voltage at predetermined point on I-V characteristics curve or I-Vg characteristics curve, and a concentration determination section that determines concentration of the detection target substance contained in an unknown sample using the calibration curve.

[15] The biosensor device according to [14], wherein the concentration determination section comprises a measurement section that measures source-drain current or gate voltage at a predetermined point on the I-V characteristics curve or I-Vg characteristics curve, for a sample concentration of the detection target substance of which is unknown, and a concentration computation section that obtains concentration of the detection target substance from the calibration curve based on the source-drain current or gate voltage measured.

[16] The biosensor device according to [14] or [15], further comprising a calibration section that obtains a calibration curve using a sample concentration of the detection target substance of which is known.

[17] The biosensor device according to [16], wherein the calibration-section comprises a measurement section that measures source-drain current or gate voltage at a predetermined point on I-V characteristics curve or I-Vg characteristics curve for each of not less than three samples concentration of the detection target substance of which is known and each concentration is different, and a calibration curve computation section that computes a calibration curve from the source-drain current or gate voltage measured, and concentration of the known detection target substance.

Advantageous Effect of the Invention

FET according to the present invention can employ various gate electrode arrangements which could hardly be attained by conventional FETs. Further, FET of the present invention develops excellent electric characteristics. Therefore, by applying FET of the present invention particularly to biosensors, biosensors with higher freedom of structures than conventional ones and with remarkably excellent detection sensitivity can be presented. Further, since the biosensor according to the present invention can be miniaturized, application to outdoor detection which could not be attained by conventional biosensors is possible.

BRIEF DESCRIPTION OF DRAWINGS

FIG. 4 is a view showing one example of separate-gate FET according to the present invention. Reference number 200 denotes separate-gate FET of the present invention, 102 denotes first support substrate, 104 denotes first insulating film, 106 denotes second insulating film, 108 denotes source electrode, 110 denotes drain electrode, 112 denotes ultra fine fiber, 202 denotes second support substrate, 204 denotes third insulating film, 206 denotes fourth insulating film, 208 denotes gate electrode, 210 denotes conductive substrate, 212 denotes ultra fine fiber element section, and 214 denotes gate element section.

Figure 5:
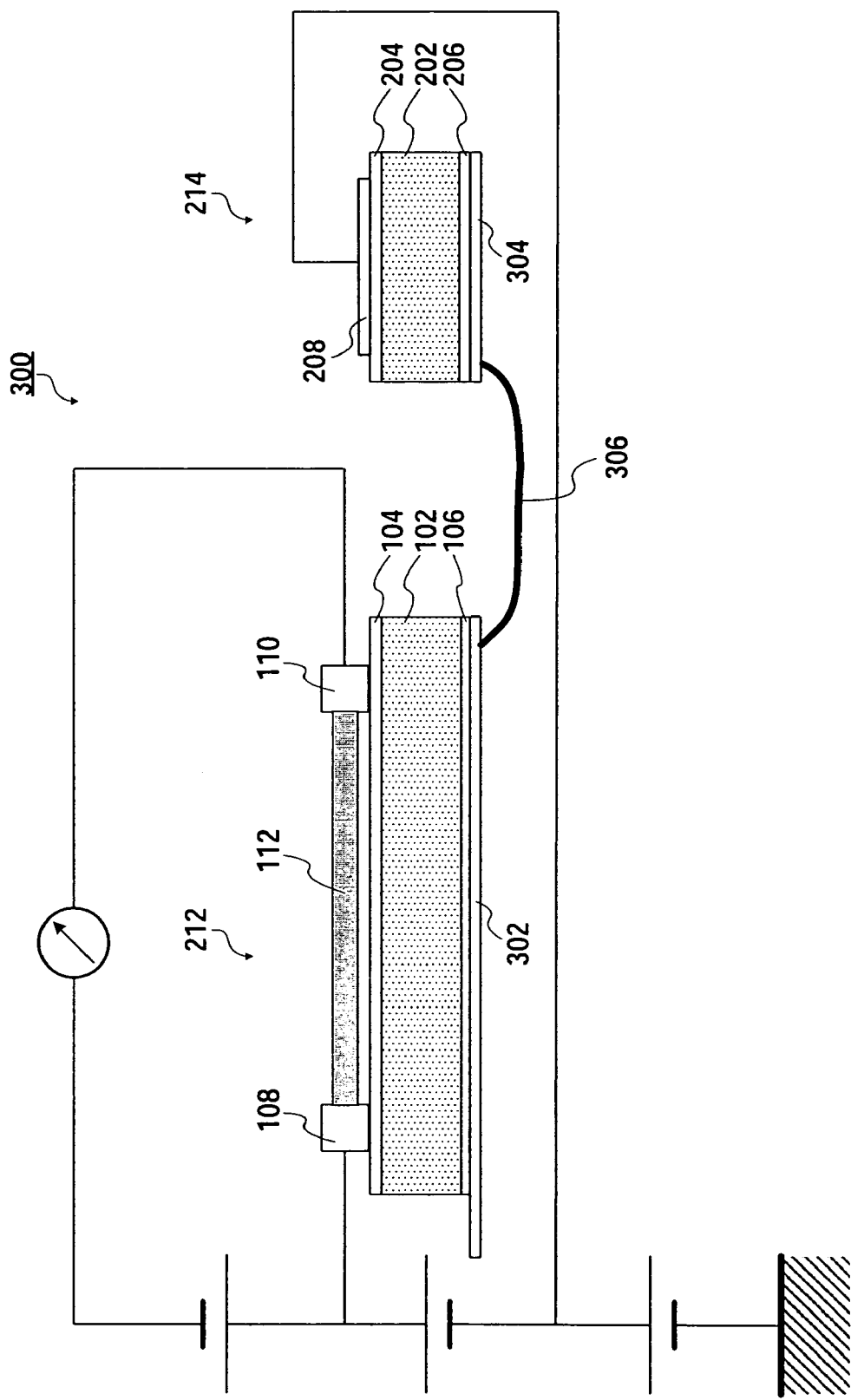

FIG. 5 is a view showing one example of separate-gate FET according to the present invention. Reference number 300 denotes separate-gate FET according to the present invention, 102 denotes first support substrate, 104 denotes first insulating film, 106 denotes second insulating film, 108 denotes source electrode, 110 denotes drain electrode, 112 denotes ultra fine fiber, 202 denotes second support substrate, 204 denotes third insulating film, 206 denotes fourth insulating film, 208 denotes gate electrode, 212 denotes ultra fine fiber element section, 214 denotes gate element section, 302 denotes first conductive substrate, 304 denotes second conductive substrate, and 306 denotes conductive member.

Figure 6A:
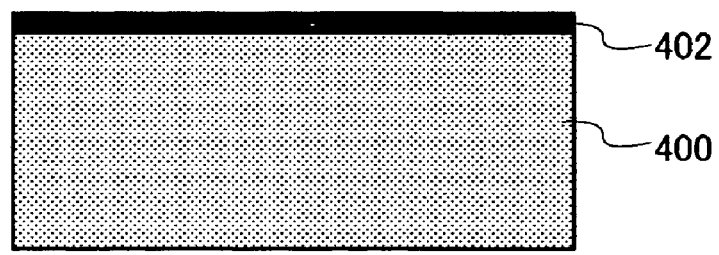
Figure 6B:
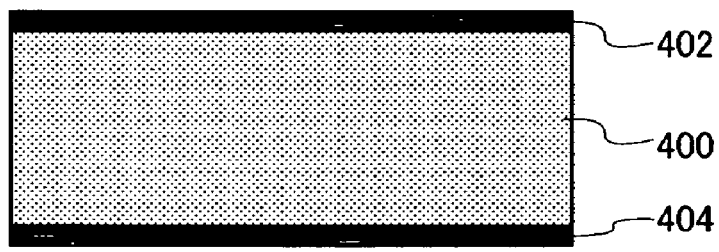

FIGS. 6A and 6B are views showing examples of FET substrate according to the present invention. Reference number 400 denotes support substrate, 402 denotes first insulating film, and 404 denotes second insulating film.

FIG. 7 is a view showing a state after sample solution is added to FET of the present invention, FIG. 7A is a plan view, and FIG. 7B is a cross-sectional view. Reference number 1 denotes first insulating film, 3 denotes source electrode, 4 denotes drain electrode, and 28 denotes sample solution.

FIG. 8 is a view showing one example of FET according to the present invention where a method for preventing influences of the sample solution is provided, FIG. 8A is a plan view, and FIG. 8B is a cross-sectional view. Reference number 1 denotes first insulating film, 3 denotes source electrode, 4 denotes drain electrode, 7 denotes ultra fine fiber, G denotes gap, L3 denotes length of electrode, W1 denotes width of electrode tip, W2 denotes width of a portion to which probe of the electrode is touched.

FIG. 9 is a view showing a state after sample solution is added to FET of the present invention, FIG. 9A is a plan view, and FIG. 9B is a cross-sectional view. Reference number 1 denotes first insulating film, 3 denotes source electrode, 4 denotes drain electrode, 7 denotes ultra fine fiber, 28 denotes sample solution, and 29 denotes a portion which is not covered by sample solution.

FIG. 10A is a view showing FET according to the present invention in which ultra fine fiber is protected by insulating protective film. FIG. 10B is a view showing FET according to the present invention in which connection part between ultra fine fiber and electrode is protected by insulating protective film. Reference number 7608 denotes support substrate, 7607 denotes first insulating film, 7609 denotes substrate, 7610 denotes source electrode, 7611 denotes drain electrode, 7612 denotes ultra fine fiber, 7613 denotes detection target substance capturing molecule, 7616 denotes second insulating film, 7803b denotes gate electrode, and 8501 denotes insulating protective film.

Figure 11:
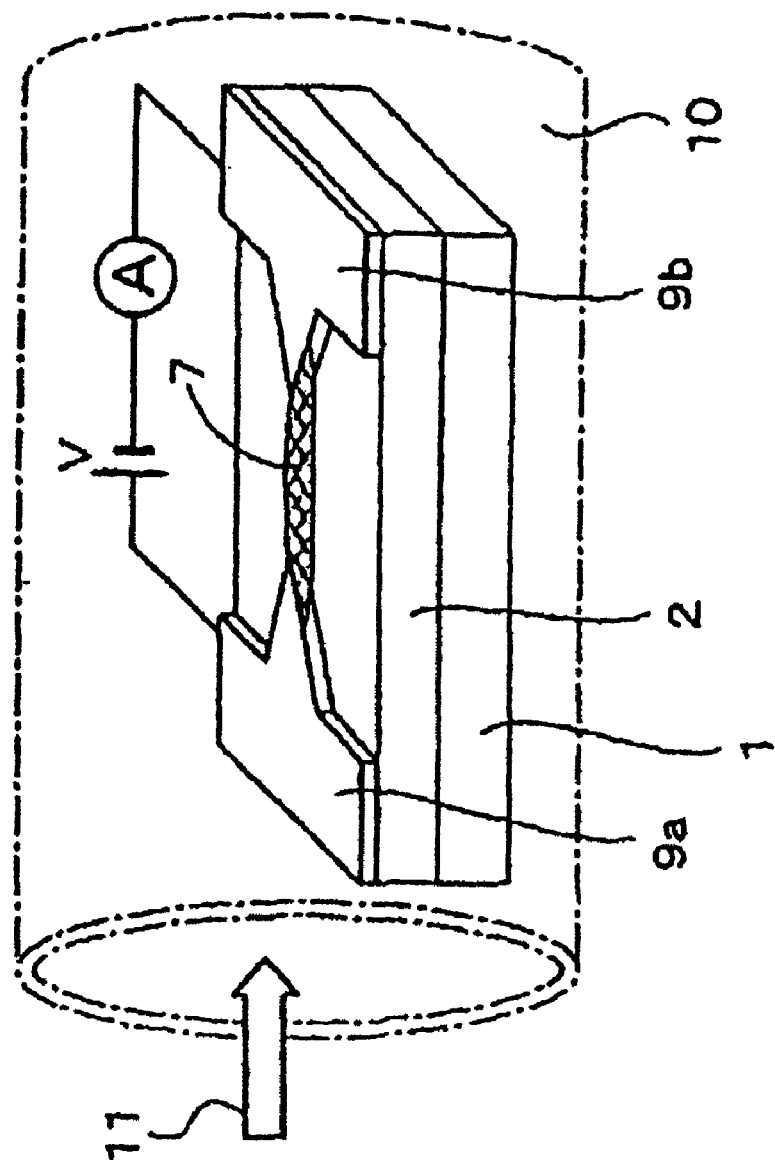

FIG. 11 is a schematic view showing one example of vapor deposition method. Reference number 1 denotes support substrate, 2 denotes first insulating film, 7 denotes CNT, 9a and 9b denote catalyst, 10 denotes reaction chamber, and 11 denotes hydrocarbon gas.

Figure 12:
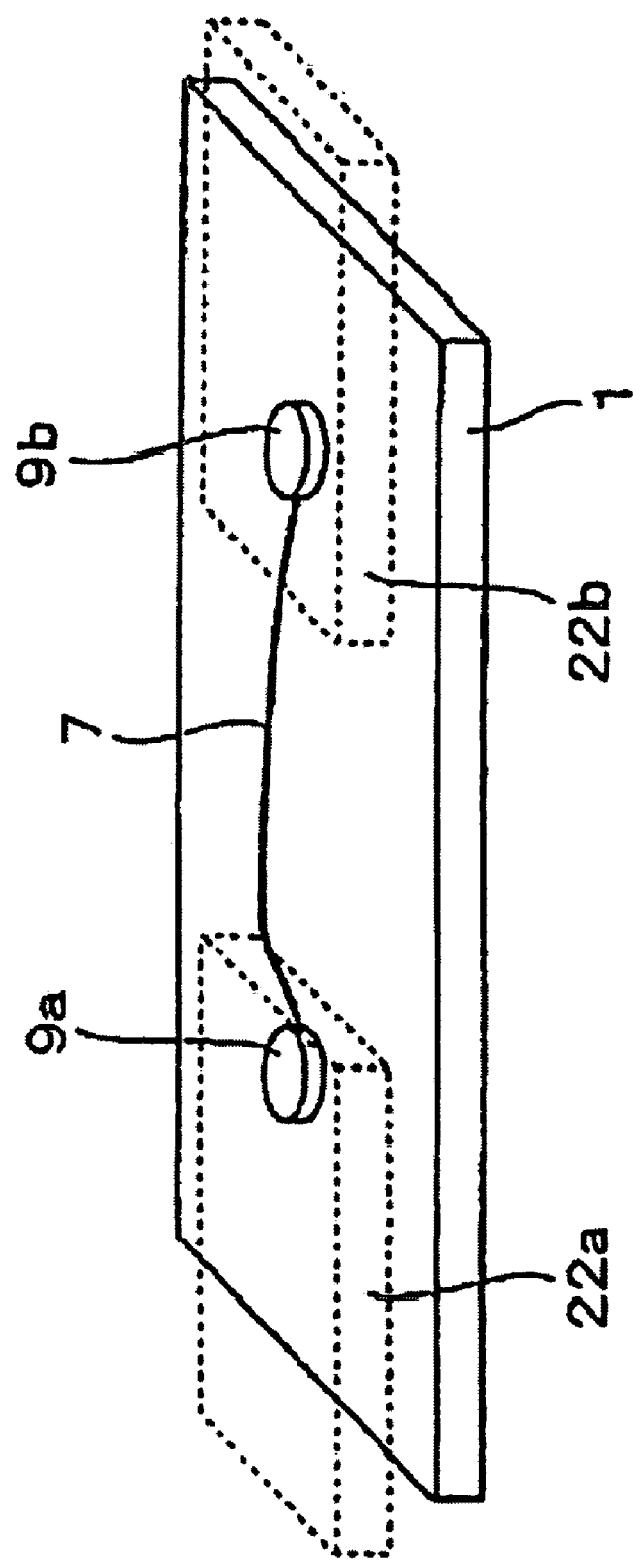

FIG. 12 is a view showing one example for connecting across catalysts by CNT by vapor deposition method. Reference number 1 denotes first insulating film, 7 denotes CNT, 9a and 9b denote catalyst, 22a and 22b denote source electrode and drain electrode to be formed later.

Figure 13:
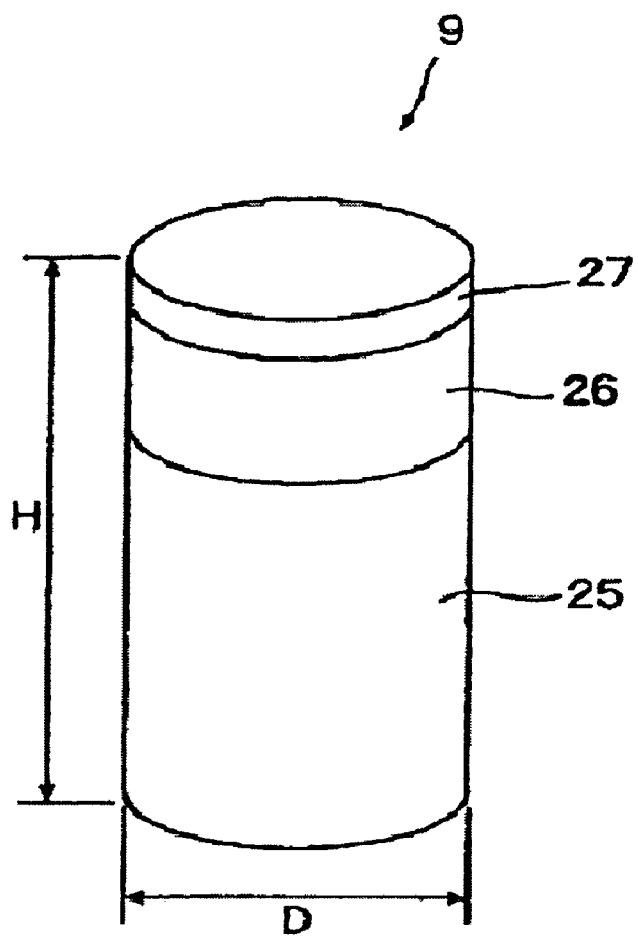

FIG. 13 is a view showing one example of structure of catalyst used in the vapor deposition method. Reference number 9 denotes catalyst, 25 denotes support layer, 26 denotes middle layer, 27 denotes top layer, D denotes diameter, and H denotes total height.

Figure 14:
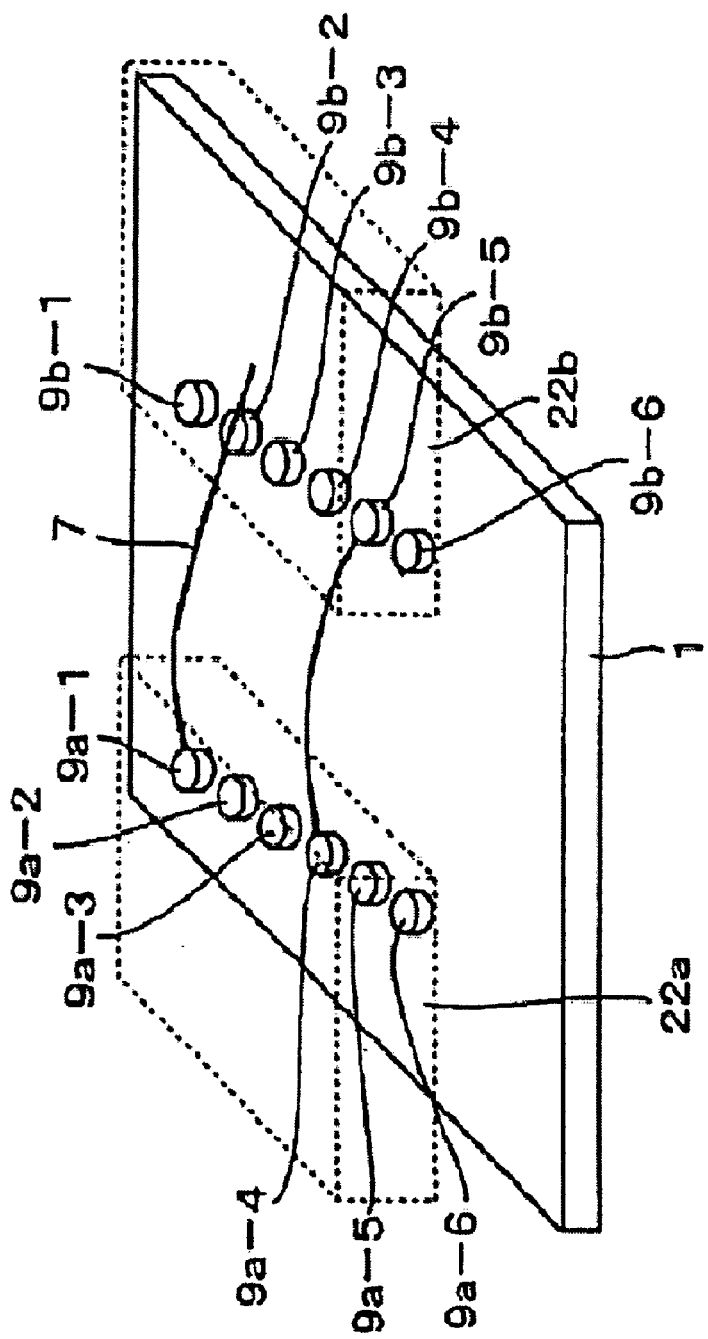

FIG. 14 is a view showing one example for connecting between catalysts by CNT by the vapor deposition method. Reference number 1 denotes first insulating film, 7 denotes CNT, 9a-1 to 9a-6 and 9b-1 to 9b-6 denote catalysts, 22a and 22b denote source electrode and drain electrode to be formed later.

Figure 15:
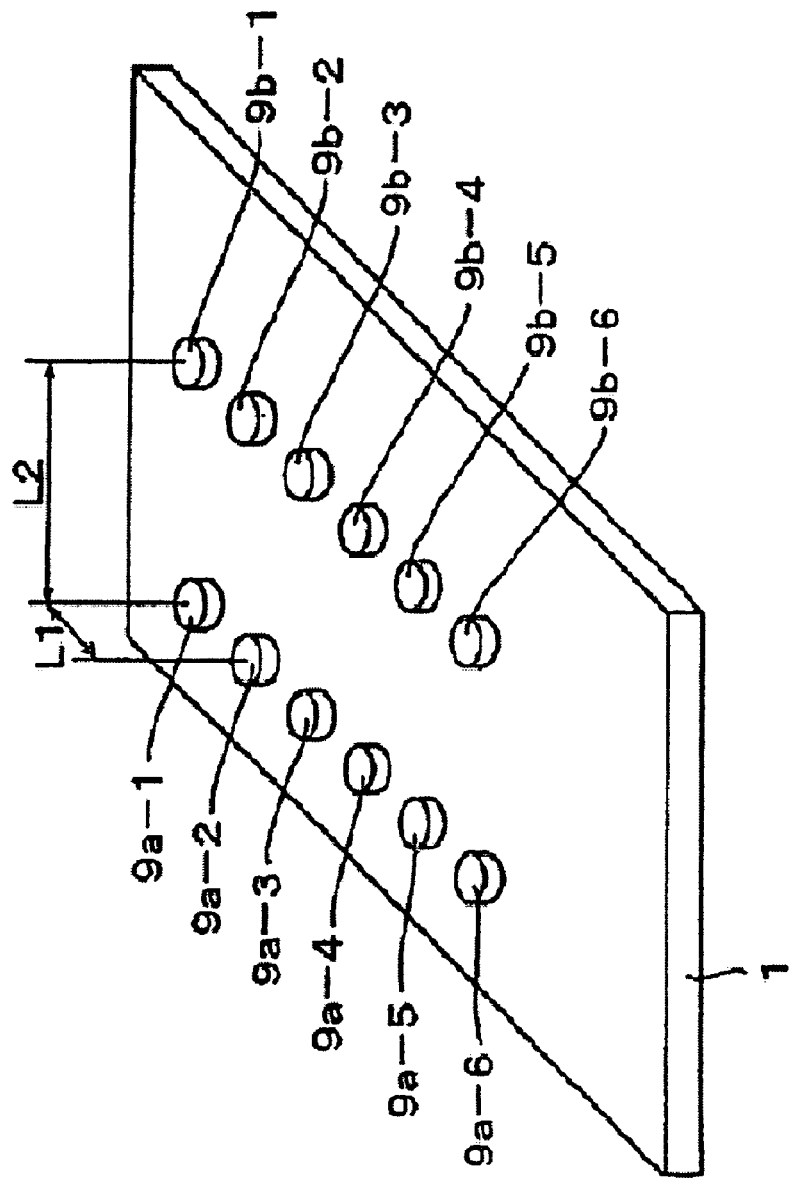

FIG. 15 is a view showing example of arrangement of catalysts. Reference number 1 denotes first insulating film, 9a-1 to 9a-6 and 9b-1 to 9b-6 denote catalysts, L1 denotes distance between catalysts adjoining each other, and L2 denotes distance between catalyst arrays.

Figure 16A:
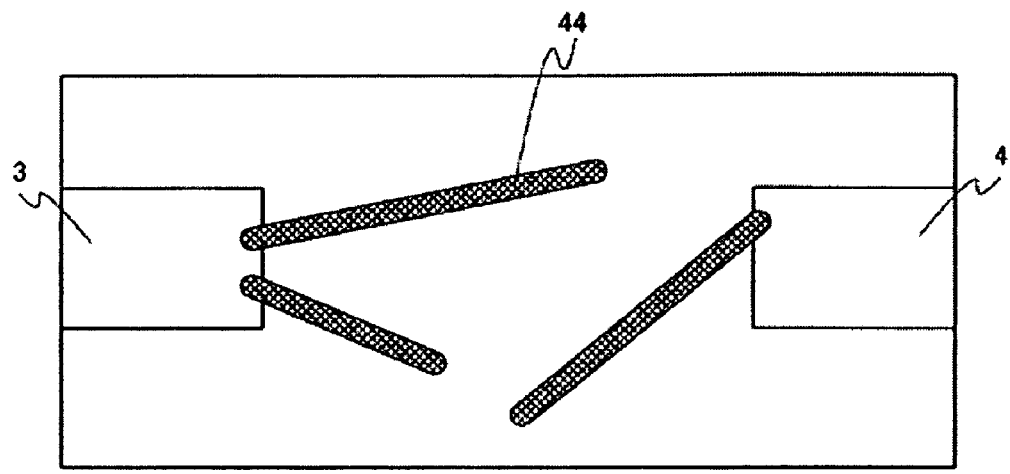
Figure 16B:
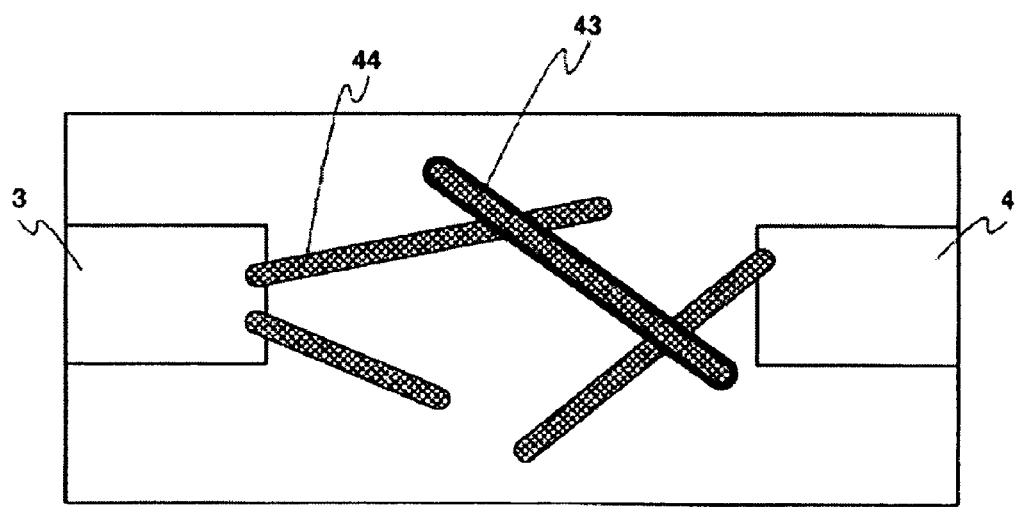

FIG. 16 is a view for explanation of an example of combination of vapor deposition method and improved scattering method. FIG. 16A is a view showing a state where CNT is formed by vapor deposition method, and FIG. 16B is a view showing a state where CNT is further presented by improved scattering method. Reference number 3 denotes source electrode, 4 denotes drain electrode, 44 denotes CNT formed by vapor deposition method, and 43 denotes CNT immobilized by improved scattering method.

Figure 17:
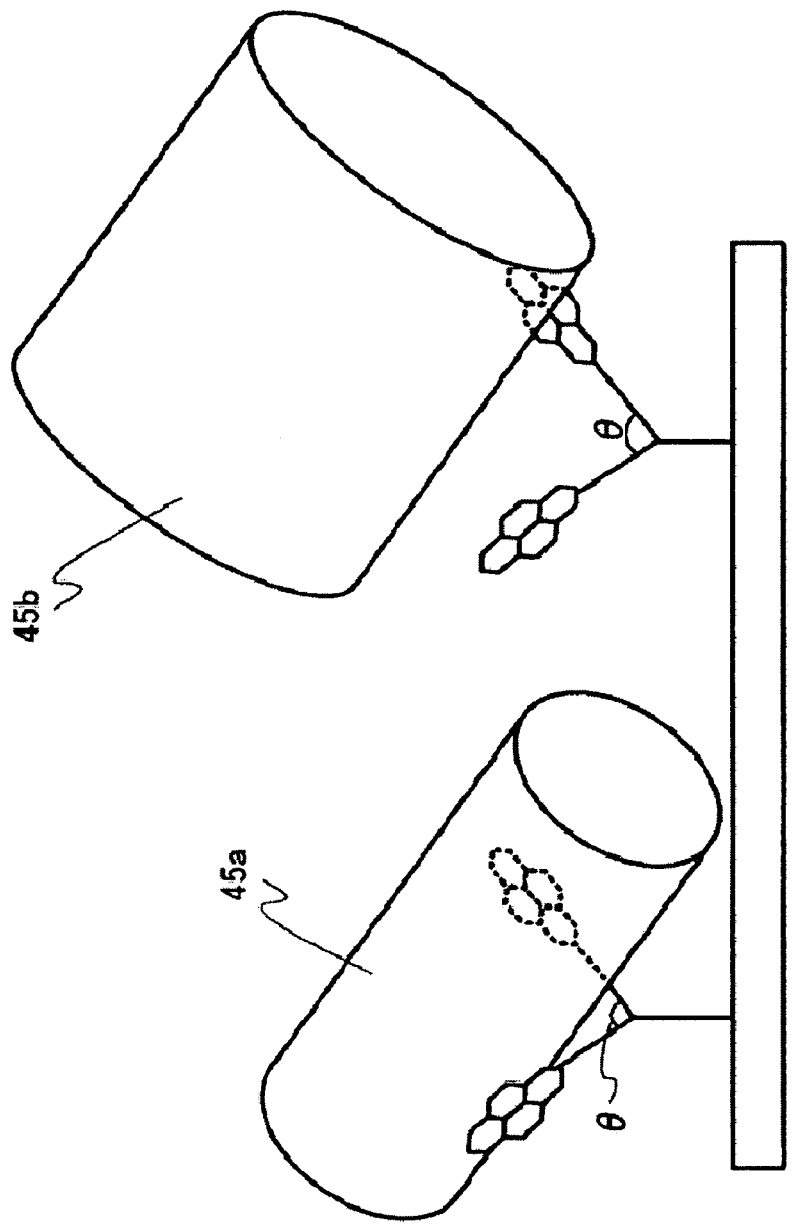
Figure 17A:
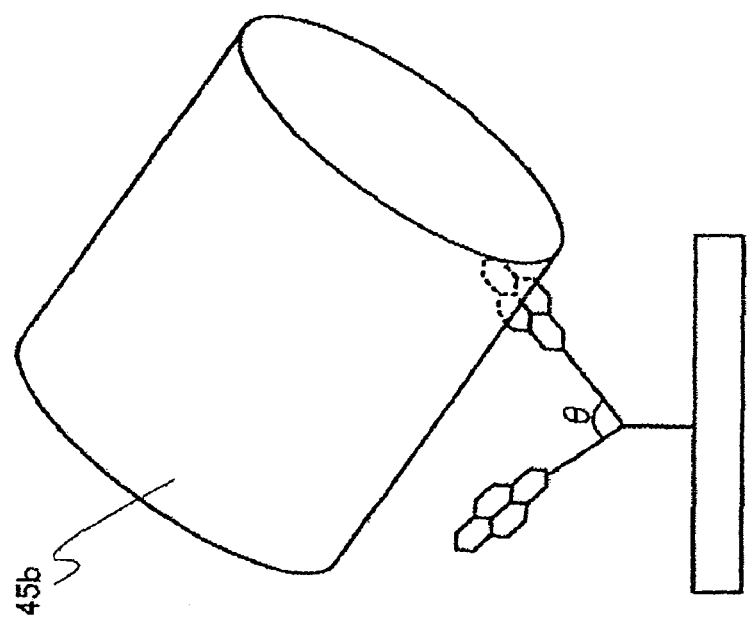
Figure 17B:
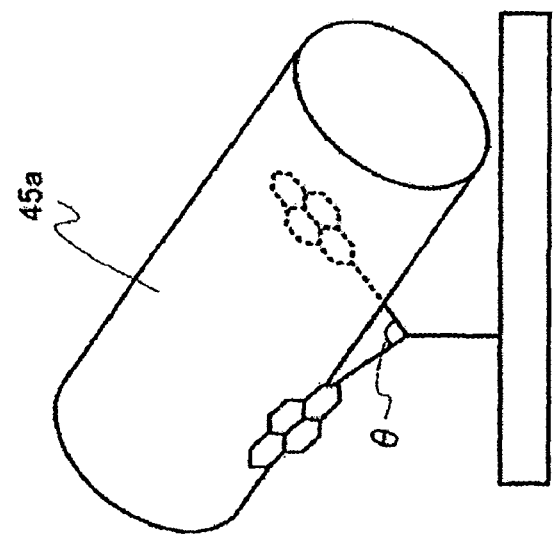

FIG. 17 is a view for explanation of an example where CNT affinity substance selectively immobilizes CNT in the improved scattering method. FIG. 17A is an example where CNT affinity substance immobilizes CNT, and FIG. 17B is an example where CNT is not immobilized. Reference number 45a and 45b denote CNT.

Figure 18:
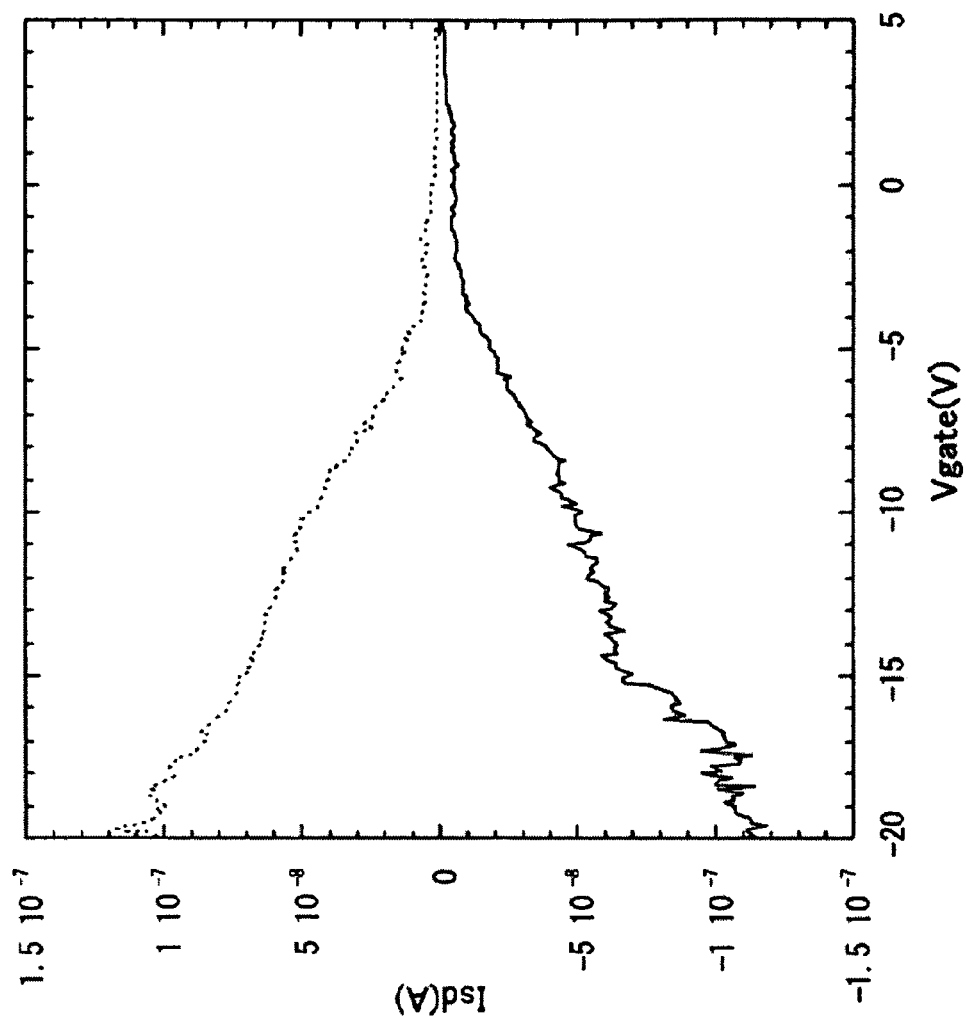

FIG. 18 is a view showing I-Vg characteristics of back-gate FET according to the present invention.

Figure 19:
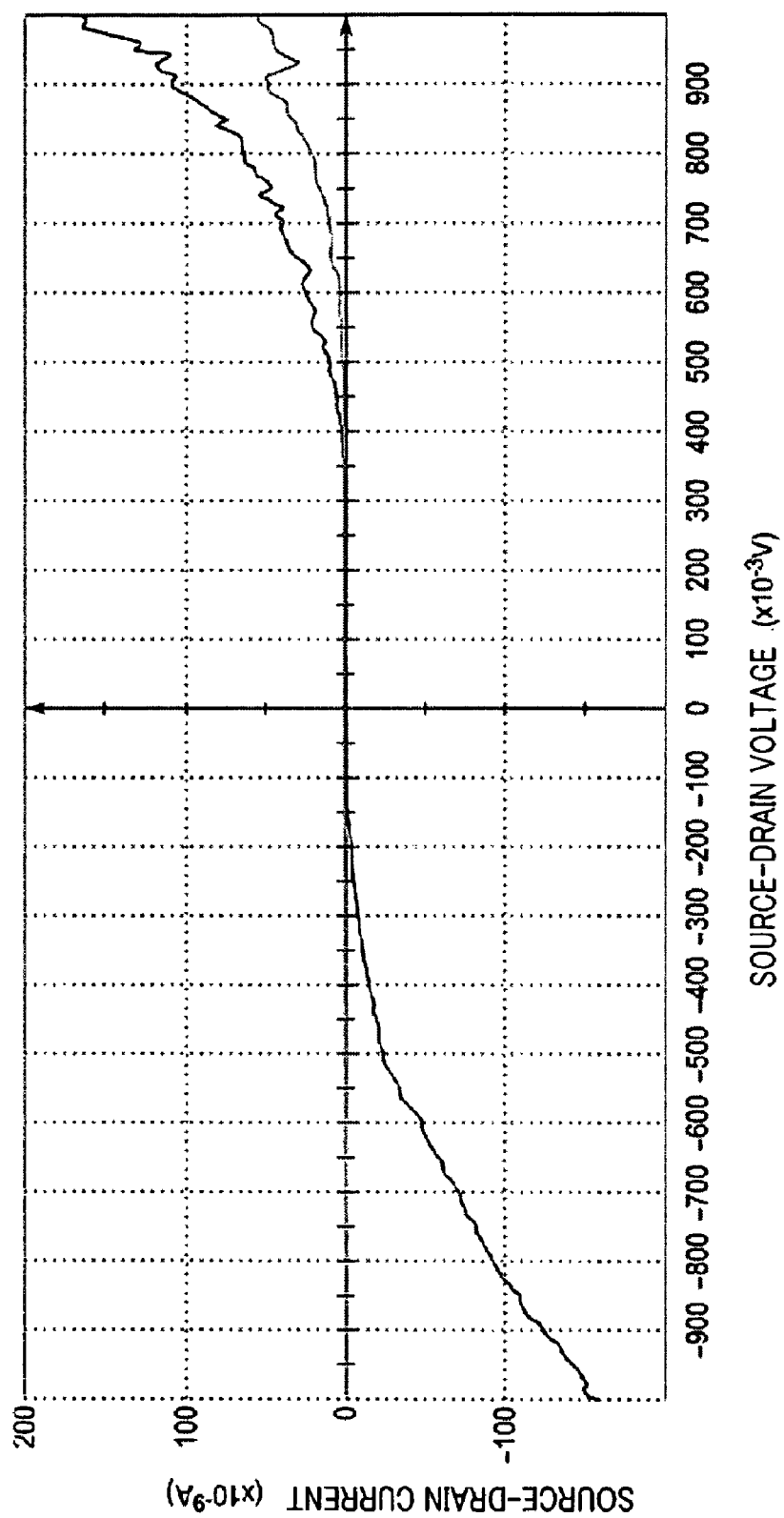

FIG. 19 is a view showing I-V characteristics of back-gate FET according to the present invention.

Figure 20:
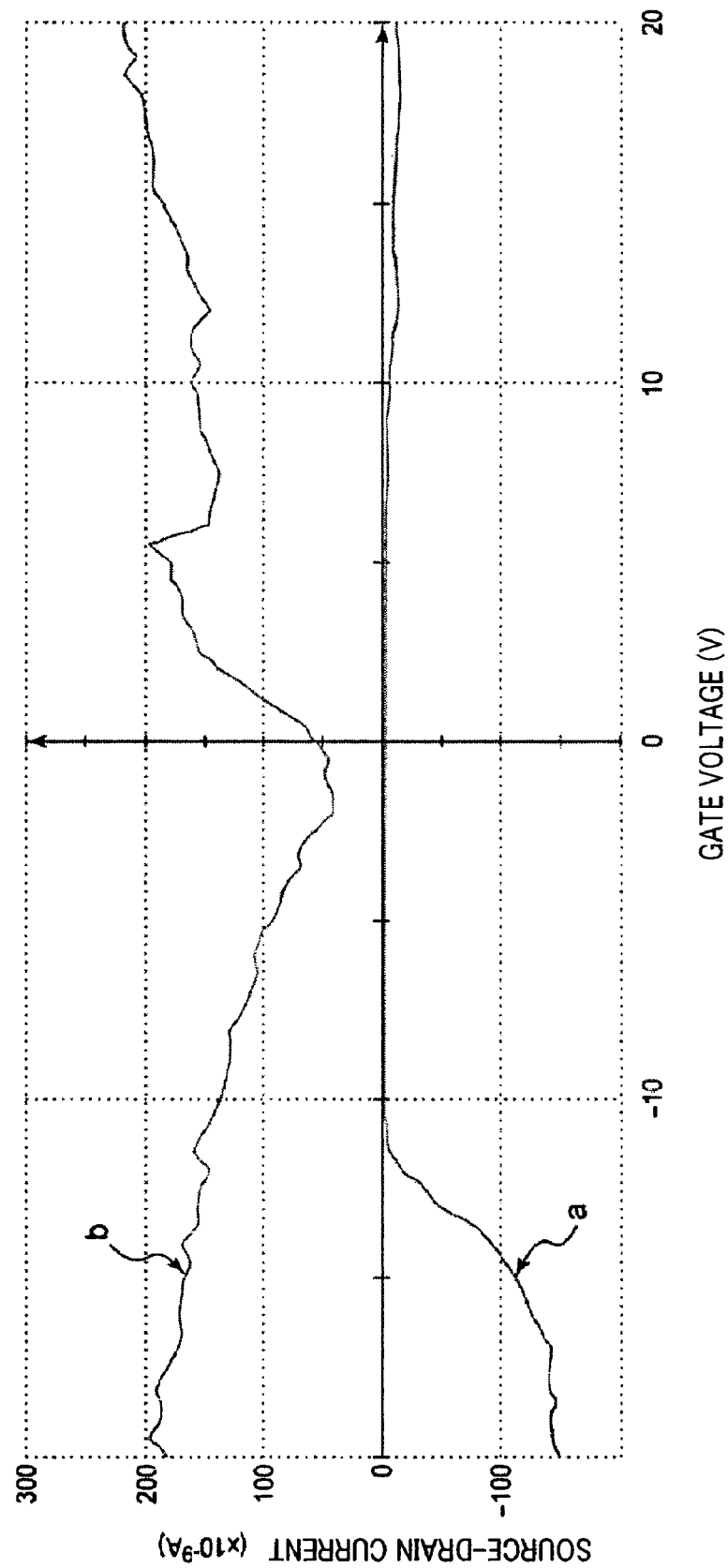

FIG. 20 is a view showing I-Vg characteristics of back-gate FET according to the present invention.

Figure 21:
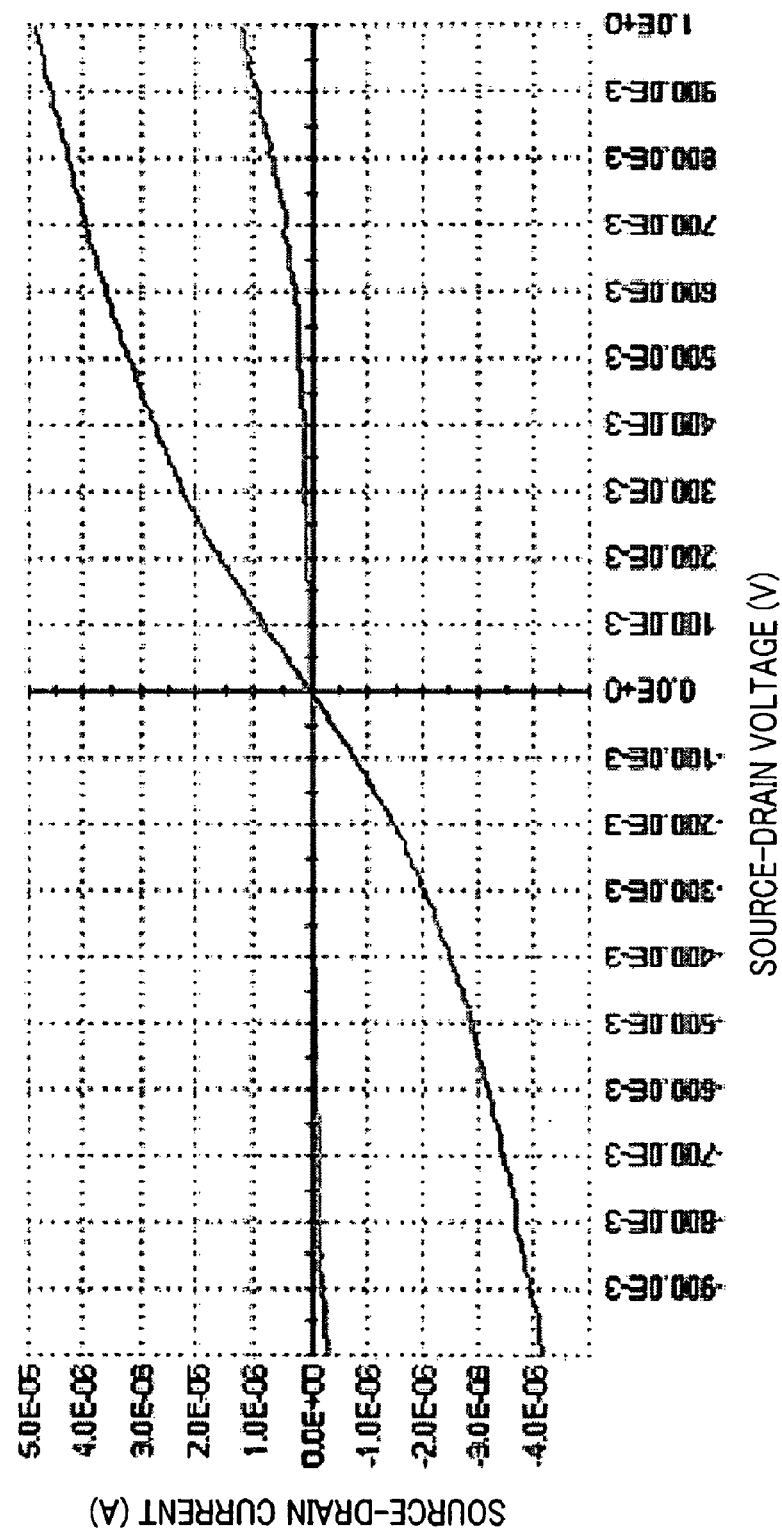

FIG. 21 is a view showing I-V characteristics of side-gate FET according to the present invention.

Figure 22A:
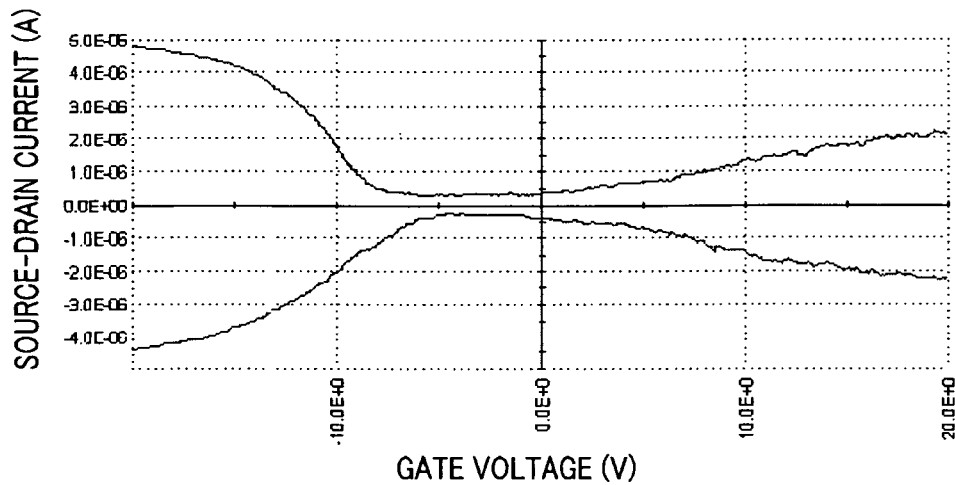
Figure 22B:
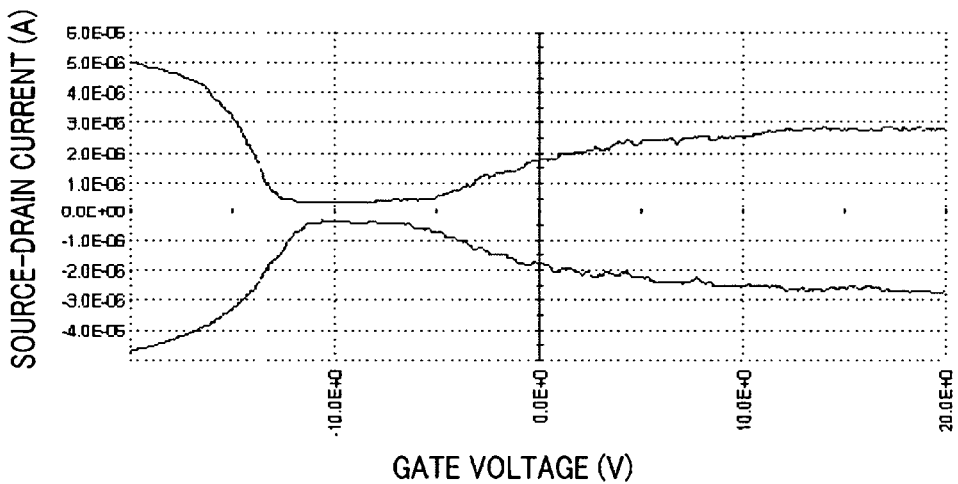
Figure 22C:
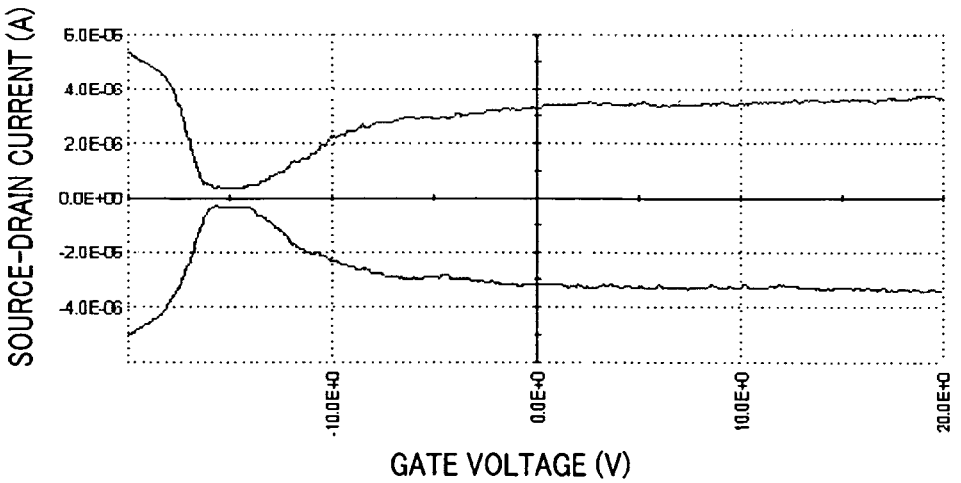

FIG. 22A is a view showing I-Vg characteristics of side-gate FET according to the present invention where interval between gate electrode and CNT is 50 µm, FIG. 22B is a view showing I-Vg characteristics of side-gate FET according to the present invention where interval between gate electrode and CNT is 1 cm, FIG. 22C is a view showing I-Vg characteristics of back-gate FET according to the present invention.

Figure 23:
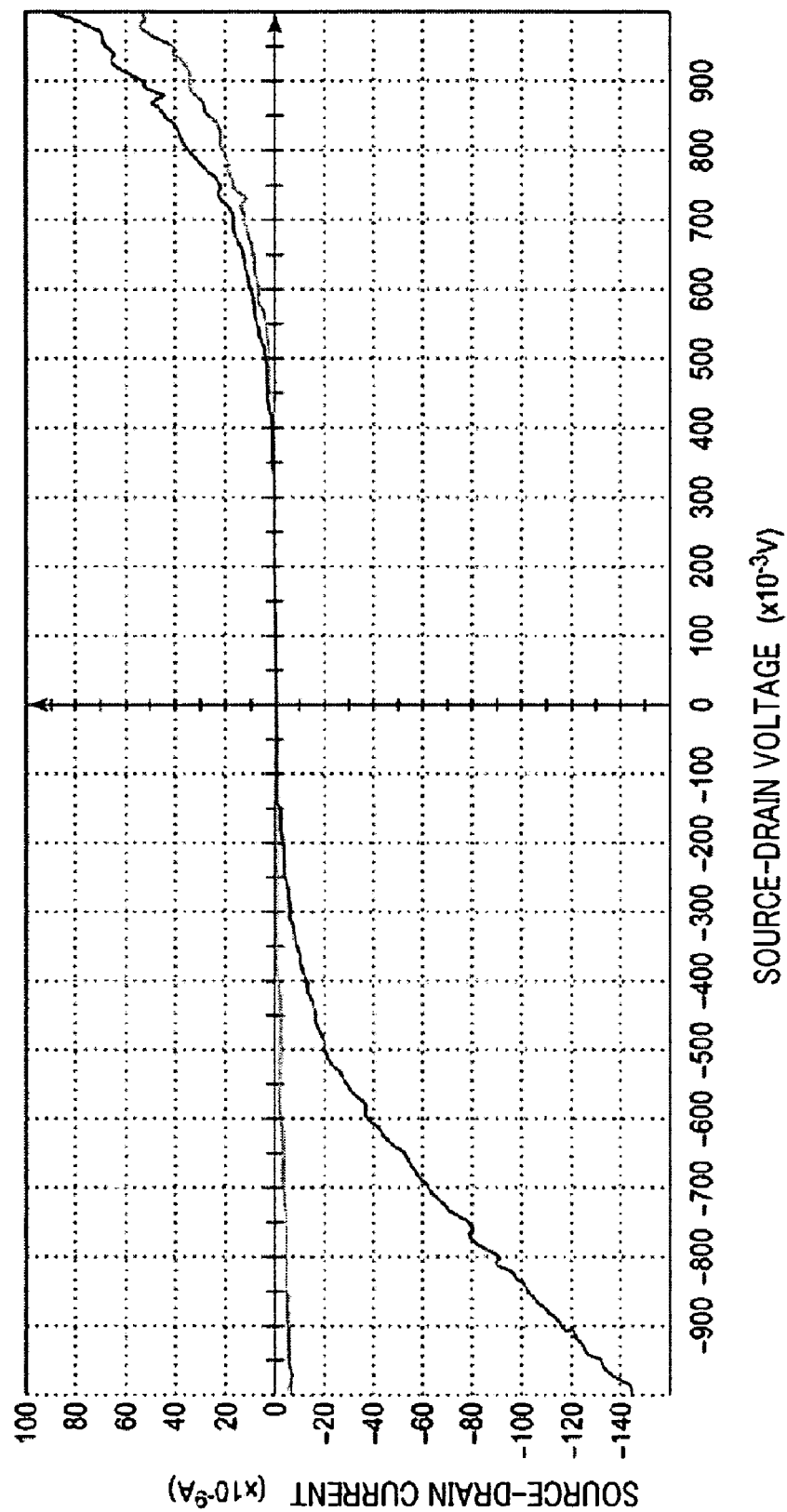

FIG. 23 is a view showing I-V characteristics of separate-gate FET according to the present invention for a case where interval between ultra fine fiber element section and gate element section is 3 mm.

Figure 24:
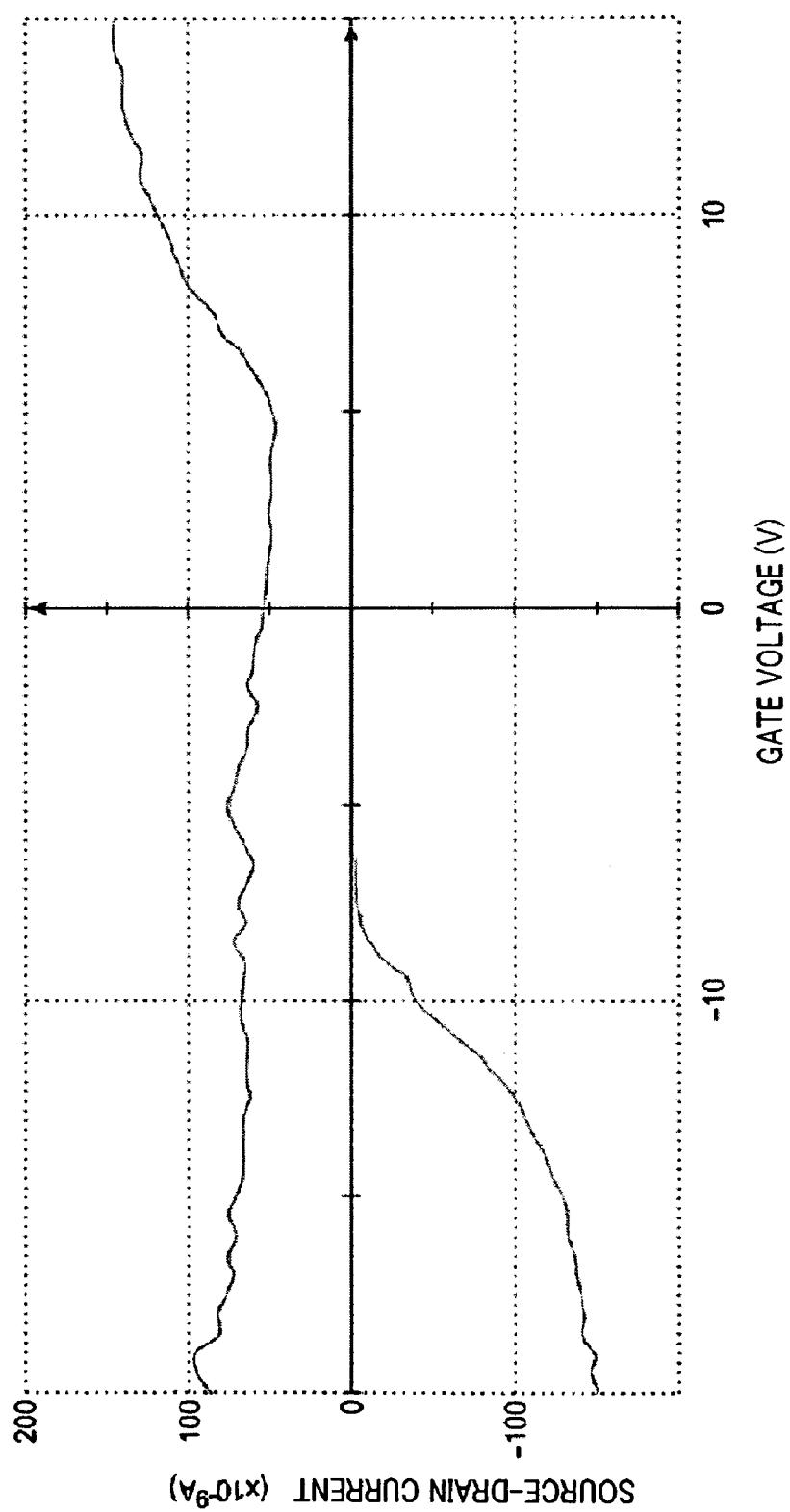

FIG. 24 is a view showing I-Vg characteristics of separate-gate FET according to the present invention for a case where interval between ultra fine fiber element section and gate element section is 3 mm.

Figure 25:
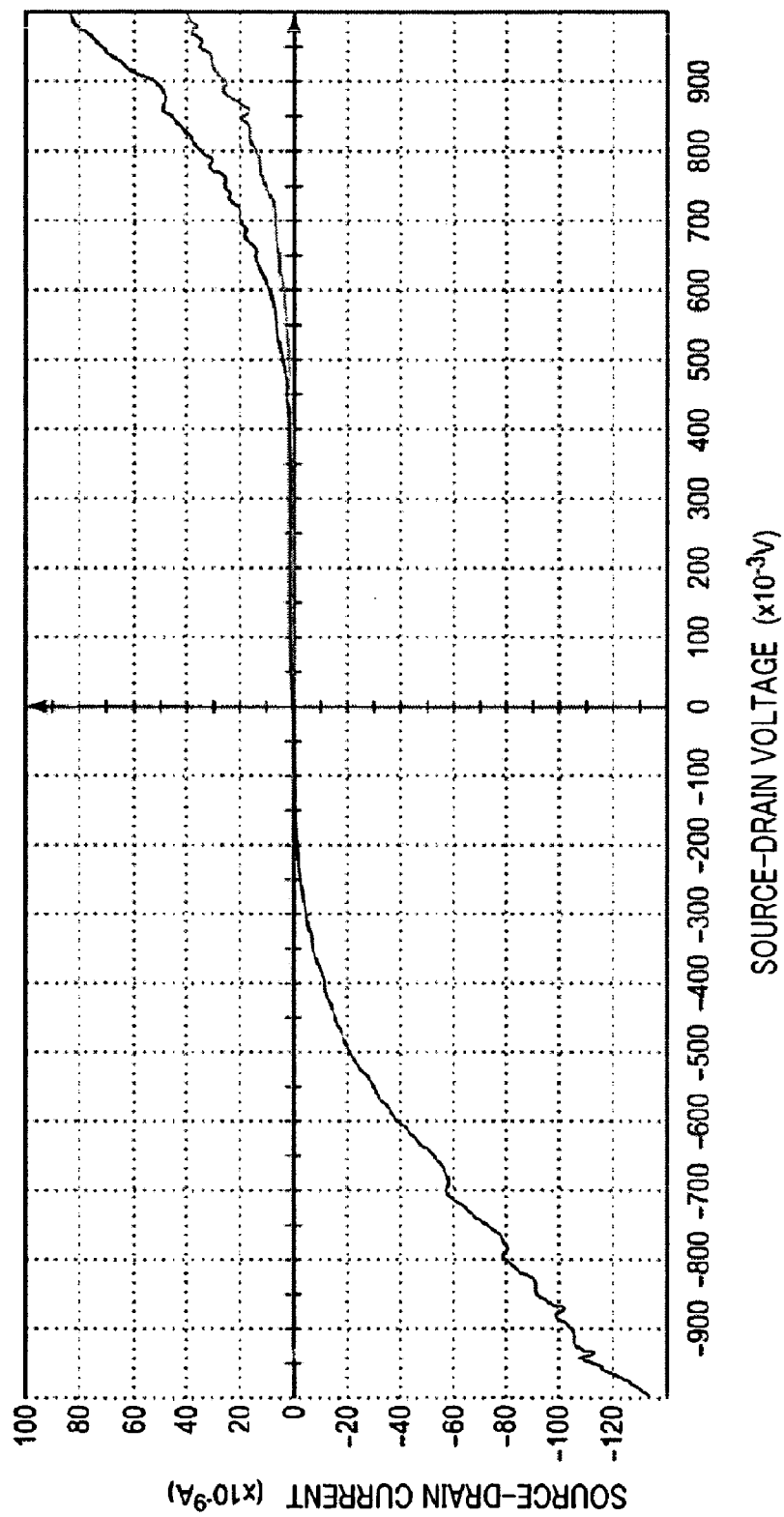

FIG. 25 is a view showing I-V characteristics of separate-gate FET according to the present invention for a case where interval between ultra fine fiber element section and gate element section is 10 mm.

Figure 26:
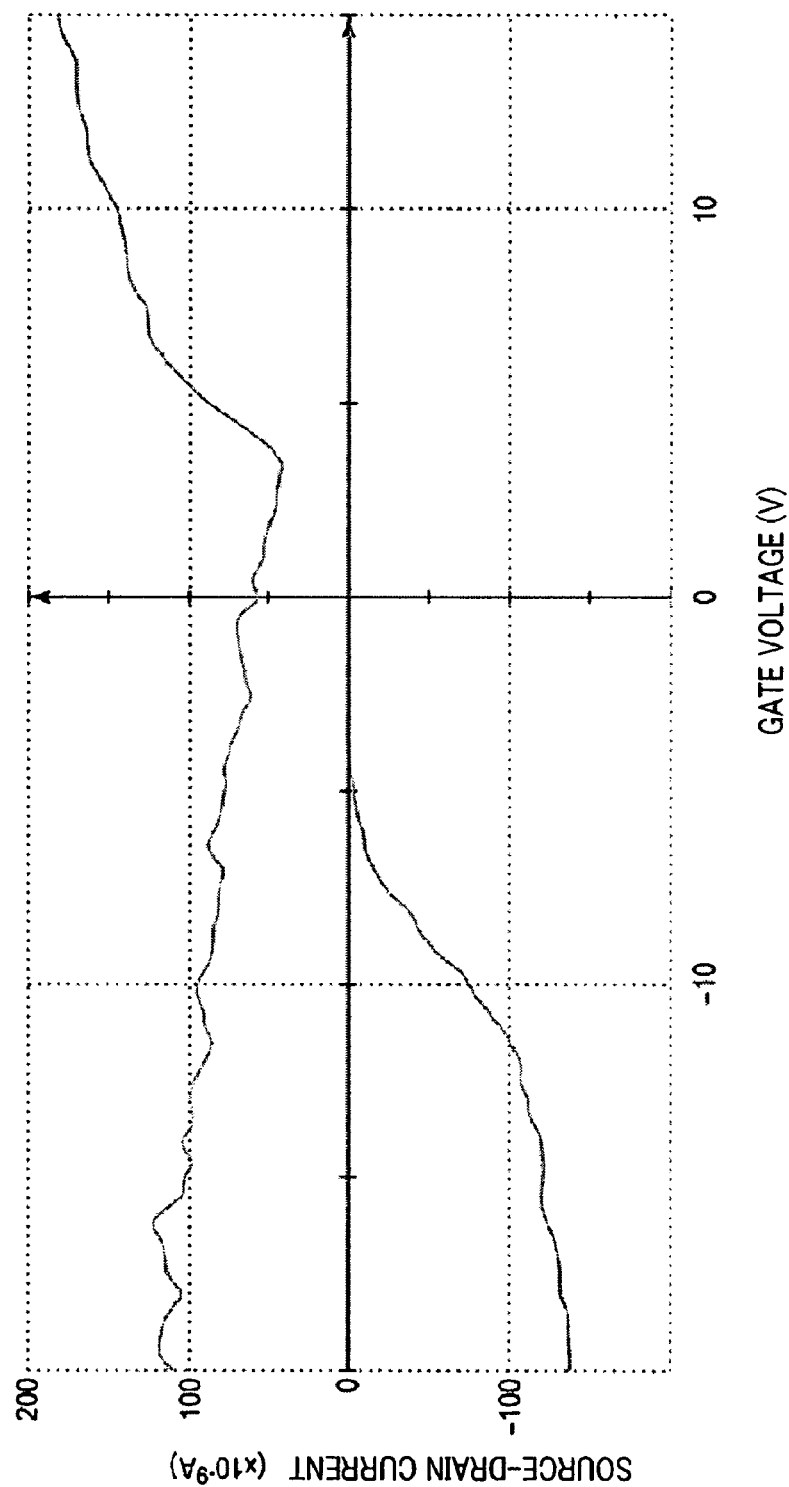

FIG. 26 is a view showing I-Vg characteristics of separate-gate FET according to the present invention for a case where interval between ultra fine fiber element section and gate element section is 10 mm.

Figure 27:
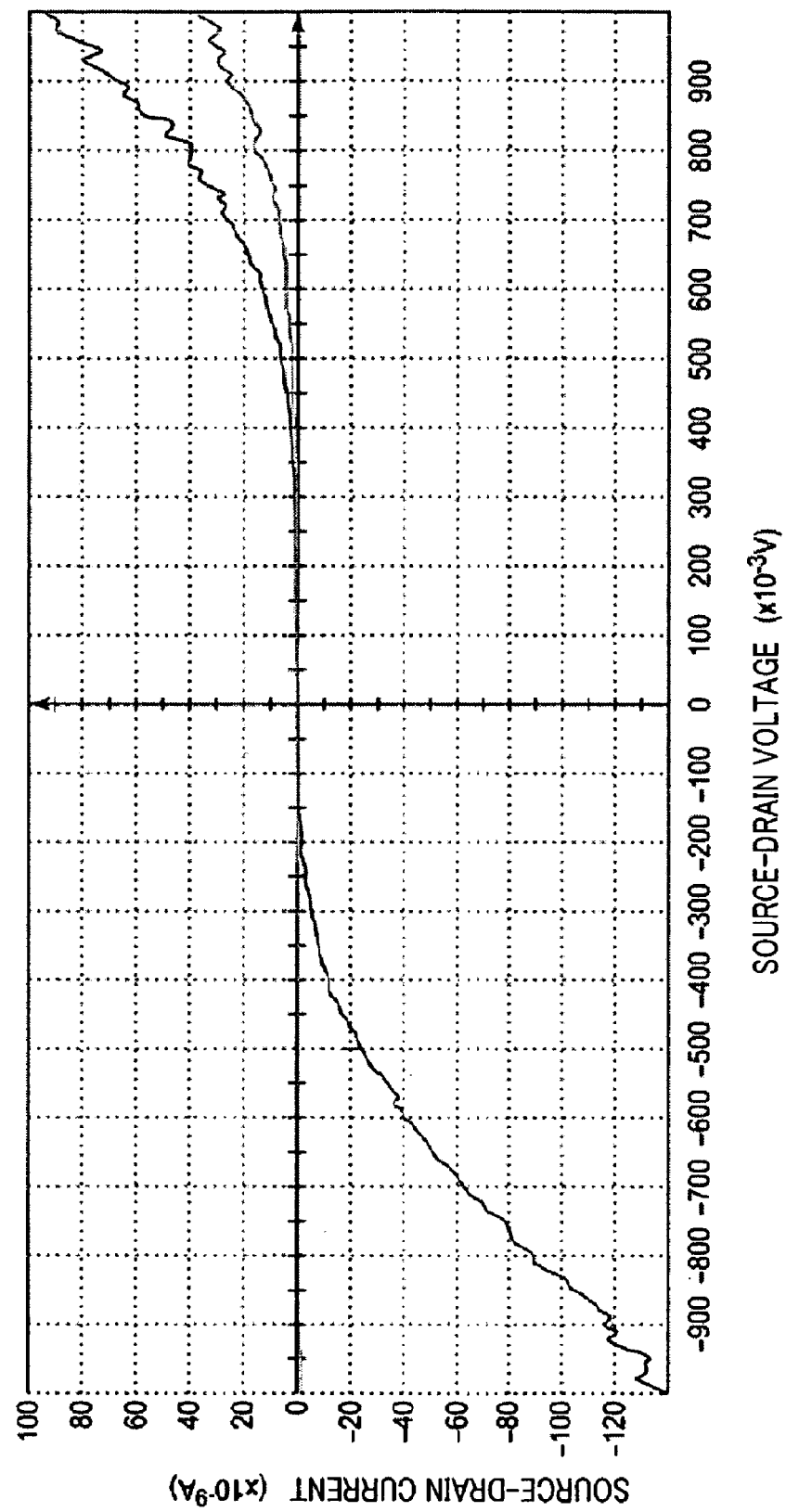

FIG. 27 is a view showing I-V characteristics of separate-gate FET according to the present invention for a case where interval between ultra fine fiber element section and gate element section is 15 mm.

Figure 28:
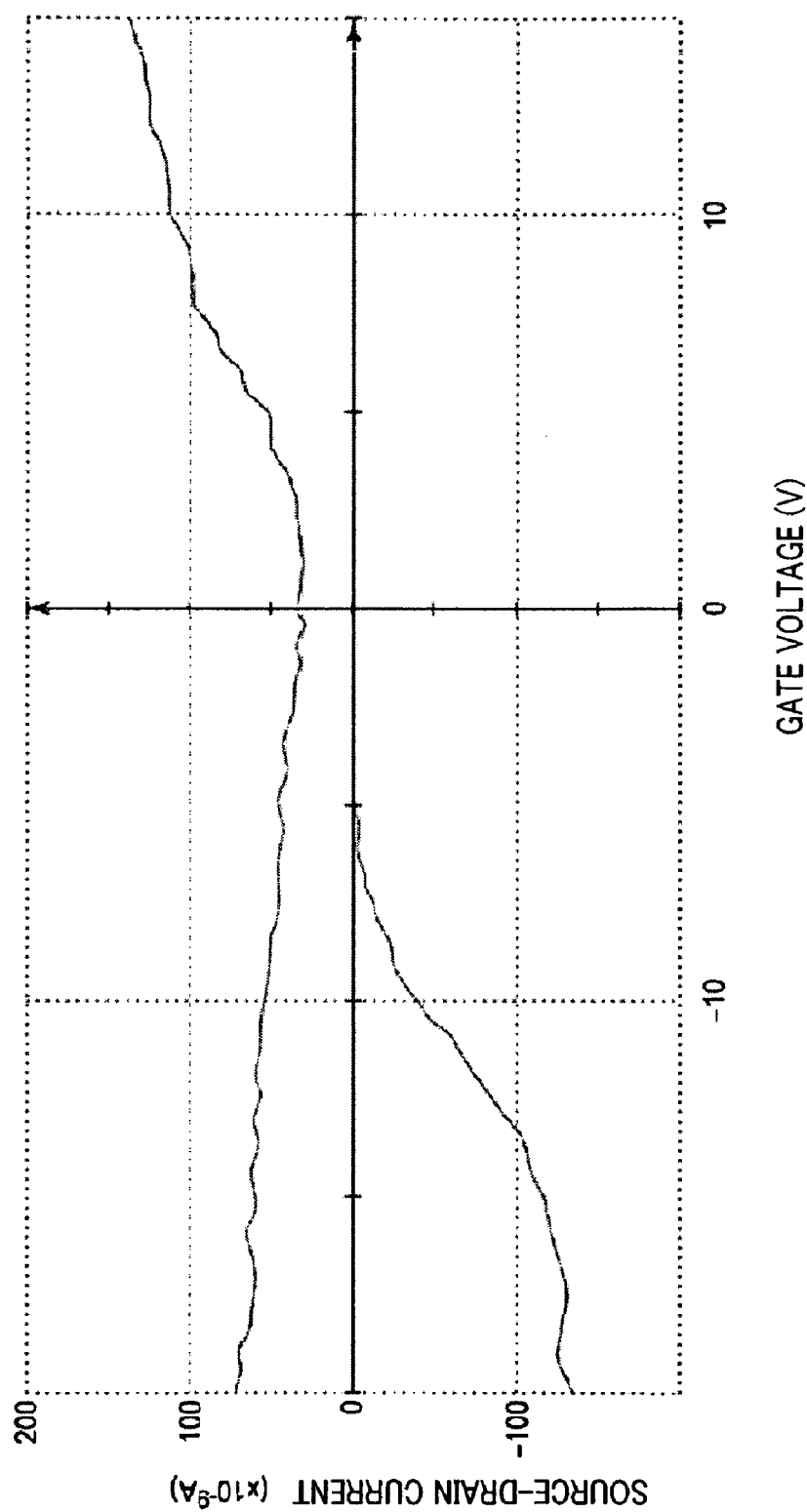

FIG. 28 is a view showing I-Vg characteristics of separate-gate FET according to the present invention for a case where interval between ultra fine fiber element section and gate element section is 15 mm.

Figure 29:
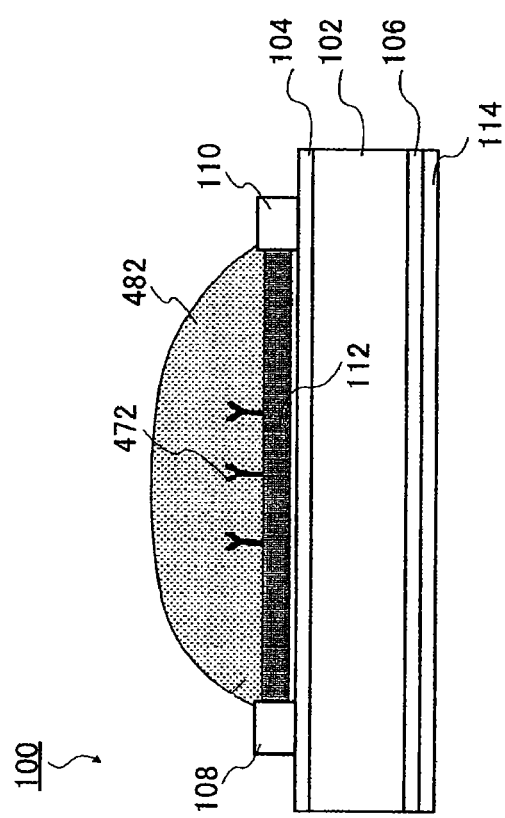

FIG. 29 is a view showing an example where, in back-gate FET according to the present invention, a detection target substance capturing molecule is bound to ultra fine fiber. Reference number 100 denotes back-gate FET according to the present invention, 102 denotes support substrate, 104 denotes first insulating film, 106 denotes second insulating film, 108 denotes source electrode, 110 denotes drain electrode, 112 denotes ultra fine fiber, 114 denotes gate electrode, 472 denotes detection target substance capturing molecule, and 482 denotes sample solution.

Figure 30:
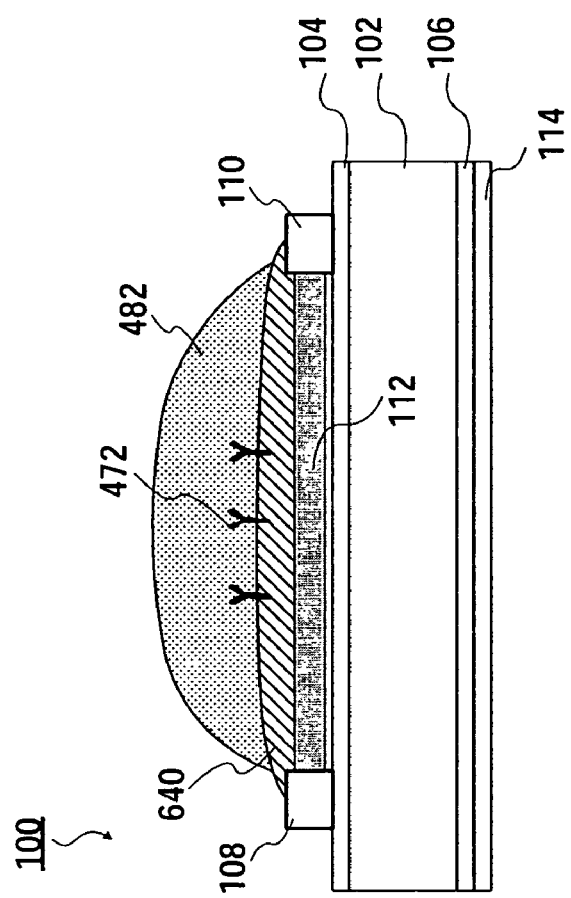

FIG. 30 is a view showing an example where, in back-gate FET according to the present invention, Reference number 100 denotes back-gate FET according to the present invention, 102 denotes support substrate, 104 denotes first insulating film, 106 denotes second insulating film, 108 denotes source electrode, 110 denotes drain electrode, 112 denotes ultra fine fiber, 114 denotes gate electrode, 472 denotes detection target substance capturing molecule, 482 denotes sample solution, and 640 denotes insulating protective film FIGS. 31A-D are views showing examples where, in back-gate FET according to the present invention, a detection target substance capturing molecule is bound to a second insulating film. Reference numbers 510, 520, and 520a denote back-gate FET according to the present invention, 102 denotes support substrate, 104 denotes first insulating film, 106 denotes second insulating film, 108 denotes source electrode, 110 denotes drain electrode, 112 denotes ultra fine fiber, 512, 522, 522a, and 522b denote gate electrode, 472, 472a, and 472b denote detection target substance capturing molecule, 490, 490a, and 490b denote sample solution.

FIGS. 32A-E are views showing other examples where, the detection target substance capturing molecule is bound to the second insulating film. Reference number 102 denotes support substrate, 104 denotes first insulating film, 106 denotes second insulating film, 108 denotes source electrode, 110 denotes drain electrode, 112 denotes ultra fine fiber, 114 denotes gate electrode, 116 denotes concave sidewall, 472 denotes detection target substance capturing molecule, and 482 denotes sample solution.

Figure 33A:
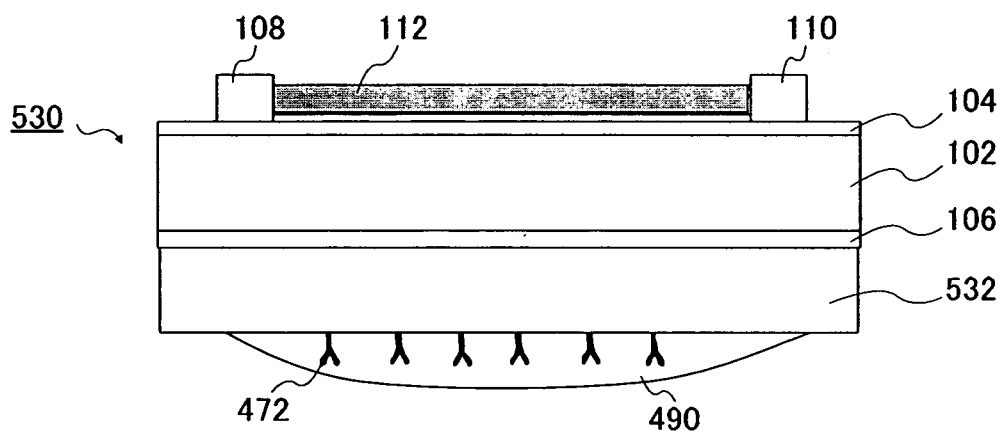
Figure 33B:
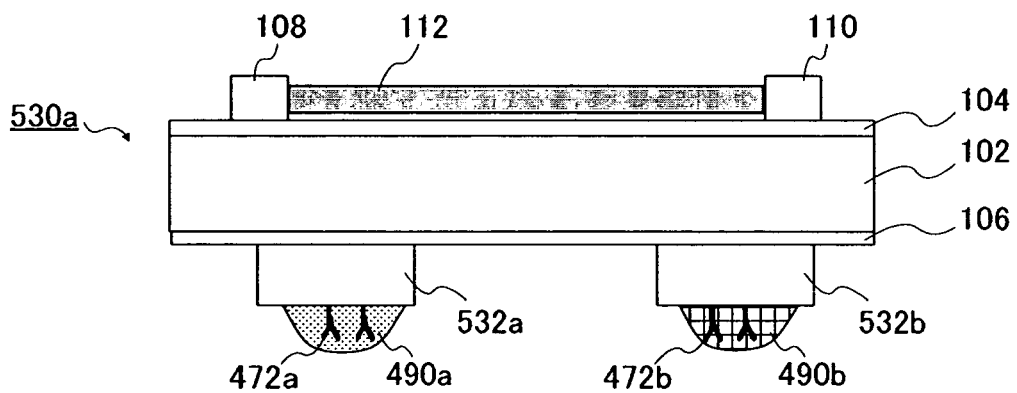

FIGS. 33A and 33B are views showing examples where, in back-gate FET according to the present invention, a detection target substance capturing molecule is bound to a gate electrode. Reference number 530 and 530a denote back-gate FET according to the present invention, 102 denotes support substrate, 104 denotes first insulating film, 106 denotes second insulating film, 108 denotes source electrode, 110 denotes drain electrode, 112 denotes ultra fine fiber, 532, 532a, and 532b denote gate electrode, 472, 472a, and 472b denote detection target substance capturing molecule, 490, 490a, and 490b denote sample solution.

Figure 34:
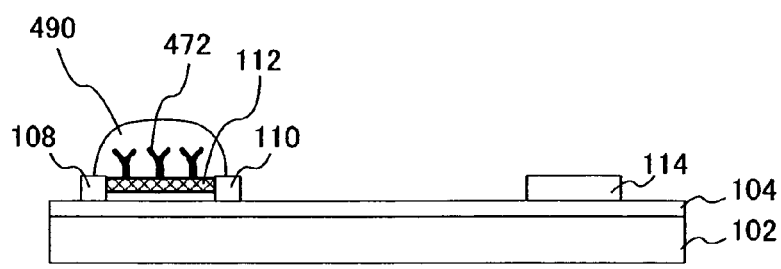

FIG. 34 is a view showing an example where, in side-gate FET according to the present invention, a detection target substance capturing molecule is bound to ultra fine fiber. Reference number 102 denotes support substrate, 104 denotes first insulating film, 108 denotes source electrode, 110 denotes drain electrode, 112 denotes ultra fine fiber, 114 denotes gate electrode, 472 denotes detection target substance capturing molecule, and 490 denotes sample solution.

Figure 35A:
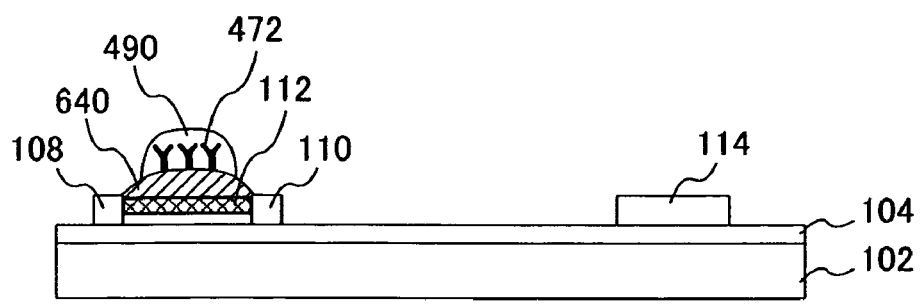
Figure 35B:
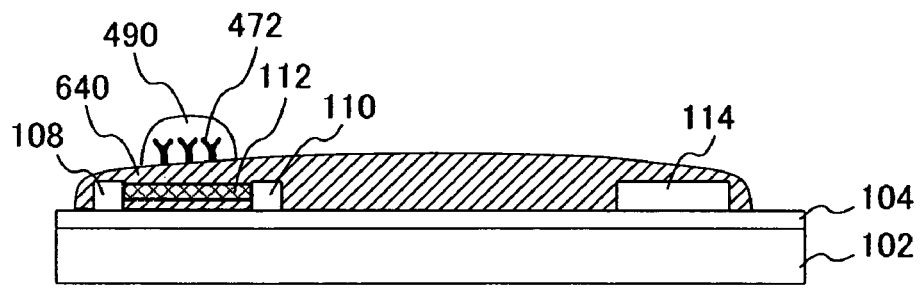

FIGS. 35A and 35B are views showing examples where, in side-gate FET according to the present invention, a detection target substance capturing molecule is bound to an insulating protective film. Reference number 102 denotes support substrate, 104 denotes first insulating film, 108 denotes source electrode, 110 denotes drain electrode, 112 denotes ultra fine fiber, 114 denotes gate electrode, 472 denotes detection target substance capturing molecule, 490 denotes sample solution, and 640 denotes insulating protective film.

Figure 36A:
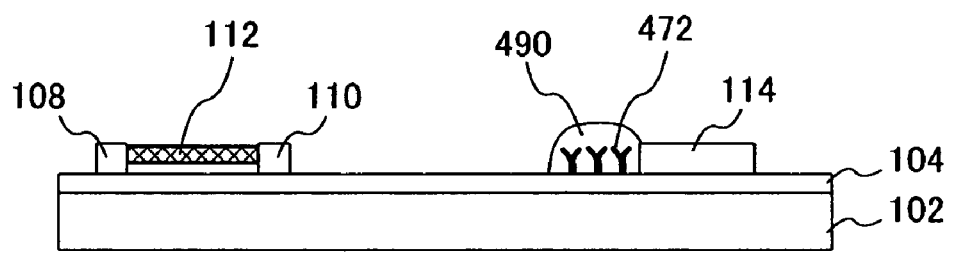
Figure 36B:
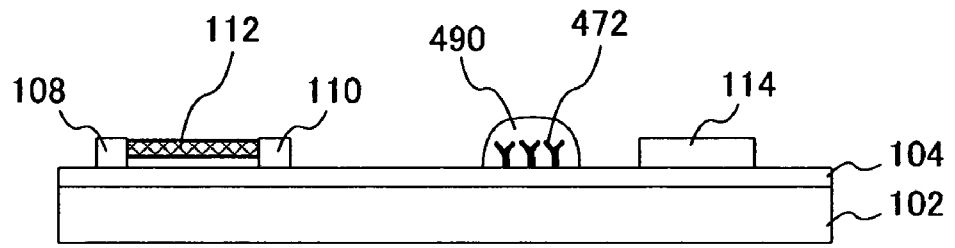

FIGS. 36A and 36B are views showing examples where, in side-gate FET according to the present invention, a detection target substance capturing molecule is bound to a first insulating film. Reference number 102 denotes support substrate, 104 denotes first insulating film, 108 denotes source electrode, 110 denotes drain electrode, 112 denotes ultra fine fiber, 114 denotes gate electrode, 472 denotes detection target substance capturing molecule, and 490 denotes sample solution.

Figure 37:
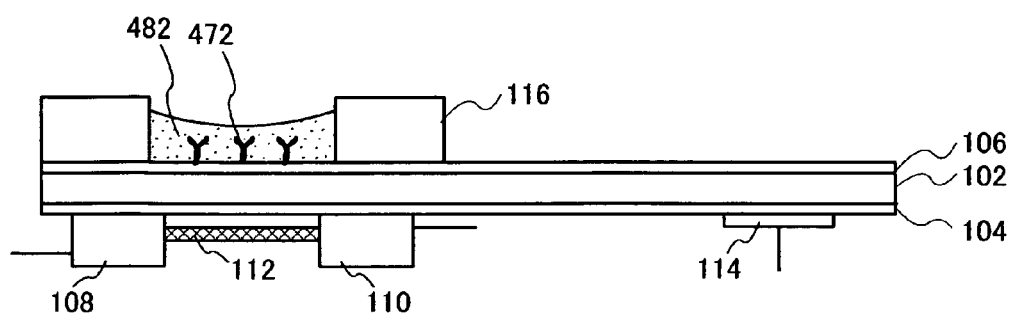

FIG. 37 is a view showing another example where, in side-gate FET according to the present invention, the detection target substance capturing molecule is bound to a second insulating film. Reference number 102 denotes support substrate, 104 denotes first insulating film, 106 denotes second insulating film, 108 denotes source electrode, 110 denotes drain electrode, 112 denotes ultra fine fiber, 114 denotes gate electrode, 116 denotes concave sidewall, 472 denotes detection target substance capturing molecule, and 482 denotes sample solution.

Figure 38:
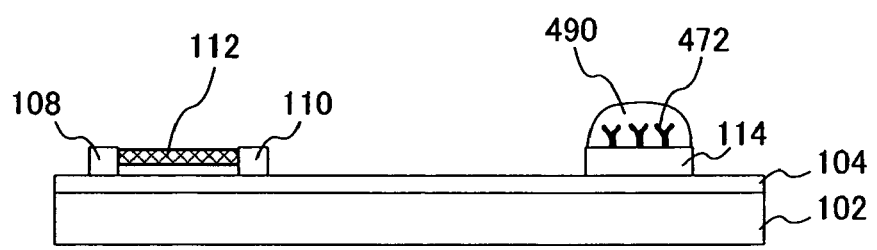

FIG. 38 is a view showing an example where, in side-gate FET according to the present invention, a detection target substance capturing molecule is bound to a gate electrode. Reference number 102 denotes support substrate, 104 denotes first insulating film, 108 denotes source electrode, 110 denotes drain electrode, 112 denotes ultra fine fiber, 114 denotes gate electrode, 472 denotes detection target substance capturing molecule, and 490 denotes sample solution.

FIG. 39 is a view showing an example where, in separate-gate FET according to the present invention, a detection target substance capturing molecule is bound to an insulating film of gate element section. Reference number 600 denotes separate-gate FET according to the present invention, 102 denotes first support substrate, 104 denotes first insulating film, 106 denotes second insulating film, 108 denotes source electrode, 110 denotes drain electrode, 112 denotes ultra fine fiber, 202 denotes second support substrate; 204 denotes third insulating film, 206 denotes fourth insulating film, 472 denotes detection target substance capturing molecule, 490 denotes sample solution, 602 denotes gate electrode, 210 denotes conductive substrate, 212 denotes ultra fine fiber element section, and 214 denotes gate element section.

Figure 40A:
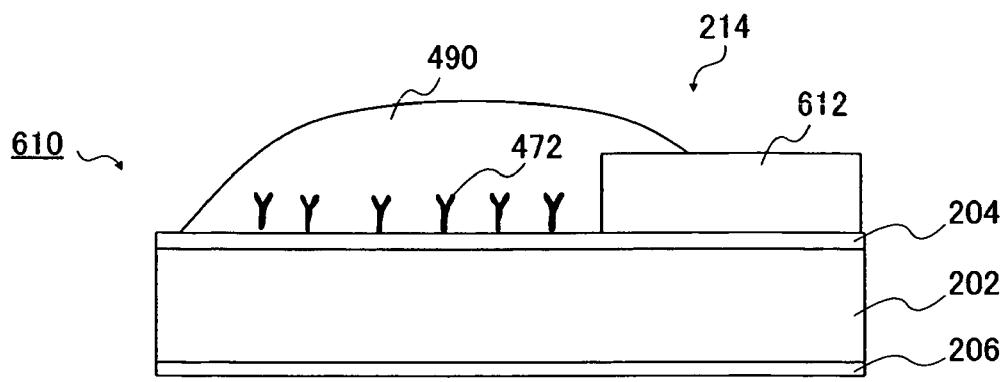
Figure 40B:
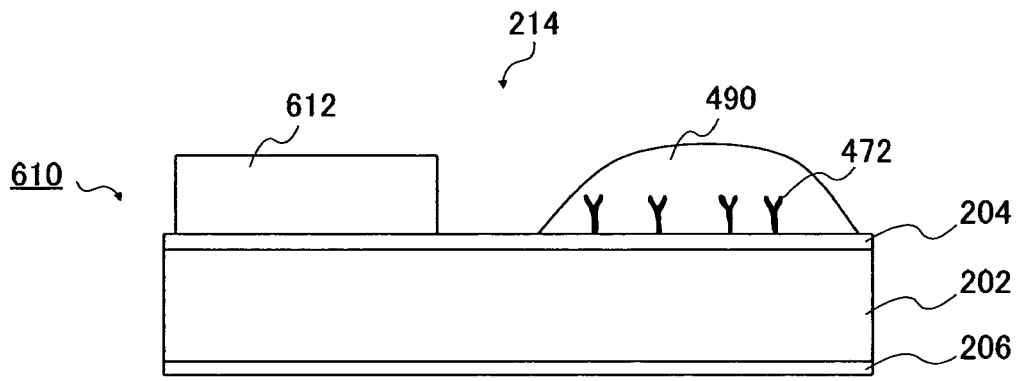
Figure 40C:
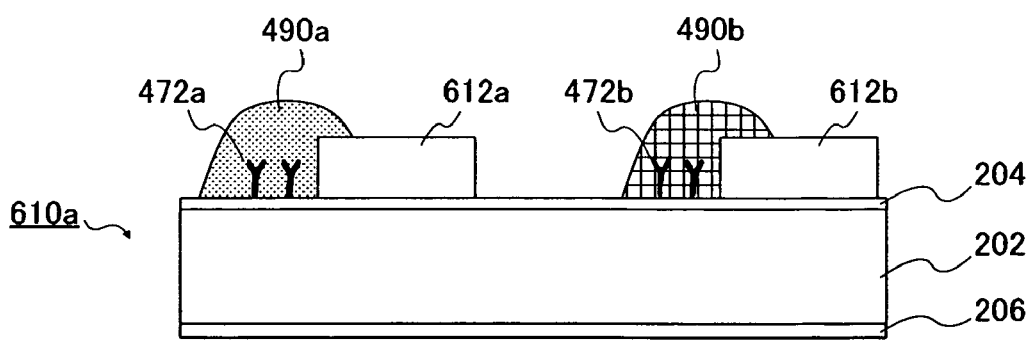

FIGS. 40A-C are views showing other examples where, in separate-gate FET according to the present invention, the detection target substance capturing molecule is bound to the insulating film of gate element section. Reference number 610 and 610a denote gate element section, 202 denotes second support substrate, 204 denotes third insulating film, 206 denotes fourth insulating film, 472, 472a, and 472b denote detection target substance capturing molecule, 490, 490a, and 490b denote sample solution, 612, 612a, and 612b denote gate electrode.

Figure 41A:
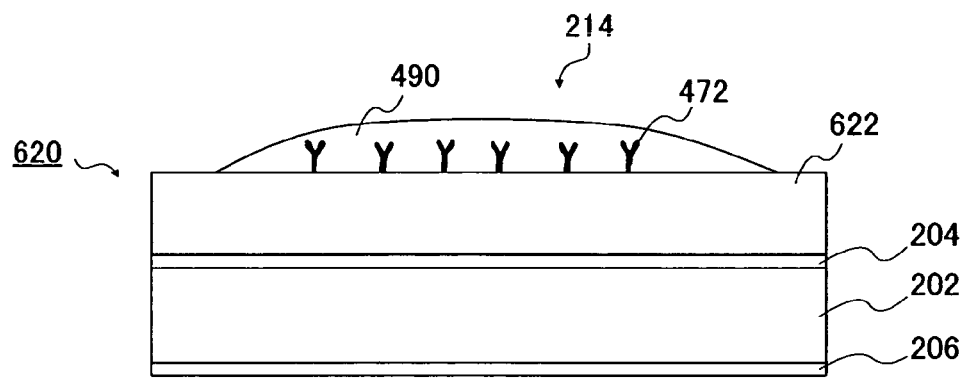
Figure 41B:
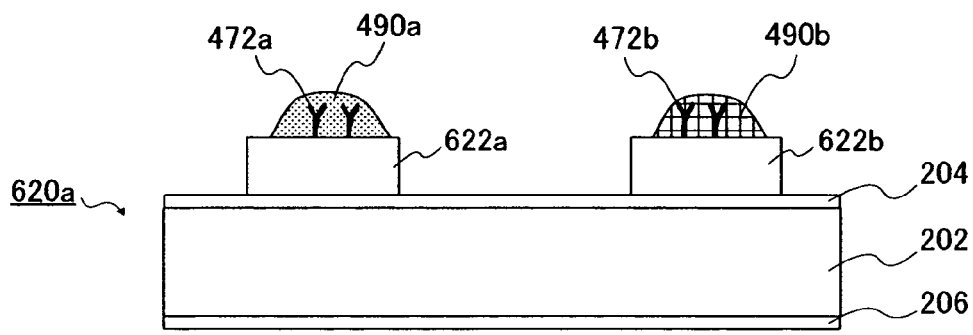

FIGS. 41A and 41B are views showing examples where, in separate-gate FET according to the present invention, a detection target substance capturing molecule is bound to a gate electrode of gate element section. Reference number 620 and 620a denote gate element section, 202 denotes second support substrate, 204 denotes third insulating film, 206 denotes fourth insulating film, 472, 472a, and 472b denote detection target substance capturing molecule, 490, 490a, and 490b denote sample solution, 622, 622a, and 622b denote gate electrode.

Figure 42:
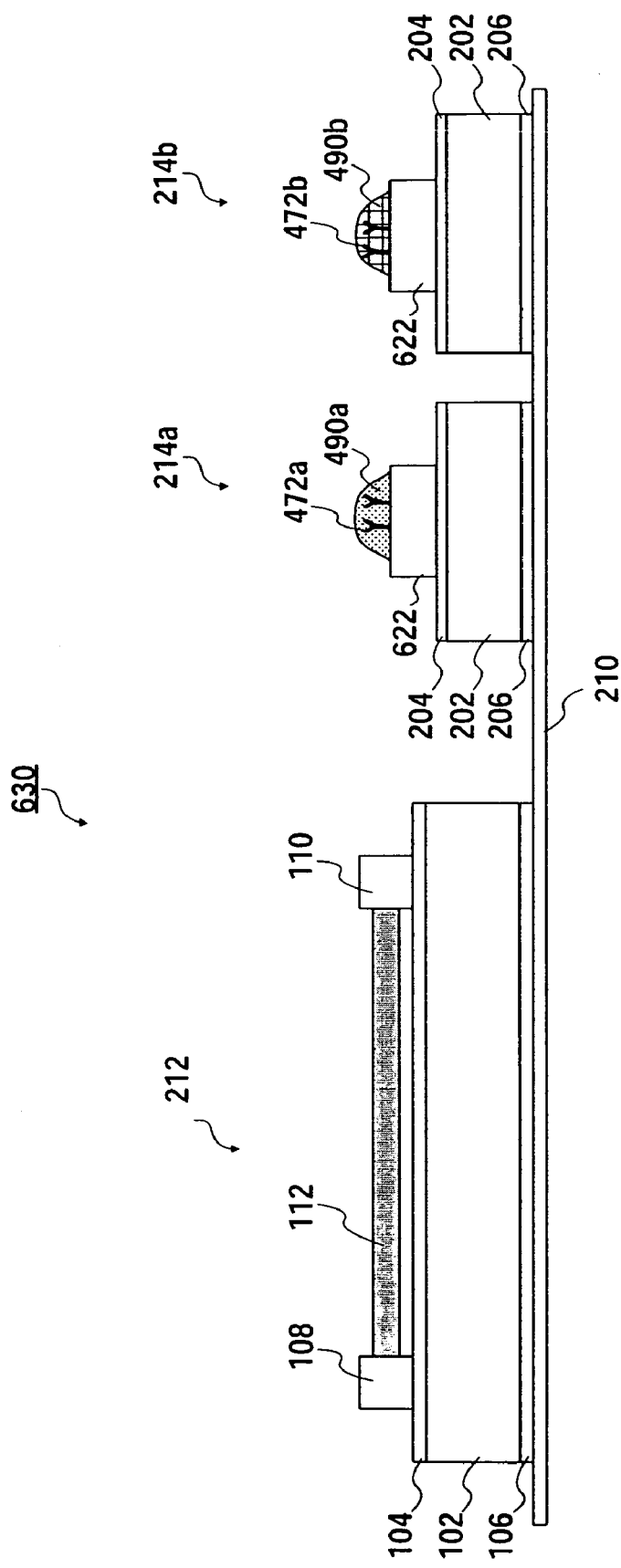

FIG. 42 is a view showing an example where, in separate-gate FET according to the present invention, when there are a plurality of gate element sections, a plurality of types of detection target substance capturing molecules are bound to each of gate electrodes. Reference number 630 denotes separate-gate FET according to the present invention, 102 denotes first support substrate, 104 denotes first insulating film, 106 denotes second support substrate, 108 denotes source electrode, 110 denotes drain electrode, 112 denotes ultra fine fiber, 202 denotes second support substrate, 204 denotes third insulating film, 206 denotes fourth insulating film, 472a and 472b denote detection target substance capturing molecule, 490a and 490b denote sample solution, 622 denotes gate electrode, 210 denotes conductive substrate, 212 denotes ultra fine fiber element section, 214a and 214b denote gate element section.

Figure 43:
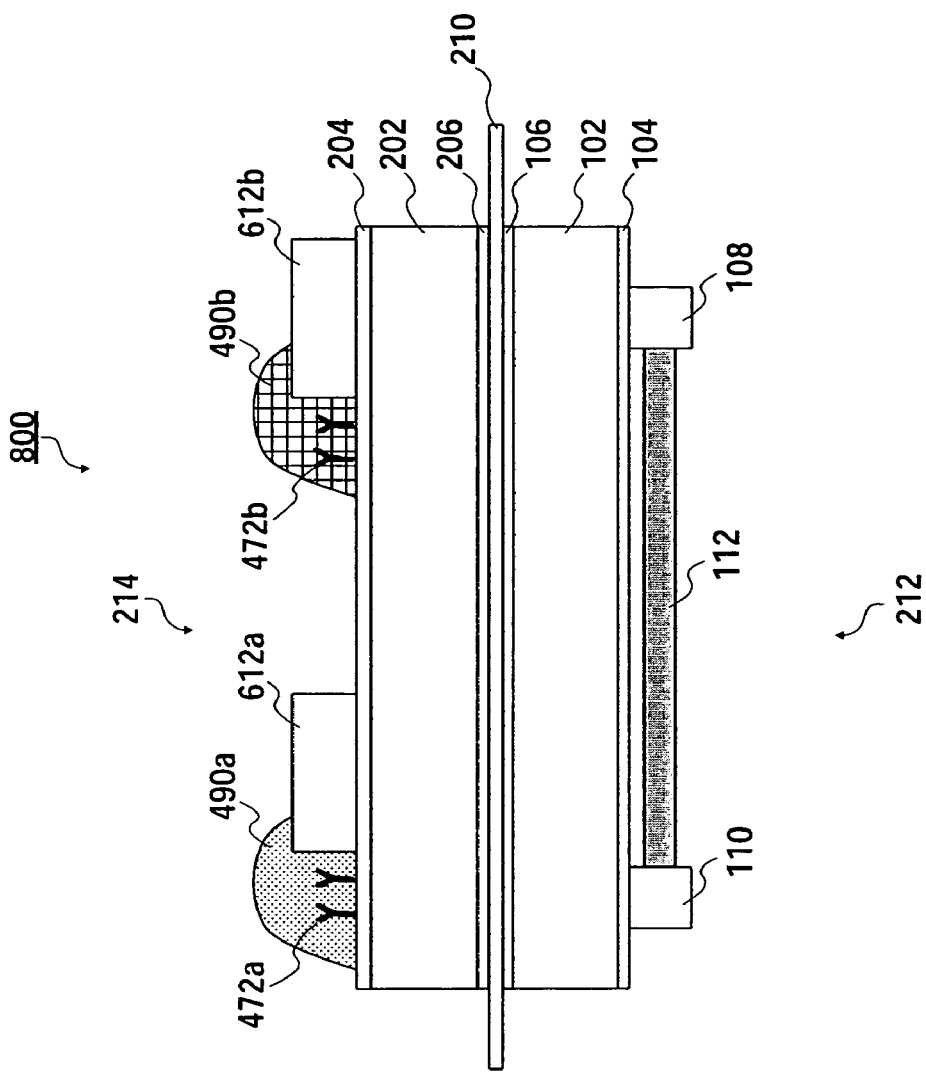

FIG. 43 is a view showing an example where, in separate-gate FET according to the present invention, a plurality of types of detection target substance capturing molecules are bound to each of insulating films of the gate element section. Reference number 800 denotes separate-gate FET according to the present invention, 102 denotes first support substrate, 104 denotes first insulating film, 106 denotes second insulating film, 108 denotes source electrode, 110 denotes drain electrode, 112 denotes ultra fine fiber, 202 denotes second support substrate, 204 denotes third insulating film, 206 denotes fourth insulating film, 472a and 472b denote detection target substance capturing molecule, 490a and 490b denote sample solution, 612a and 612b denote gate electrode, 210 denotes conductive substrate, 212 denotes ultra fine fiber element section, and 214 denotes gate element section.

FIG. 44 is a view showing another example where, in separate-gate FET according to the present invention, a plurality of types of detection target substance capturing molecules are bound to each of insulating films of the gate element section. Reference number 900 denotes separate-gate FET according to the present invention, 102 denotes first support substrate, 104 denotes first insulating film, 106 denotes second insulating film, 108 denotes source electrode, 110 denotes drain electrode, 112 denotes ultra fine fiber, 202 denotes second support substrate, 204 denotes third insulating film, 206 denotes fourth insulating film, 472a and 472b denote detection target substance capturing molecule, 490a and 490b denote sample solution, 612a and 612b denote gate electrode, 302 denotes first conductive substrate, 304 denotes second conductive substrate, 306 denotes conductive member, 212 denotes ultra fine fiber element section, and 214 denotes gate element section.

FIGS. 45A-D are views for explanation of a method for binding the detection target substance capturing molecule. Reference number 50 denotes antibody, 51 denotes his-tag, 52 denotes NTA, 53 denotes IgG binding protein, 54 denotes heterobifunctional crosslinking reagent, 55 and 56 denote functional group.

FIG. 46 is a schematic view showing one example of the biosensor device according to the present invention. Reference number 7601 denotes biosensor body, 7604 denotes display section, and 7702 denotes element section.

Figure 47:
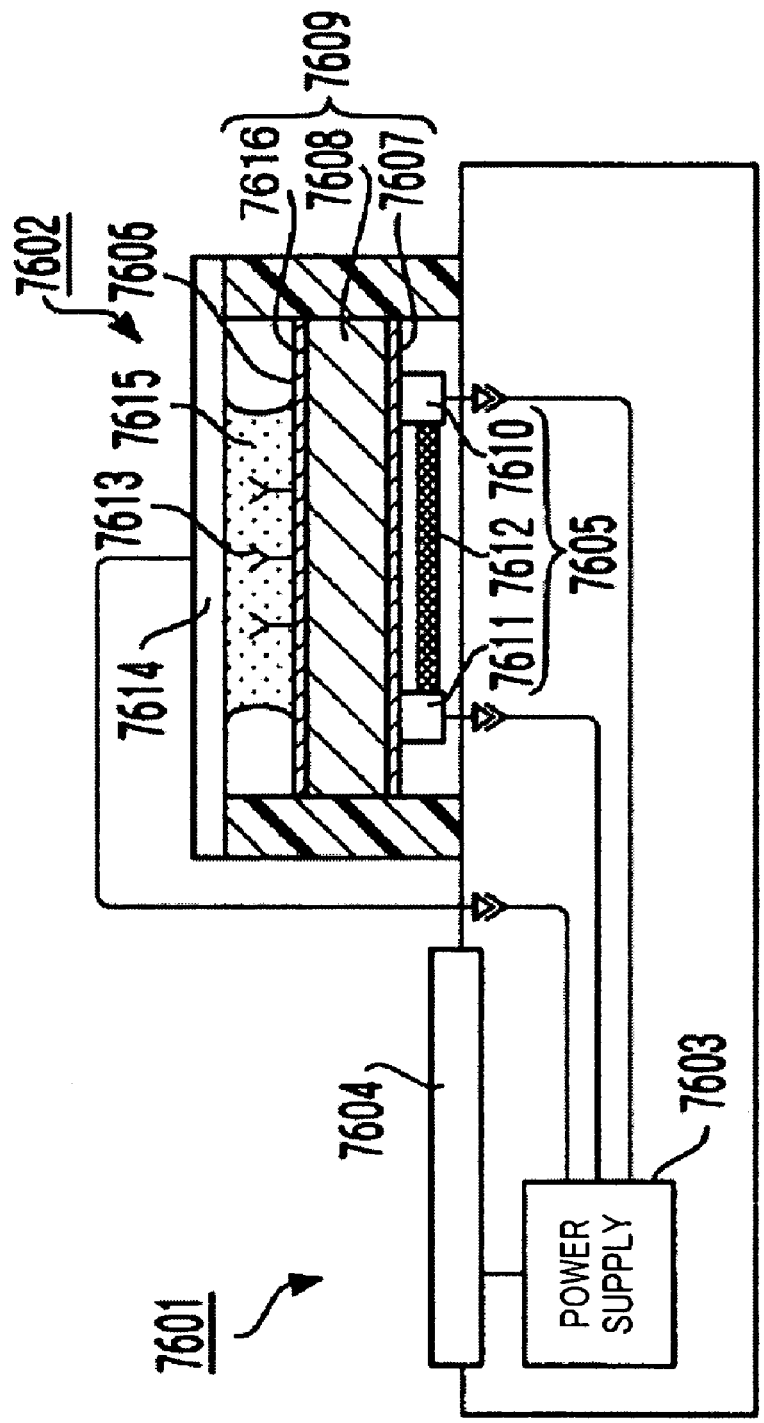

FIG. 47 is a cross-sectional view showing outline of the composition of a biosensor device having back-gate FET according to the present invention at the element section. Reference number 7601 denotes biosensor device body, 7602 denotes element section, 7603 denotes power supply, 7604 denotes display section, 7605 denotes ultra fine fiber element, 7607 denotes first insulating film, 7608 denotes support substrate, 7609 denotes substrate, 7610 denotes source electrode, 7611 denotes drain electrode, 7612 denotes ultra fine fiber, 7613 denotes detection target substance capturing molecule, 7614 denotes gate electrode, 7615 denotes sample solution, and 7616 denotes second insulating film.

Figure 48A:
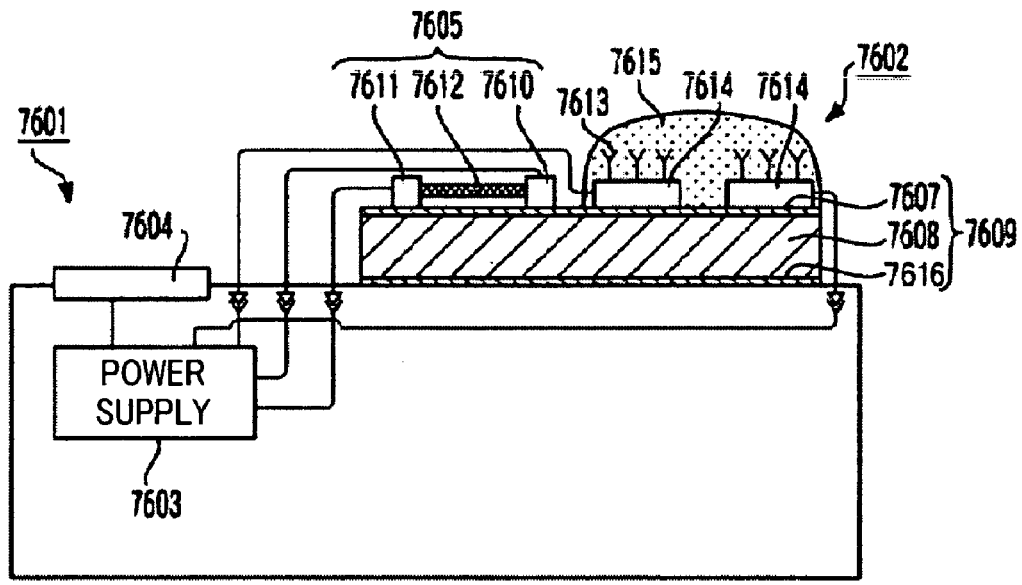
Figure 48B:
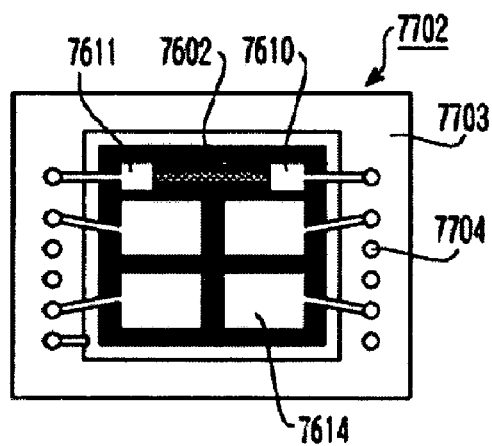

FIG. 48A is a cross-sectional view showing outline of the composition of one example of a biosensor device having side-gate FET according to the present invention at the element section. FIG. 48B is a plan view of a chip used in the biosensor device illustrated in FIG. 48A. Reference number 7601 denotes biosensor device body, 7602 denotes element section, 7603 denotes power supply, 7604 denotes display section, 7605 denotes ultra fine fiber, 7607 denotes first insulating film, 7608 denotes support substrate, 7609 denotes substrate, 7610 denotes source electrode, 7611 denotes drain electrode, 7612 denotes ultra fine fiber, 7613 denotes detection target substance capturing molecule, 7614 denotes gate electrode, 7615 denotes sample solution, 7616 denotes second insulating film, 7702 denotes chip, 7703 denotes case, and 7704 denotes conductive pin.

Figure 49A:
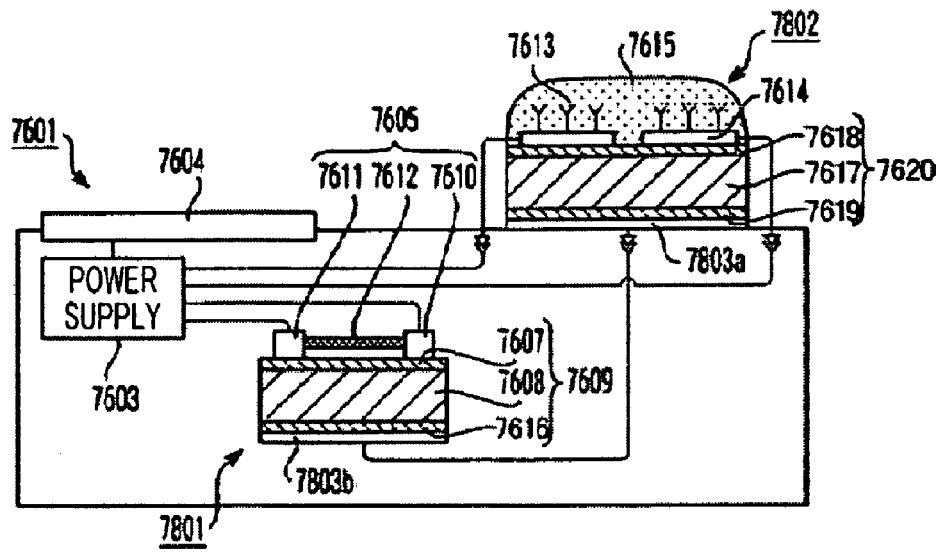
Figure 49B:
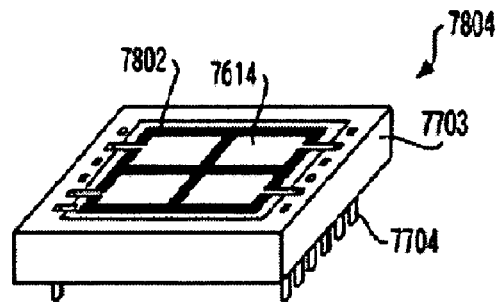
Figure 49C:
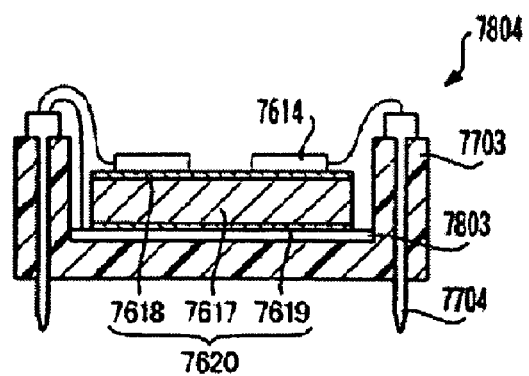

FIG. 49A is a cross-sectional view showing outline of the composition of one example of a biosensor device having gate element section of separate-gate FET according to the present invention at the element section. FIG. 49B is a perspective view of the chip used for the biosensor device illustrated in FIG. 49A. FIG. 49C is a cross-sectional view of the chip used for the biosensor device illustrated in FIG. 49A. Reference number 7601 denotes biosensor device body, 7603 denotes power supply, 7604 denotes display section, 7605 denotes ultra fine fiber element, 7607 denotes first insulating film, 7608 denotes first support substrate, 7609 denotes substrate, 7610 denotes source electrode, 7611 denotes drain electrode, 7612 denotes ultra fine fiber, 7613 denotes detection target substance capturing molecule, 7614 denotes gate electrode, 7615 denotes sample solution, 7616 denotes second insulating film, 7617 denotes second support substrate, 7618 denotes third insulating film, 7619 denotes fourth insulating film, 7620 denotes second substrate, 7703 denotes case, 7704 denotes conductive pin, 7802 denotes element section, 7803, 7803a, and 7803b denote conductive substrate, and 7804 denotes chip.

Figure 50A:
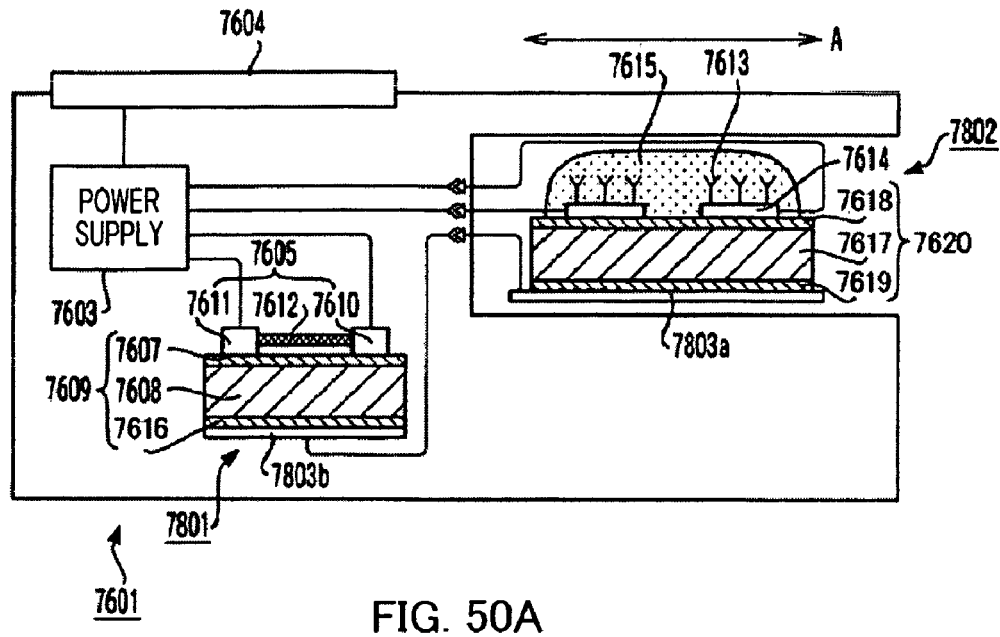
Figure 50B:
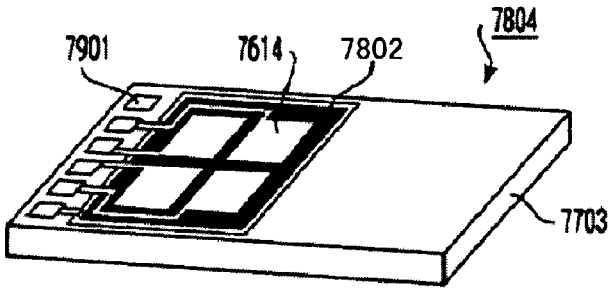
Figure 50C:
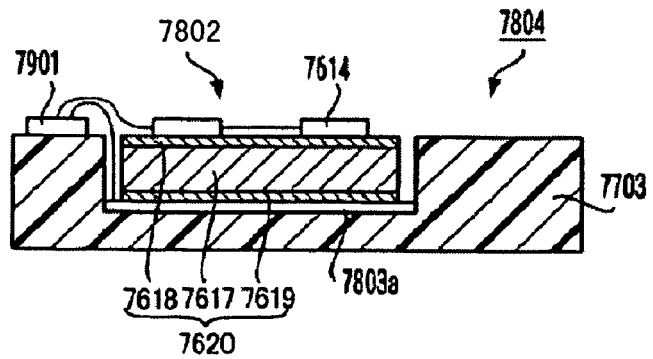

FIG. 50A is a cross-sectional view showing outline of the composition of another example of the biosensor device having gate element section of separate-gate FET according to the present invention at the element section. FIG. 50B is a perspective view of a chip used for the biosensor device illustrated in FIG. 50A. FIG. 50C is a cross-sectional view of the chip used for the biosensor device illustrated in FIG. 50A. Reference number 7601 denotes biosensor device body, 7603 denotes power supply, 7604 denotes display section, 7605 denotes ultra fine fiber element, 7607 denotes first insulating film, 7608 denotes first support substrate, 7609 denotes substrate, 7610 denotes source electrode, 7611 denotes drain electrode, 7612 denotes ultra fine fiber, 7613 denotes detection target substance capturing molecule, 7614 denotes gate electrode, 7615 denotes sample solution, 7616 denotes second insulating film, 7617 denotes second support substrate, 7618 denotes third insulating film, 7619 denotes fourth insulating film, 7703 denotes case, 7802 denotes element section, 7803a and 7803b denote conductive substrate, 7804 denotes chip, and 7901 denotes plate electrode.

FIGS. 51A-D are cross-sectional views showing an example of a chip used for biosensor device having gate element section of separate-gate FET according to the present invention at the element section. Reference number 7613 denotes detection target substance capturing molecule, 7614 denotes gate electrode, 7620 denotes second substrate, 7704 denotes conductive pin, 7803*a* denotes conductive substrate, 7804 denotes chip, 8001 denotes connection terminal, and 8002 denotes cover.

Figure 52A:
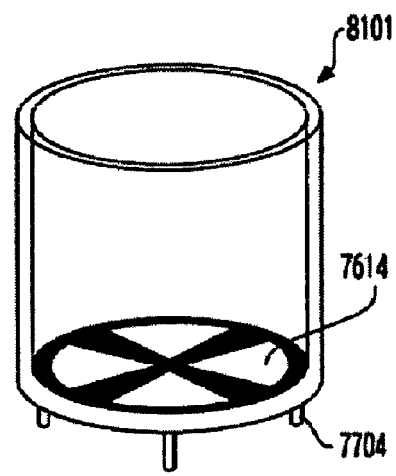
Figures 52B, 52C:
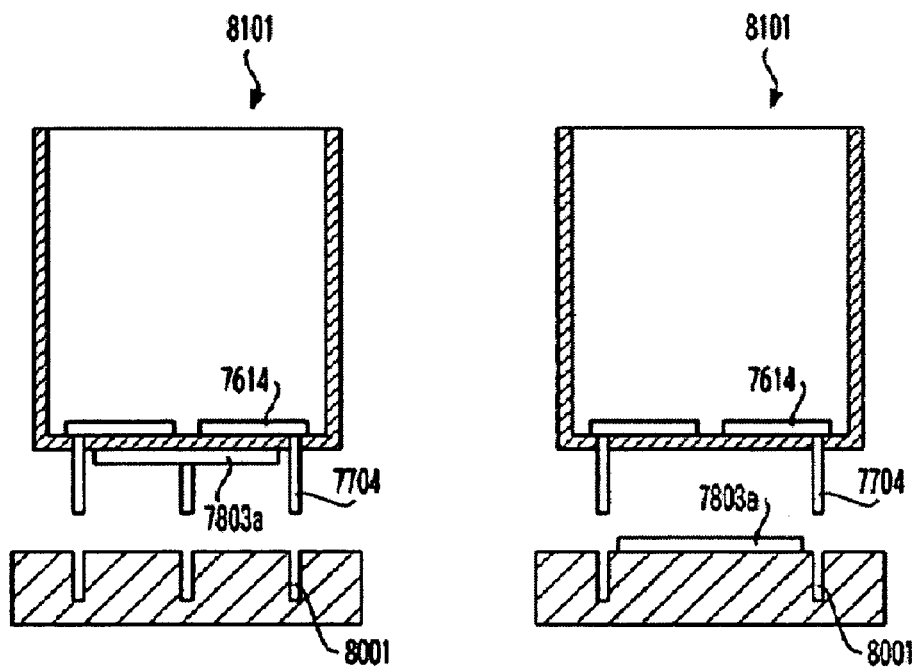

FIG. 52A is a perspective view showing one example of a chip having concave part. FIG. 52B is a cross-sectional view showing one example of the chip having concave part. FIG. 52C is a cross-sectional view showing another example of the chip having concave part. Reference number 7614 denotes gate electrode, 7704 denotes conductive pin, 7803*a* denotes conductive substrate, 8001 denotes connection terminal, and 8101 denotes the chip having concave part.

Figure 53A:
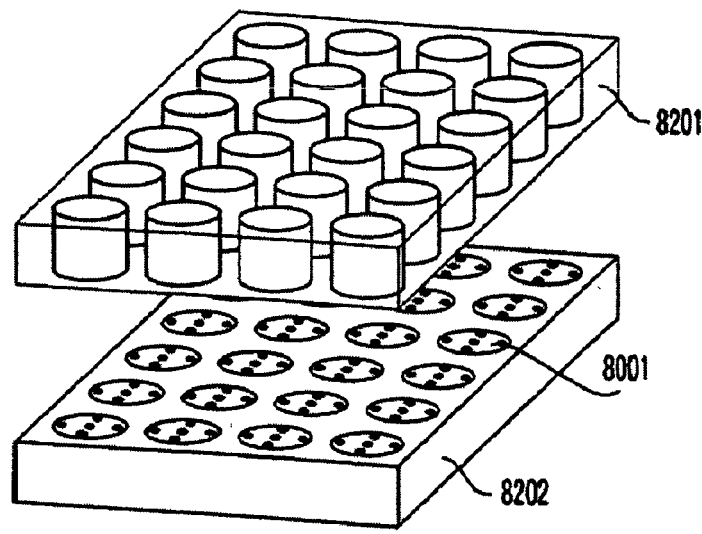
Figure 53B:
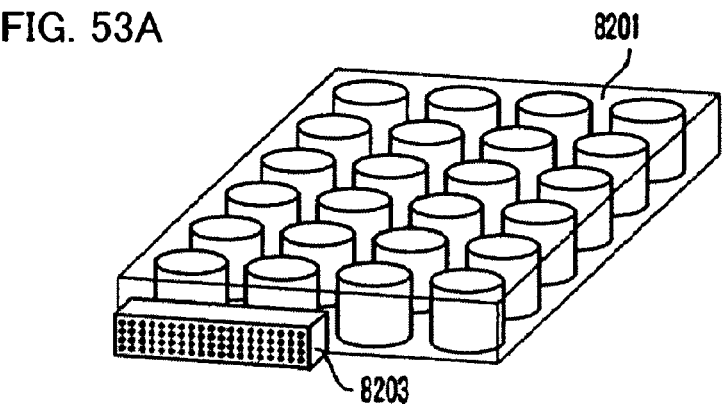
Figure 53C:
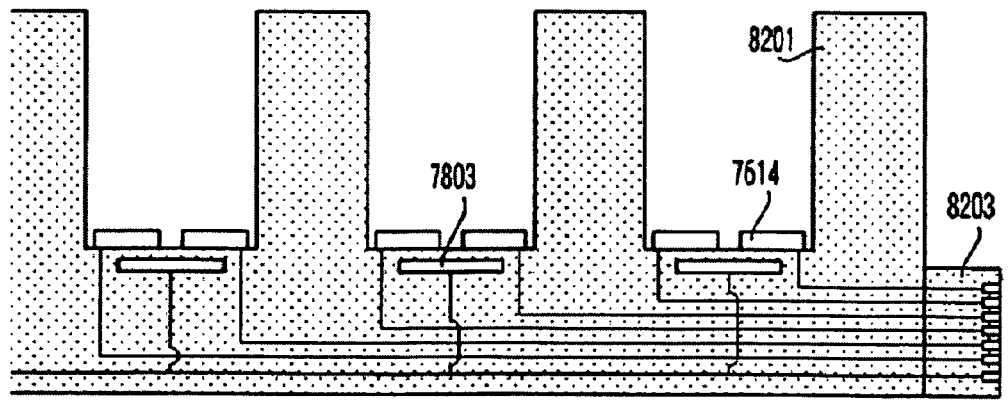

FIG. 53A is a perspective view of one example of microplate type chip. FIG. 53B is a perspective view showing another example of the microplate type chip. FIG. 53C is a cross-sectional view of the microplate type chip illustrated in FIG. 53B. Reference number 7614 denotes gate electrode, 7803 denotes conductive substrate, 8001 denotes connection terminal, 8201 denotes microplate type chip, 8202 denotes socket, and 8203 denotes electrical contact.

Figure 54A:
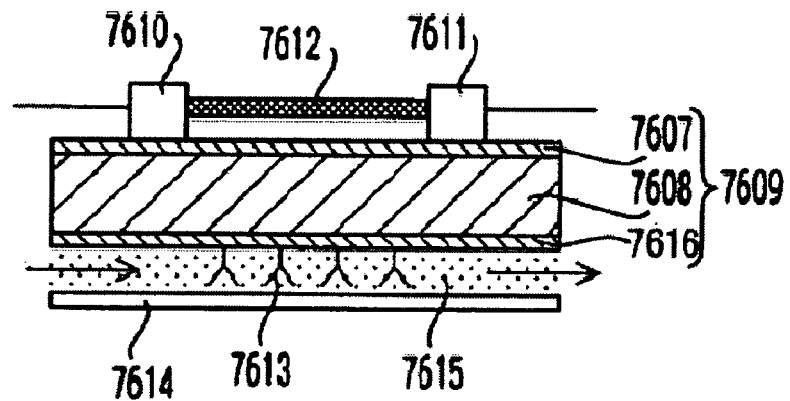
Figure 54B:
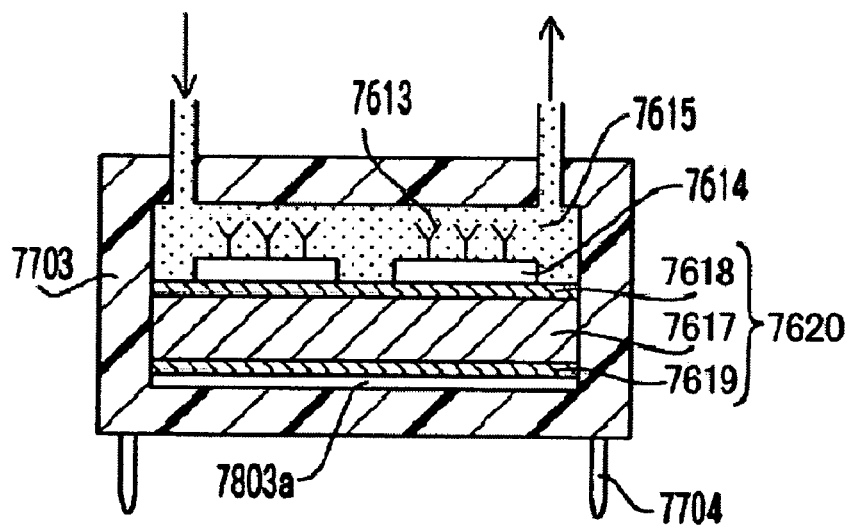

FIG. 54A is a cross-sectional view showing one example of a chip having back-gate FET. FIG. 54B is a cross-sectional view showing one example of a chip having gate element section of separate-gate FET. Reference number 7607 denotes first insulating film, 7608 denotes support substrate, 7609 denotes substrate, 7610 denotes source electrode, 7611 denotes drain electrode, 7612 denotes ultra fine fiber, 7613 denotes detection target substance capturing molecule, 7614 denotes gate electrode, 7615 denotes sample solution, 7617 denotes second support substrate, 7618 denotes third insulating film, 7619 denotes fourth insulating film, 7620 denotes second substrate, 7703 denotes case, 7704 denotes conductive pin, and 7803*a* denotes conductive substrate.

Figure 55A:
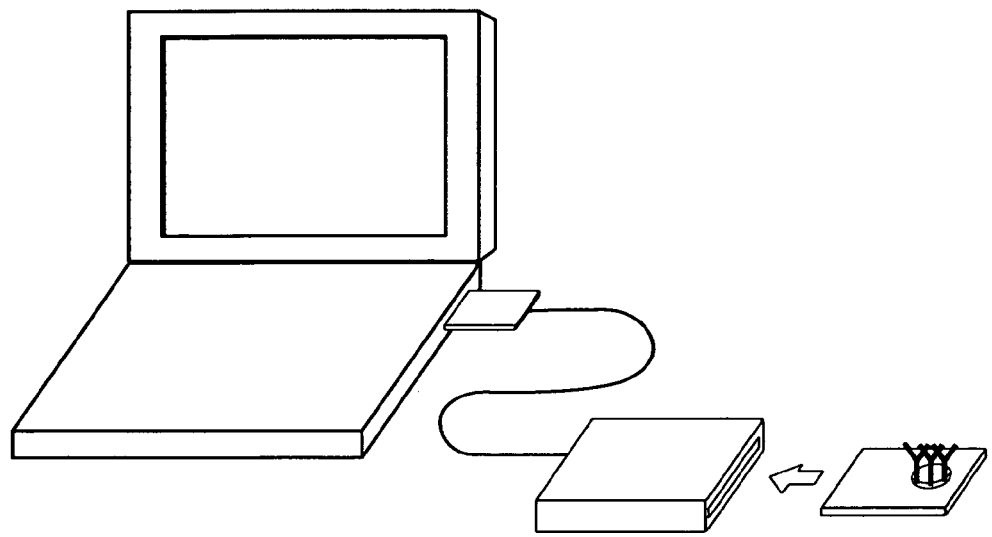
Figure 55B:
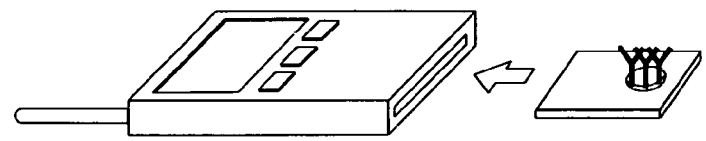

FIG. 55A is a view showing one example of a biosensor device driven by battery of a notebook-sized personal computer. FIG. 55B is a view showing one example of a battery driven small-sized biosensor device.

Figure 56:
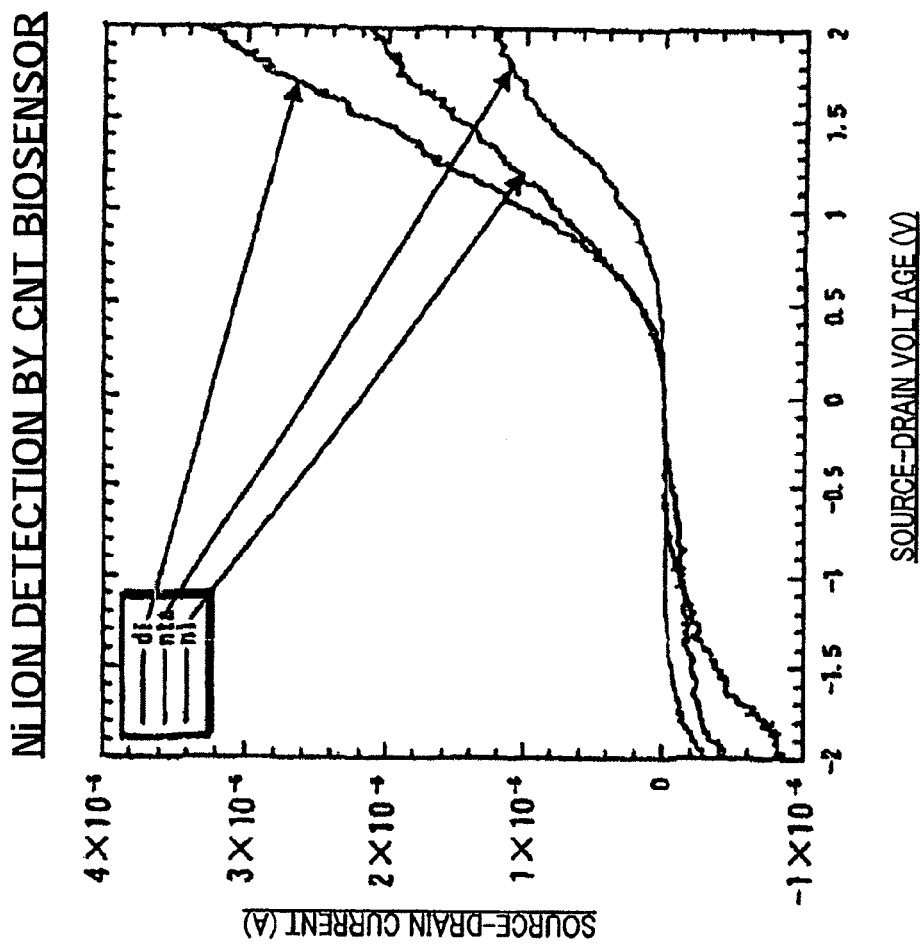

FIG. 56 is a view showing I-V characteristics curve at nickel ion detection by the biosensor according to the present invention.

Figure 57:
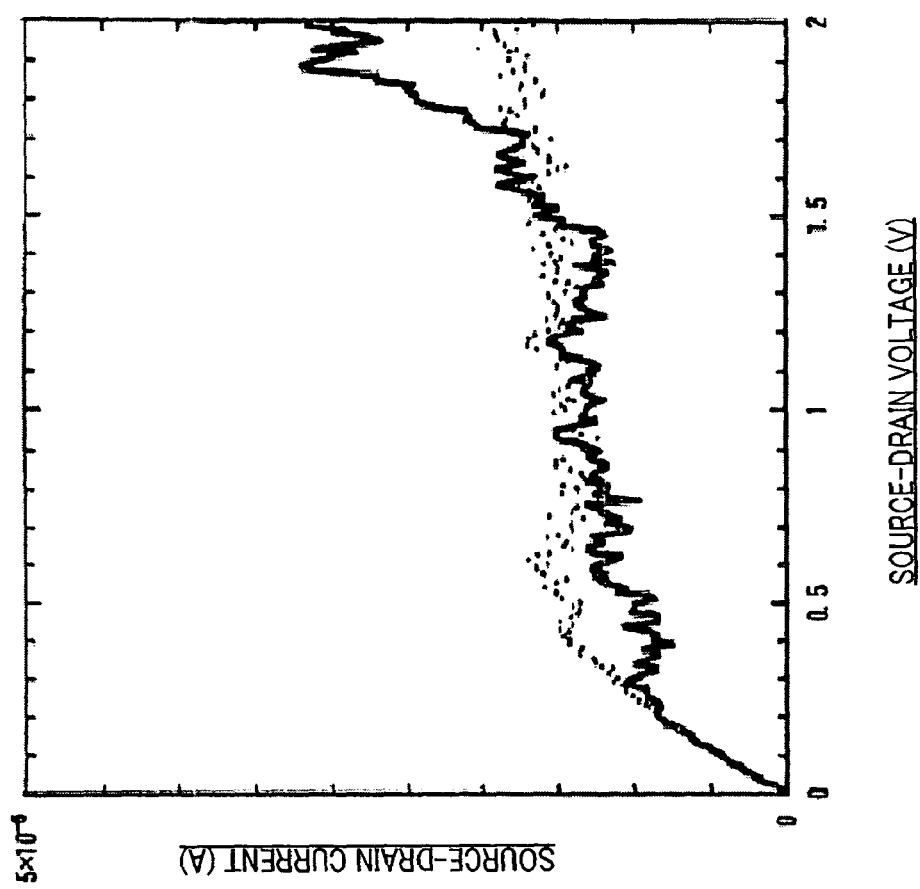

FIG. 57 is a view showing one example of I-V characteristics curve at anti-HA antibody detection by the biosensor according to the present invention.

Figure 58:
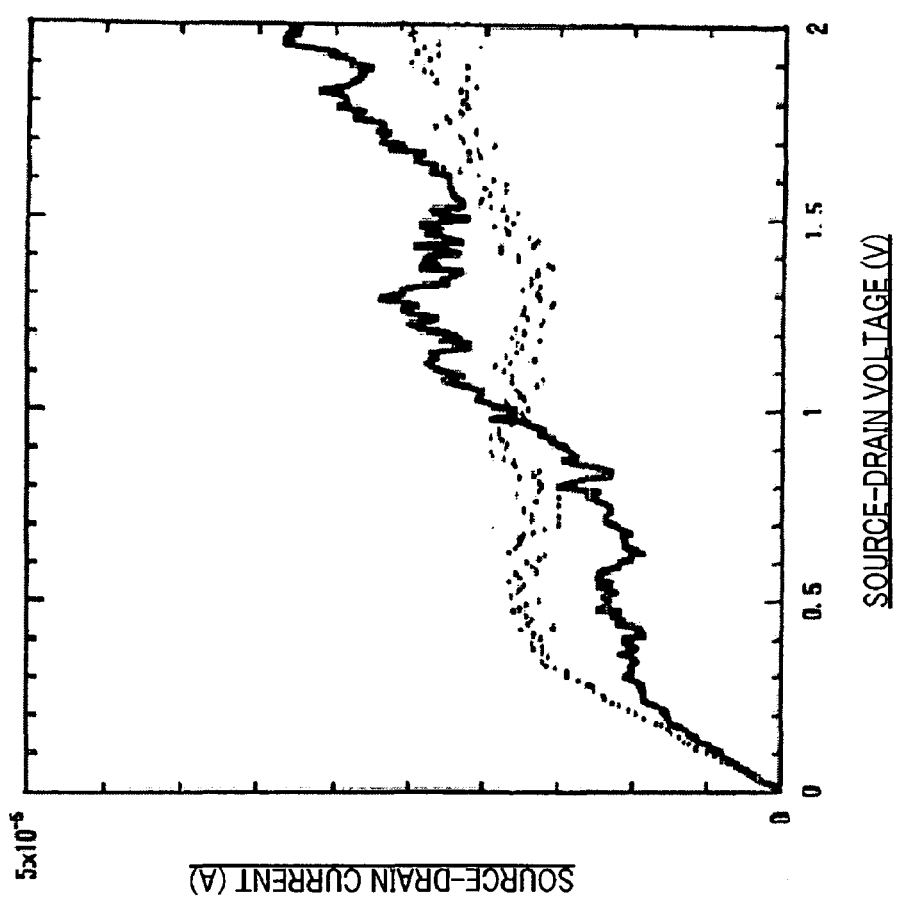

FIG. 58 is a view showing another example of I-V characteristics curve at anti-HA antibody detection by the biosensor according to the present invention.

Figure 59:
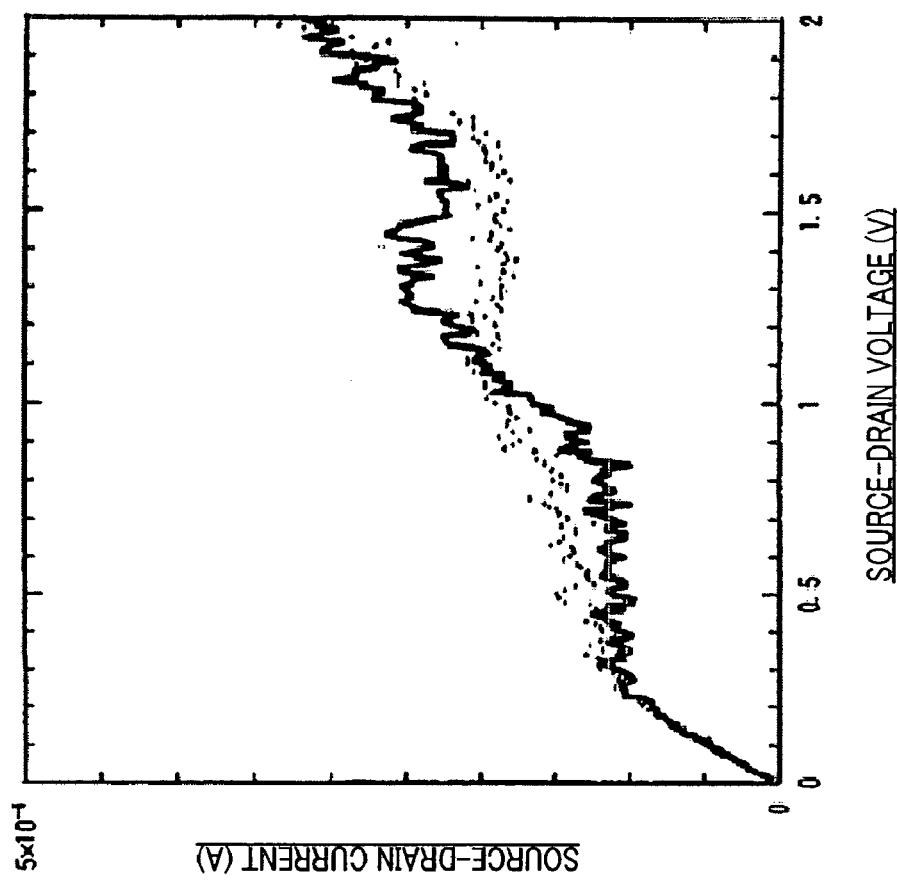

FIG. 59 is a view showing further another example of I-V characteristics curve at anti-HA antibody detection by the biosensor according to the present invention.

Figure 60:
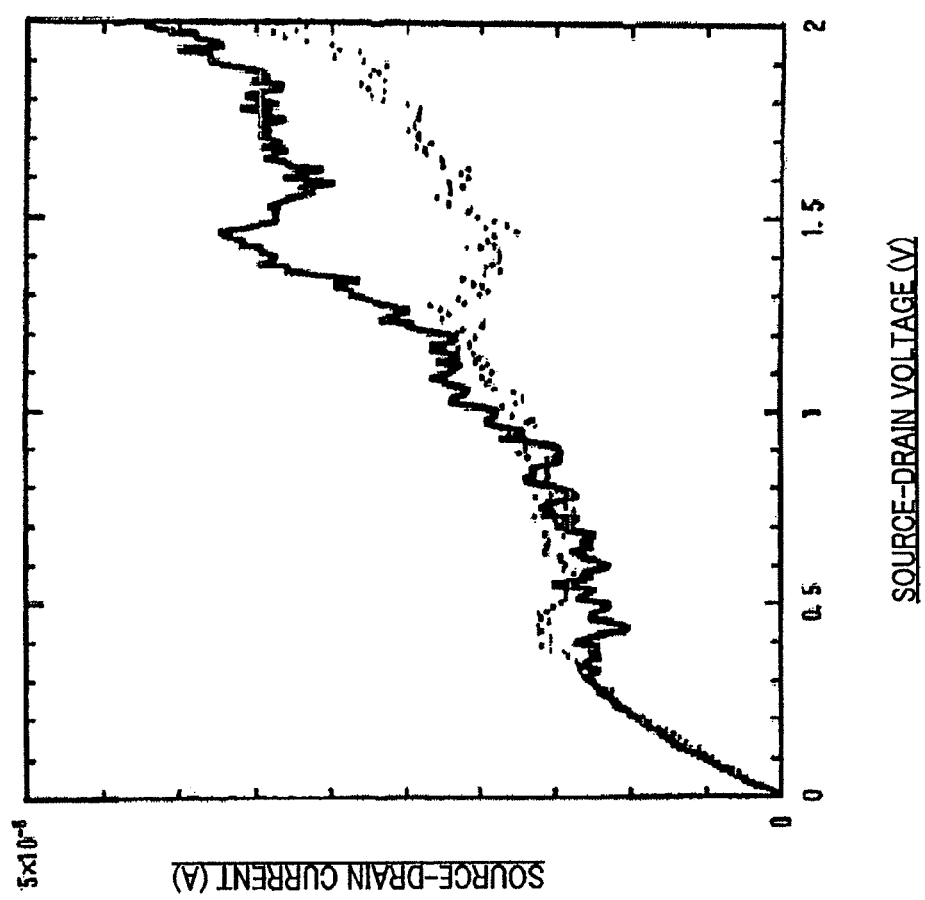

FIG. 60 is a view showing further another example of I-V characteristics curve at anti-HA antibody detection by the biosensor according to the present invention.

Figure 61:
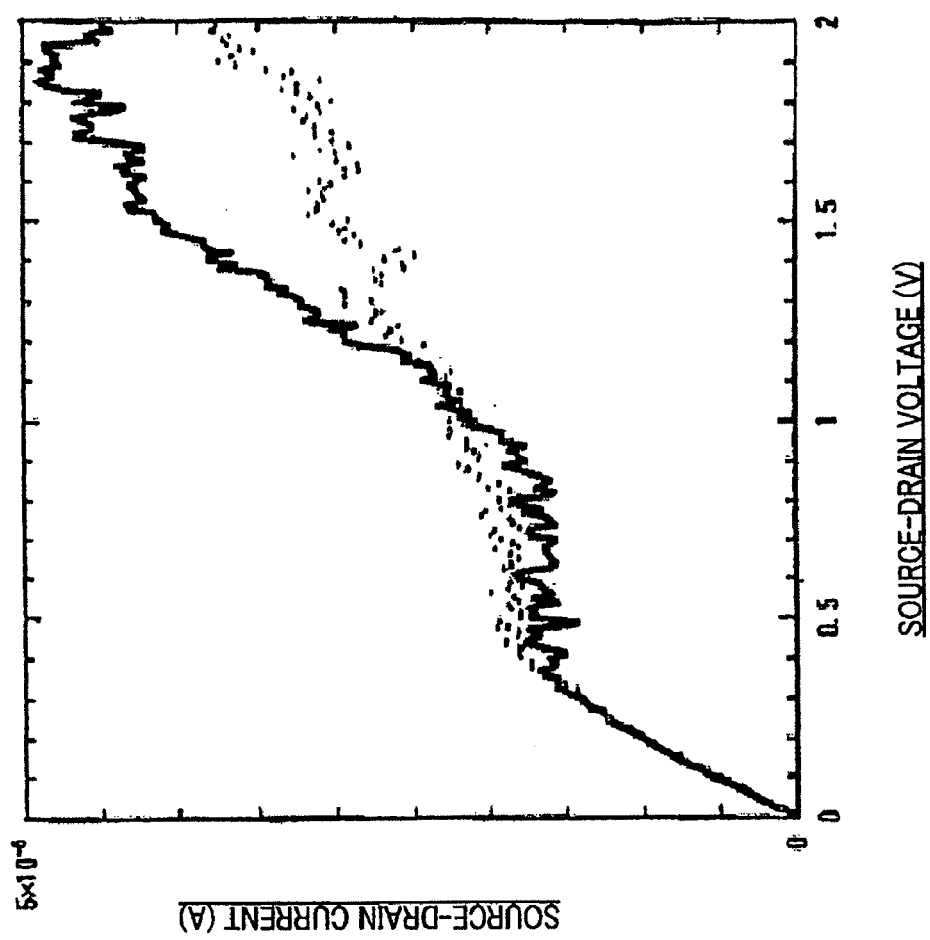

FIG. 61 is a view showing further another example of I-V characteristics curve at anti-HA antibody detection by the biosensor according to the present invention.

Figure 62:
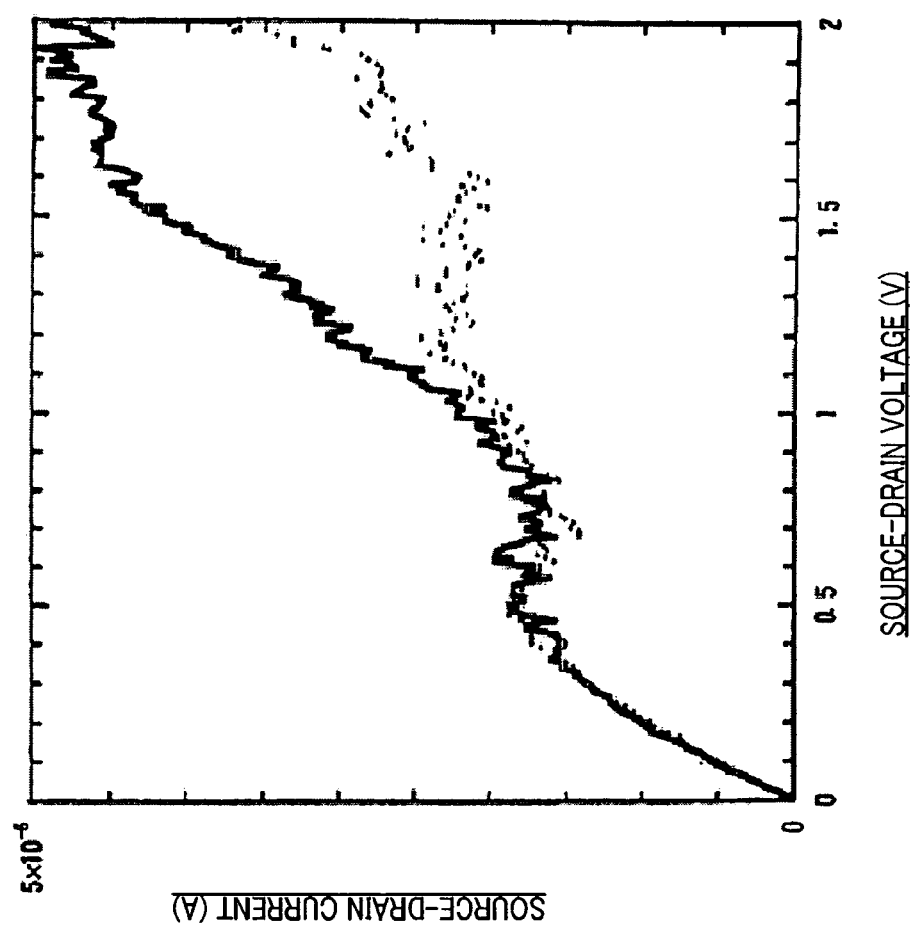

FIG. 62 is a view showing further another example of I-V characteristics curve at anti-HA antibody detection by the biosensor according to the present invention.

Figure 63:
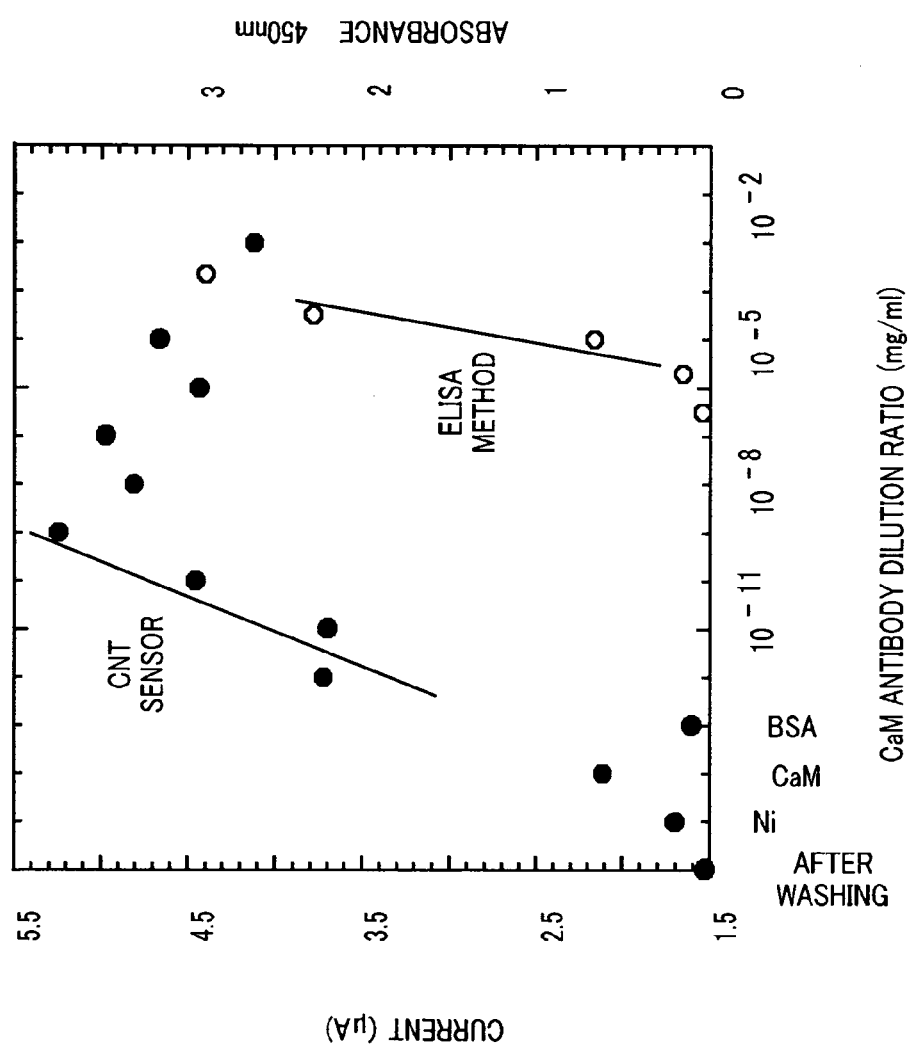

FIG. 63 is a characteristic diagram showing relationship between dilution ratio of anti-CaM antibody and current value at anti-CaM antibody detection by the biosensor according to the present invention.

Figure 64:
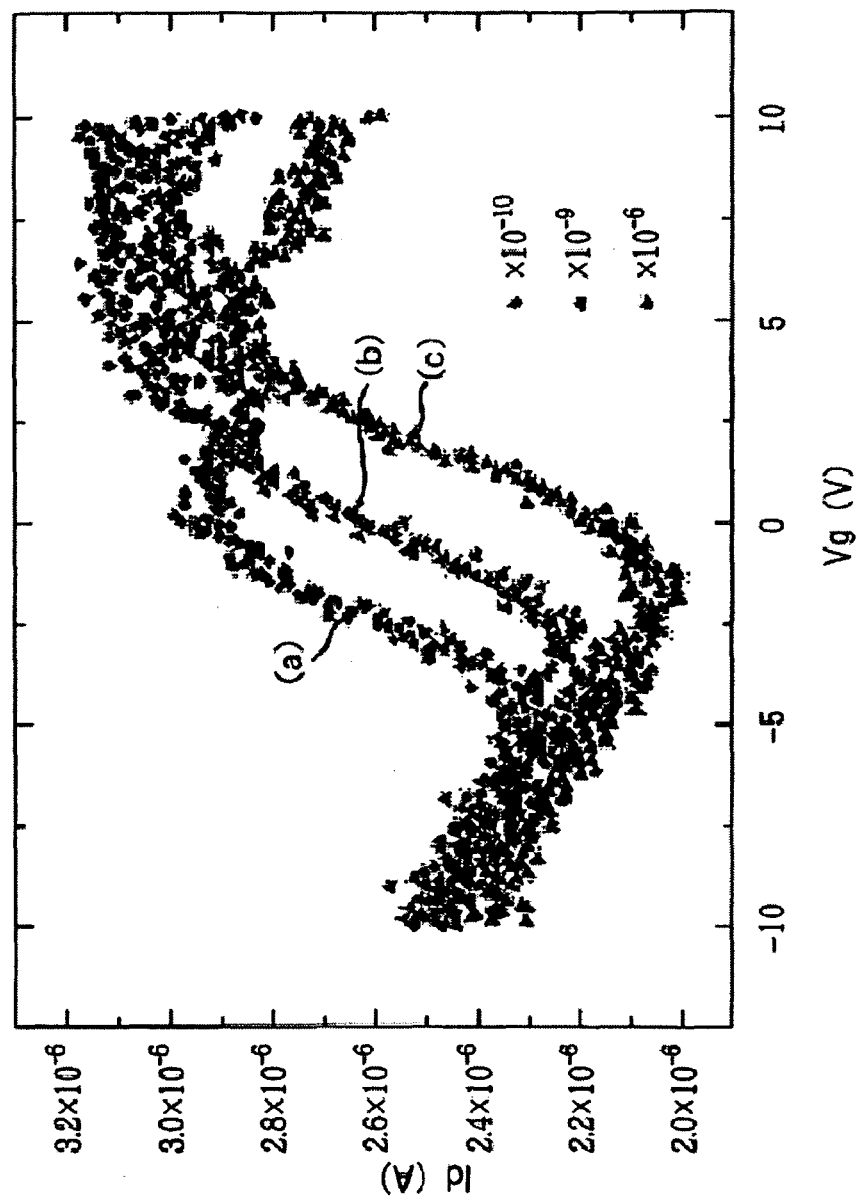

FIG. 64 is a view showing Id-Vg characteristics when concentration of anti-CaM antibody is varied.

Figure 65:
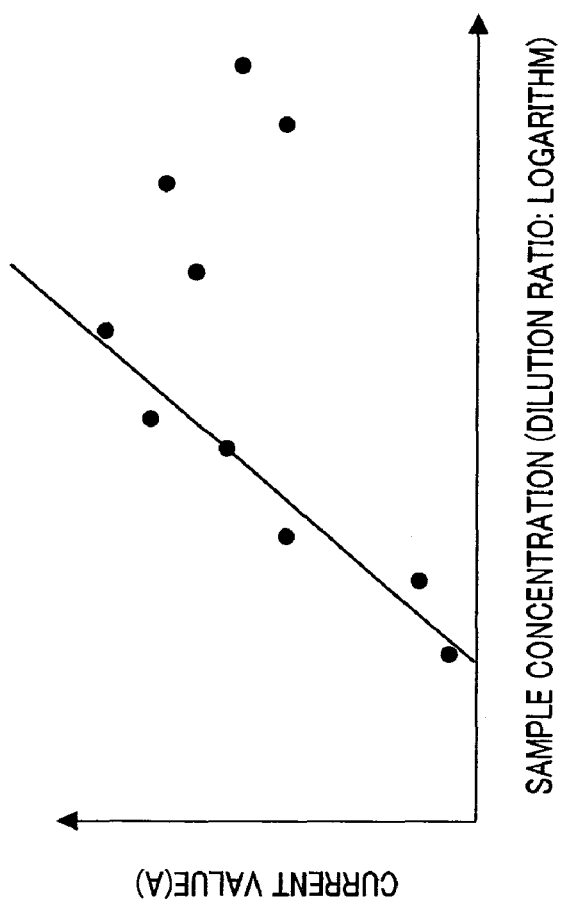

FIG. 65 is a view showing an example of a calibration curve obtained by the biosensor according to the present invention.

Figure 66A:
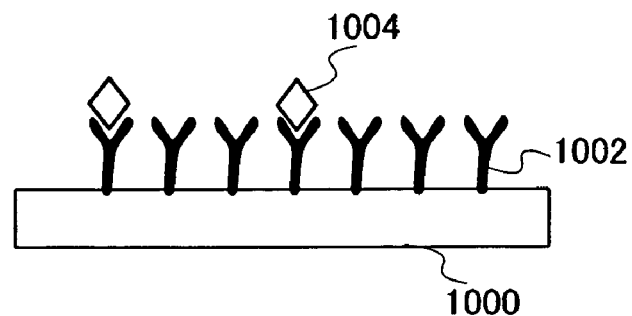
Figure 66B:
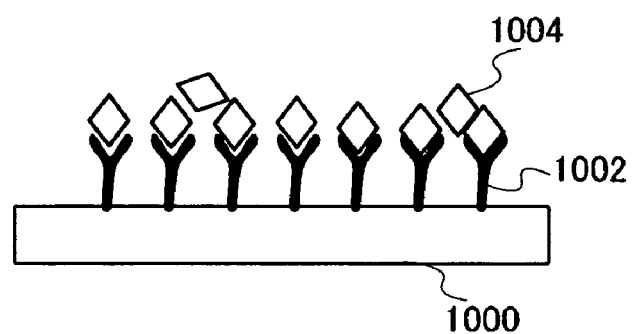

FIG. 66A is a view showing a state where the biosensor according to the present invention is ready to take measurement. FIG. 66B is a view showing a state where measurement by the biosensor according to the present invention is difficult. Reference number 1000 denotes a portion where detection target substance capturing molecule is bound, 1002 denotes detection target substance capturing molecule, and 1004 denotes detection target substance.

Figure 67:
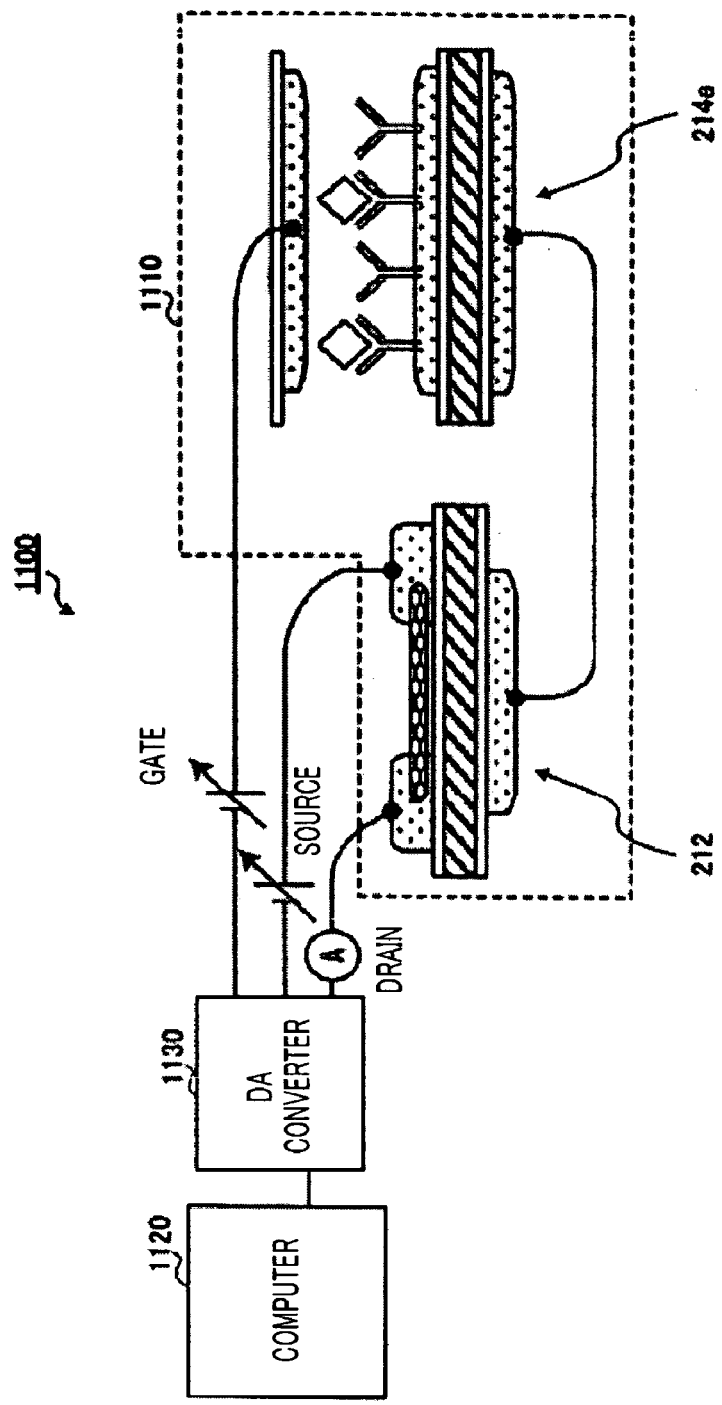

FIG. 67 is a block view showing one example of the composition of the biosensor device according to the present invention. Reference number 1100 denotes biosensor device, 1110 denotes biosensor body section, 1120 denotes computer, 1130 denotes D/A converter, 212 denotes ultra fine fiber element section, and 214*a* denotes gate element section.

Figure 68:
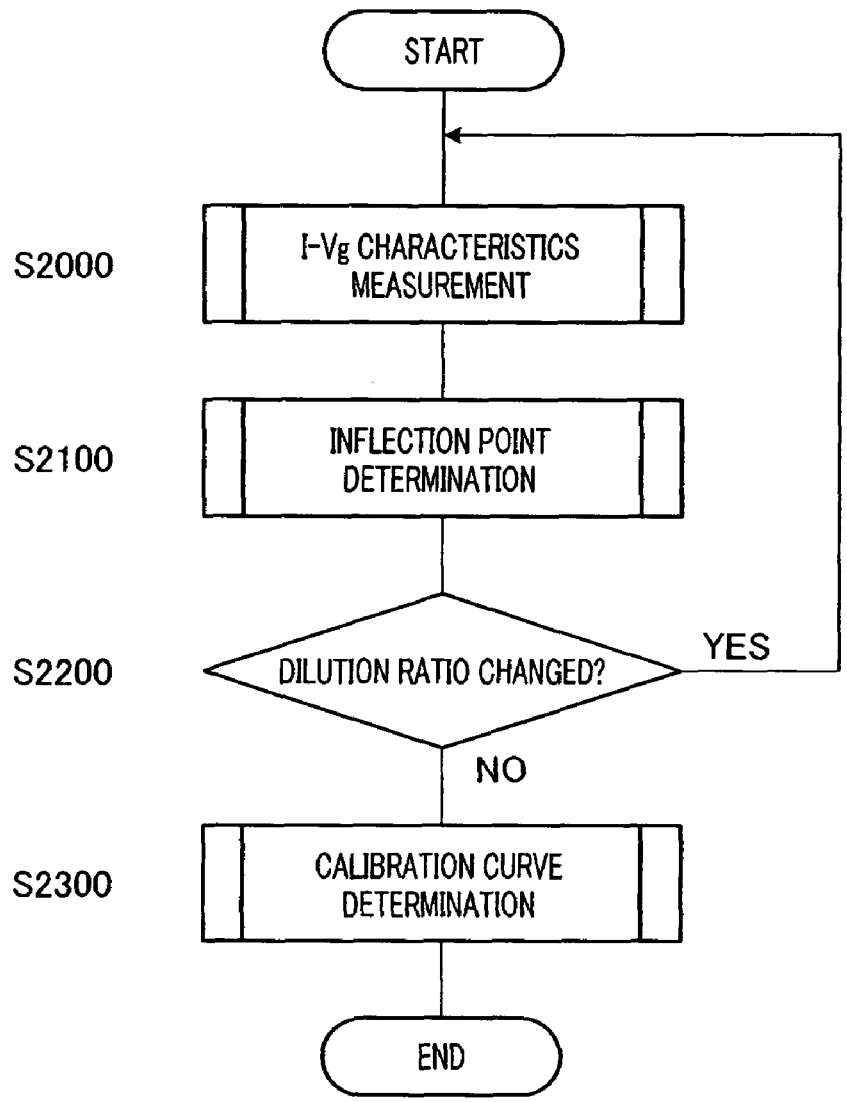

FIG. 68 is a flowchart showing one example of processing procedures of calibration function.

Figure 69:
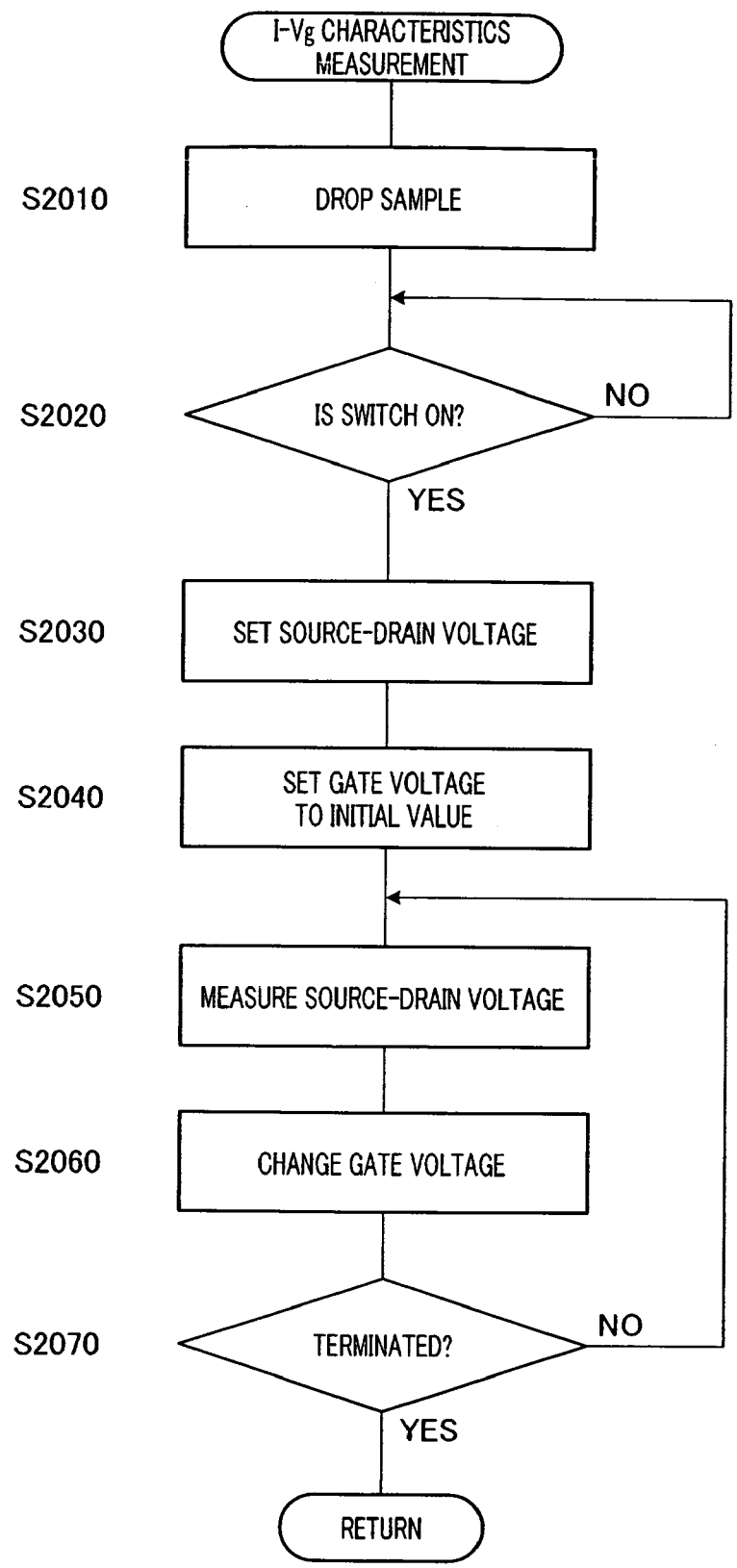

FIG. 69 is a flowchart showing processing procedures of I-Vg characteristics measurement.

Figure 70:
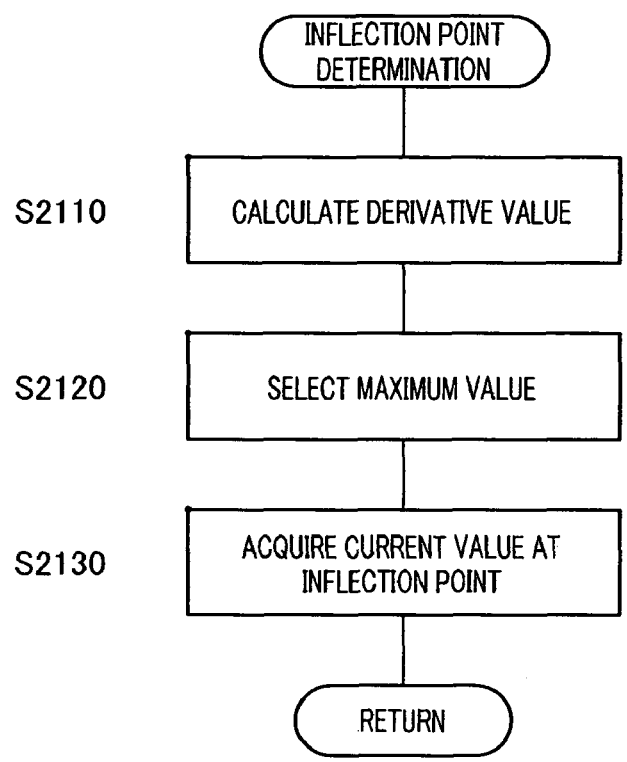

FIG. 70 is a flowchart showing processing procedures of inflection point determination.

Figure 71:
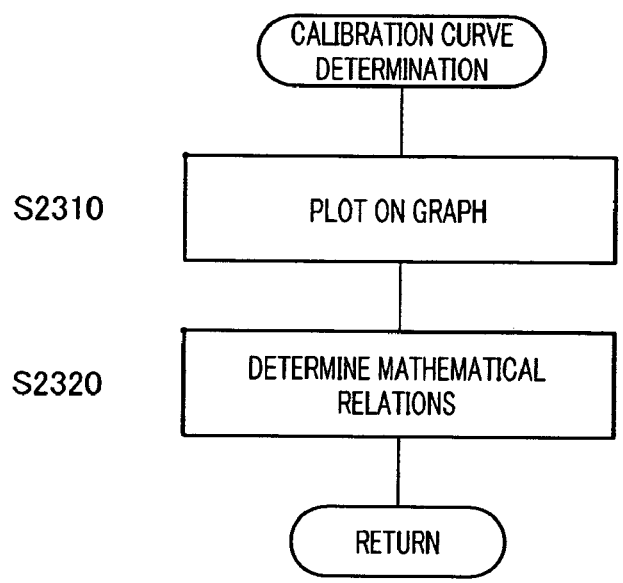

FIG. 71 is a flowchart showing processing procedures of calibration curve determination.

Figure 72B:
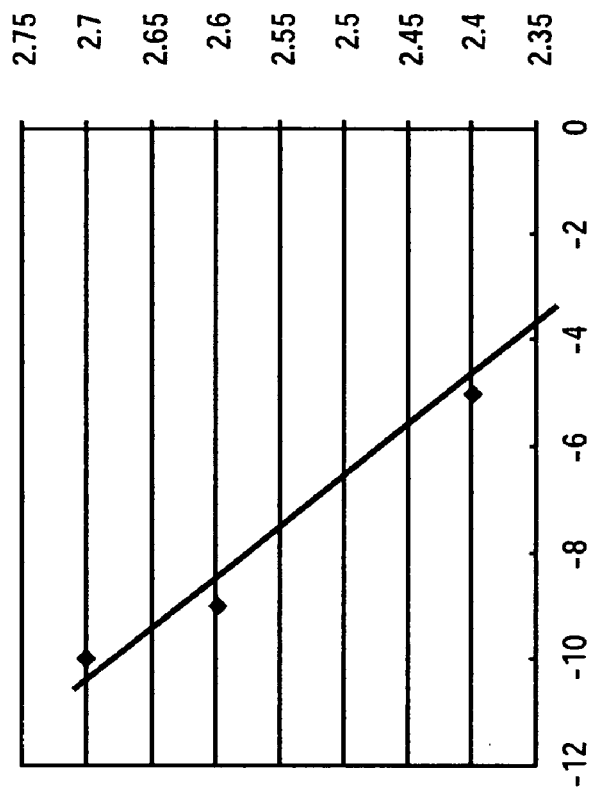
Figure 72A:
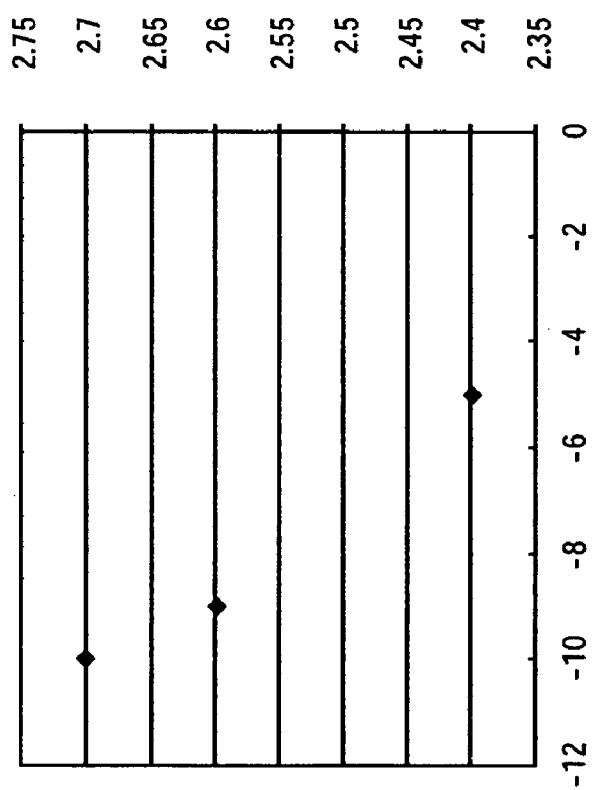

FIG. 72A is a view showing data obtained from I-Vg characteristics shown in FIG. 64 are plotted on a graph.

FIG. 72B is a view showing a straight line obtained by least square method is drawn on the graph shown in FIG. 72A.

Figure 73:
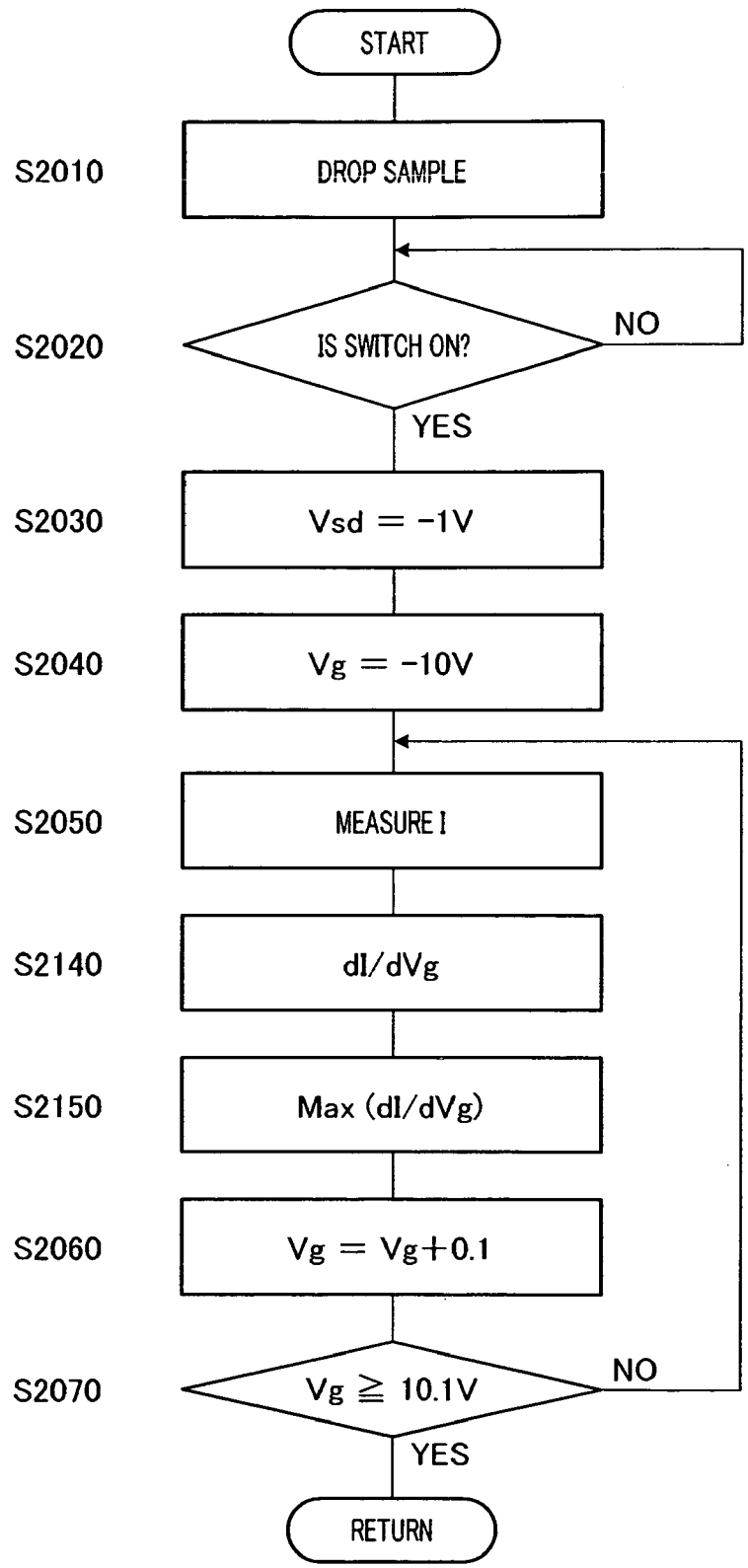

FIG. 73 is a flowchart showing one example of alteration of processing procedures of calibration function.

Figure 74:
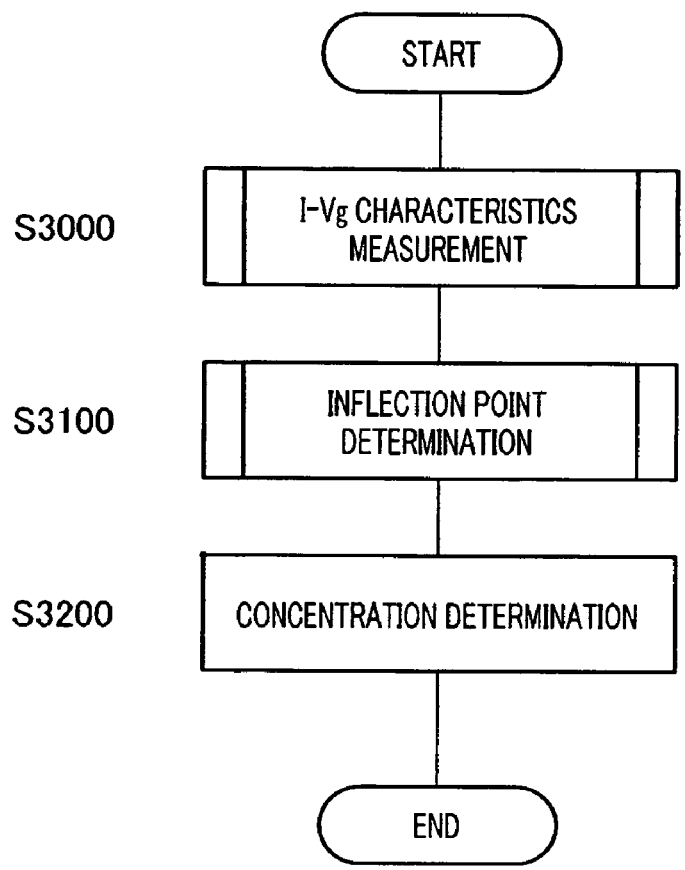

FIG. 74 is a flowchart showing one example of processing procedures of measurement function which the biosensor according to the present invention has.

BEST MODE FOR CARRYING OUT THE INVENTION

1. Field Effect Transistor of the Present Invention

FET of the present invention includes a support substrate, a first insulating film covering a first plane of the support substrate, a source electrode and a drain electrode disposed on the first insulating film, an ultra fine fiber which is a channel electrically connecting the source electrode and drain electrode, and a gate electrode which causes polarization due to movement of free electrons in the substrate and controls electric current flowing ultra fine fiber.

Figure 1A:
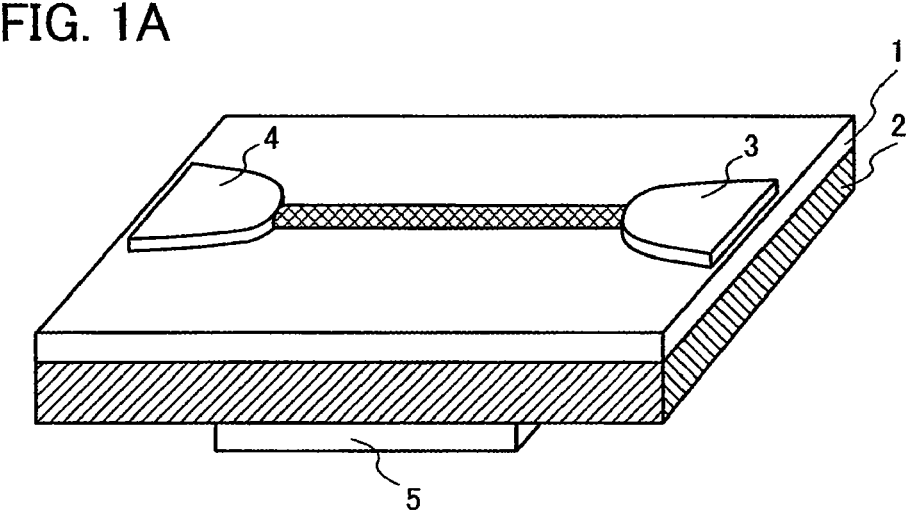
FIG. 1A is a schematic view of a conventional back-gate FET.
Figure 1B:
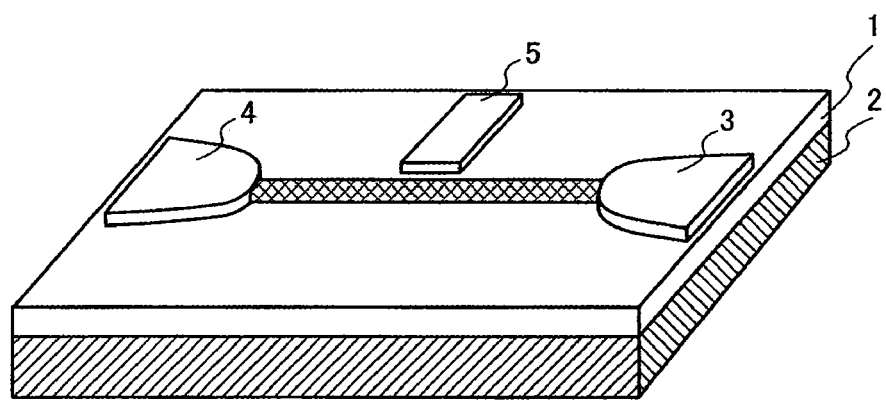
FIG. 1B is a schematic view of a conventional side-gate FET. Reference number 1 denotes insulating film, 2 denotes substrate, 3 denotes source electrode, 4 denotes drain electrode, and 5 denotes gate electrode.
Figure 2:
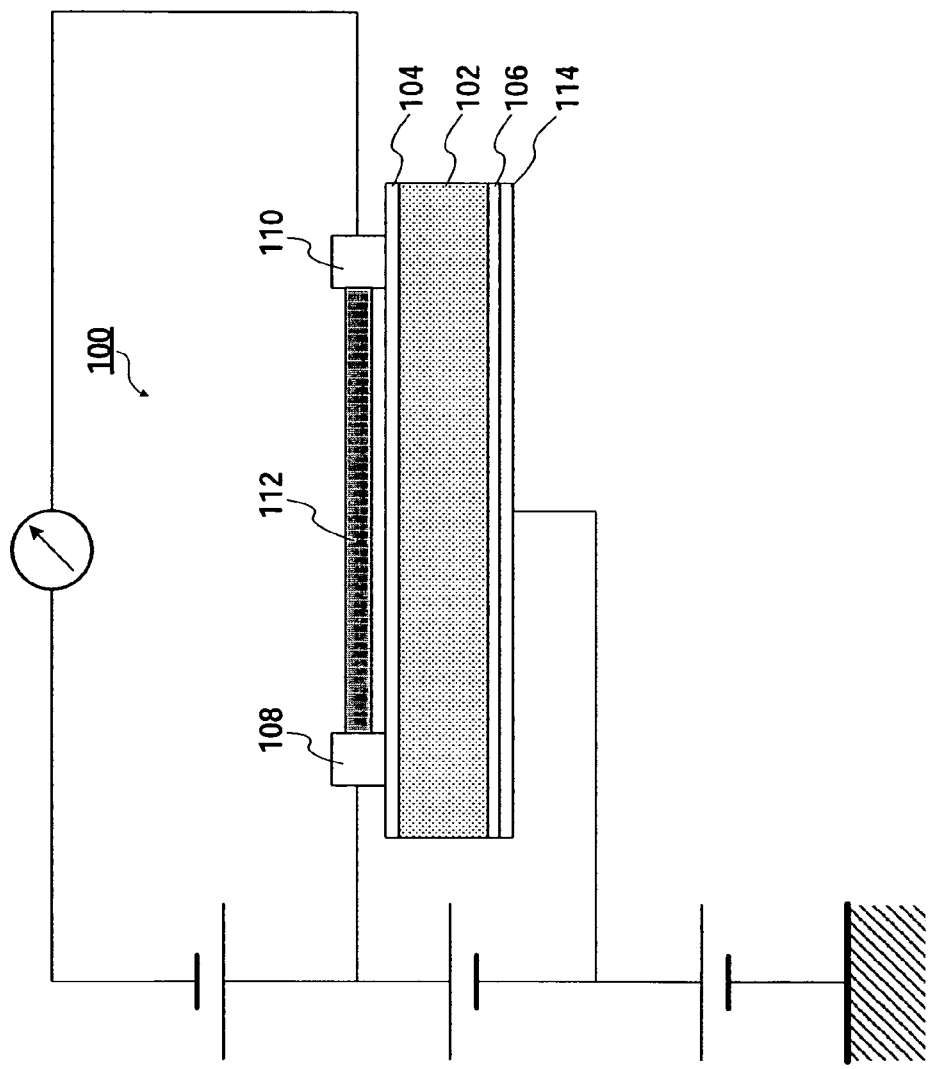
FIG. 2 is a view showing one example of back-gate FET according to the present invention. Reference number 100 denotes back-gate FET according to the present invention, 102 denotes support substrate, 104 denotes first insulating film, 106 denotes second insulating film, 108 denotes source electrode, 110 denotes drain electrode, 112 denotes ultra fine fiber, and 114 denotes gate electrode.

A first example of FET of the present invention includes a support substrate, a first insulating film covering a first plane of the support substrate, a source electrode and a drain electrode disposed on the first insulating film, an ultra fine fiber which is a channel electrically connecting the source electrode and drain electrode, a second insulating film covering a second plane of the support substrate, and a gate electrode disposed on the second insulating film. Hereafter, FET as mentioned is referred to as "back-gate FET of the present invention". An example of the back-gate FET of the present invention is shown in FIG. 2.

Figure 3:
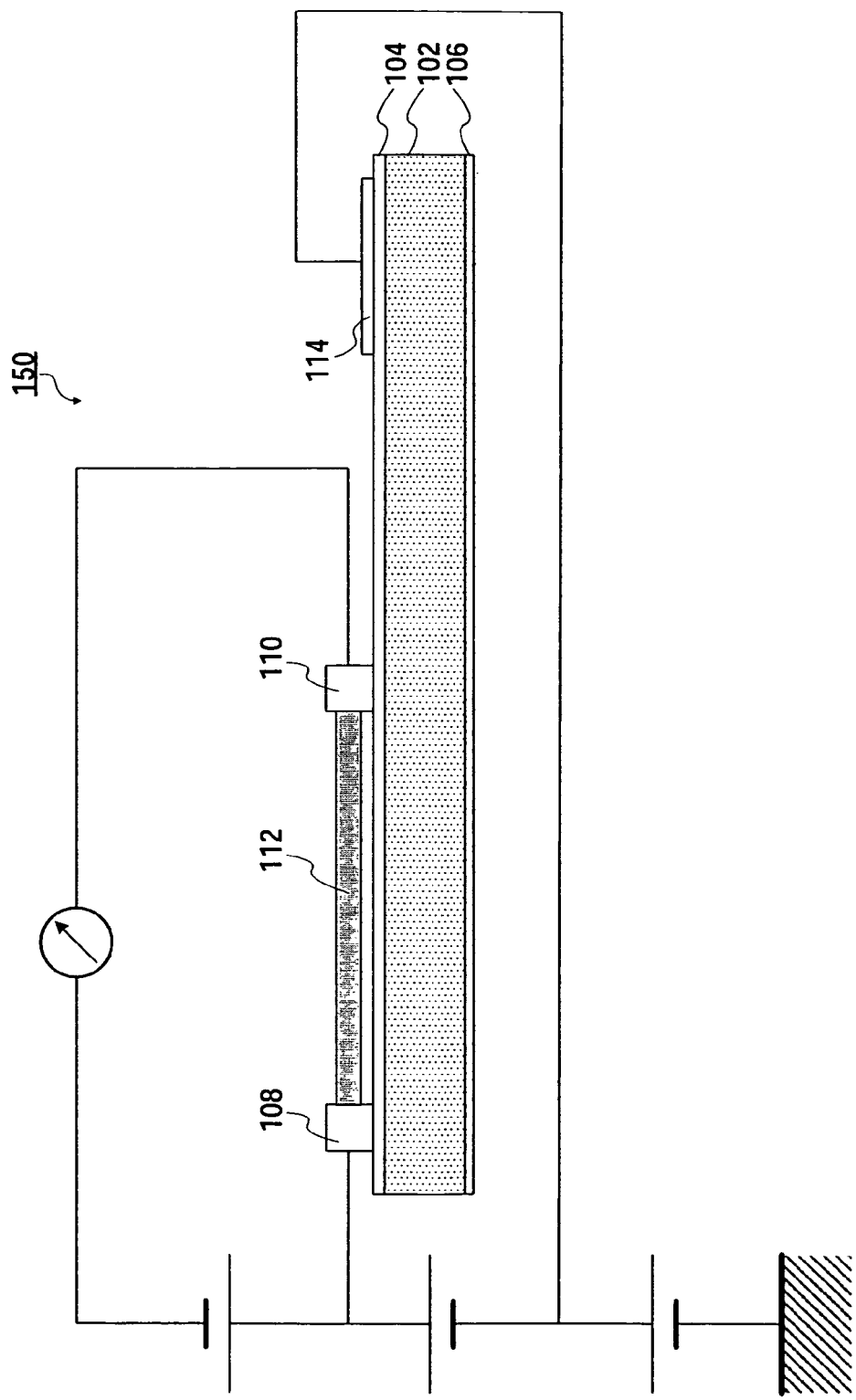
FIG. 3 is a view showing one example of side-gate FET according to the present invention. Reference number 150 denotes side-gate FET according to the present invention, 102 denotes support substrate, 104 denotes first insulating film, 106 denotes second insulating film, 108 denotes source electrode, 110 denotes drain electrode, 112 denotes ultra fine fiber, and 114 denotes gate electrode.

A second example of FET of the present invention includes a support substrate, a first insulating film covering a first plane of the support substrate, a source electrode and a drain electrode disposed on the first insulating film, an ultra fine fiber which is a channel electrically connecting the source electrode and drain electrode, and a gate electrode disposed on the first insulating film, wherein interval between the gate electrode and the ultra fine fiber is 10 μm or more. FET of the second example may further include a second insulating film covering a second plane of the support substrate. Hereafter, FET as mentioned is referred to as "side-gate FET of the present invention". An example of the side-gate FET of the present invention is shown in FIG. 3.

Figure 4:
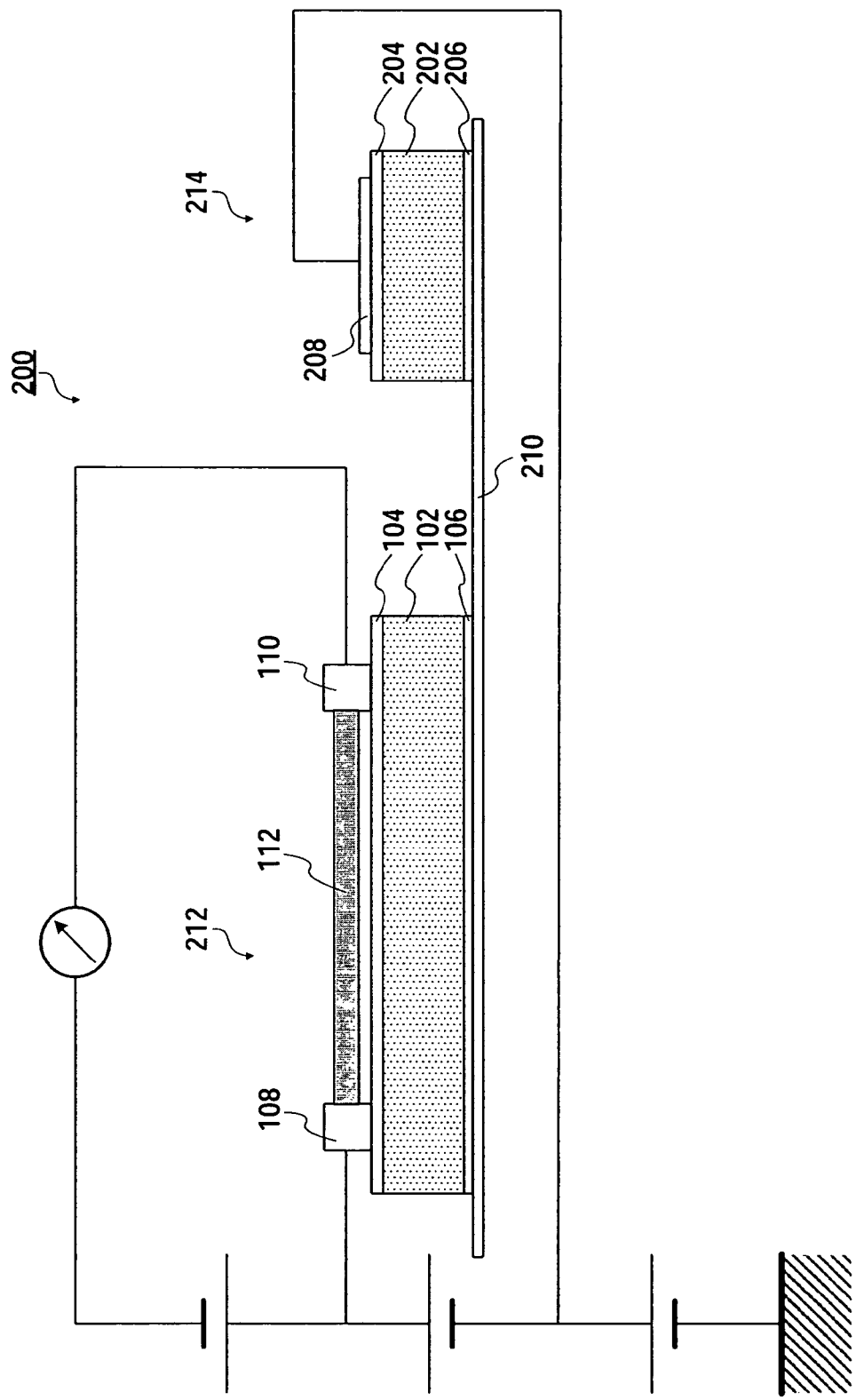

A third example of the present invention includes a support substrate, a first insulating film covering a first plane of the support substrate, a source electrode and a drain electrode disposed on the first insulating film, an ultra fine fiber which is a channel electrically connecting the source electrode and drain electrode, a second substrate which is although separated from the support substrate and first insulating film, but is electrically connected thereto, and a gate electrode disposed on the first plane of the second substrate. The gate electrode disposed on the second substrate is disposed so that polarization due to movement of free electrons may occur in the first substrate. Hereafter, FET as mentioned is referred to as "separate-gate FET of the present invention". Further, an element section including a support substrate, a first insulating film, a source electrode and a drain electrode, and an ultra fine fiber is referred to as "ultra fine fiber element section", and an element section including a second substrate and a gate electrode is referred to as "gate element section". An example of separate-gate FET is shown in FIG. 4 and FIG. 5.

1-1. Substrate

FET of the present invention has a substrate. A source electrode and a drain electrode are disposed on the substrate. The source electrode and the drain electrode are insulated by the insulating film formed on the substrate, and connected each other by an ultra fine fiber which is a channel. The structure and material of the substrate are not specifically limited as long as polarization (described later) due to movement of free electrons is caused in the substrate by applying a voltage to the gate electrode (described later). Normally, a substrate includes a support substrate composed of semiconductor or metal, and an insulating film which insulates electrically connects the support substrate and the source electrode, the drain electrode and the channel in a plane where a source electrode, a drain electrode and a channel are disposed.

An example of the substrate is shown in FIG. 6. The substrate shown in FIG. 6A includes support substrate 400 and first insulating film 402. The substrate shown in FIG. 6B includes support substrate 400, first insulating film 402, and second insulating film 404.

The support substrate is preferably a semiconductor or a metal. The semiconductor is not specifically limited, while, for example, group 14 elements such as silicon, germanium, III-V compound such as gallium arsenide, indium phosphide, II-VI compound such as zinc telluride are mentioned. Although the metal is not specifically limited, for example, aluminum and nickel are mentioned. Although the thickness of the support substrate is not specifically limited, preferably from 0.1 to 1.0 mm, more preferably from 0.3 to 0.5 mm.

The material of the first insulating film formed on the first plane (the plane on which source electrode, drain electrode and channel are disposed) of the support substrate is not limited, for example, inorganic compound such as silicon oxide, silicon nitride, aluminum oxide, titanium oxide, organic compound such as acrylic resin, polyimide are mentioned. On the surface of the first insulating film, functional group such as hydroxy group, amino group or carboxyl group may be introduced.

Although the thickness of the first insulating film is not specifically limited, preferably from 10 to 1000 nm, more preferably from 20 to 500 nm. It is possible tunnel current may be introduced if the first insulating film is too thin. Meanwhile, if the first insulating film is too thick, it is possible controlling the source-drain current using gate electrode may become difficult.

The material of the second insulating film formed on the second plane (reverse side of the first plane) is similar to the example of material of the first insulating film. Although the thickness of the second insulating film is not specifically limited, likewise first insulating film, preferably 10 nm or more, more preferably 20 nm or more. In the meantime, with back-gate FET or separate-gate FET, although the thickness of the second insulating film is not specifically limited, preferably 1000 nm or less, more preferably 500 nm or less.

The plane covered by the insulating film of the support substrate (first plane or second plane) is preferably smooth. In other words, interface between the support substrate and insulating film is preferably smooth. This is because if the surface of support substrate is smooth, reliability of the insulating film which covers the surface thereof is improved. Although a plane covered by the insulating film of the support substrate is not specifically limited, it is preferably polished. Smoothness of the surface of support substrate can be confirmed by a surface roughness measuring instrument.

1-2. Source Electrode and Drain Electrode

The source electrode and drain electrode are disposed on the first insulating film. Although the material of the source electrode and drain electrode is not specifically limited, for example, metals such as gold, platinum, titanium are mentioned. The source electrode and drain electrode are formed by depositing these metals on the first insulating film. The source electrode and drain electrode may be configured to have multilayer structure composed of two or more than two metals. For example, a gold layer may be overlaid on a titanium layer. When depositing a metal, a pattern is preferably copied in advance by lithography.

Although interval between the source electrode and drain electrode is not specifically limited, it may be normally from 2 to 10 μm. This interval may be shortened further to allow easy connection between electrodes by the ultra fine fiber.

FET of the present invention is applicable to biosensors. As one embodiment, a detection target substance capturing molecule is, in some cases, caused to be bound to an ultra fine fiber which connects the source electrode and drain electrode. On this occasion, a sample solution containing the detection target substance is, in some cases, added on the source electrode, drain electrode, and channel. When source electrode 3 and drain electrode 4 are covered by sample solution 28 added as shown in FIG. 7, a film is formed between probe of current measurement device (e.g., prober) and electrode, and accurate measurement of source-drain current is not possible in some cases.

Therefore, the source electrode and drain electrode in FET of the present invention are preferably arranged so as not to be covered wholly by the sample solution added. For example, one idea is to increase area of the source electrode and drain electrode occupying the substrate surface. For example, as shown in FIG. 8 and FIG. 9, length L of both electrodes is designed to be 500 μm or more, width W1 at the tip of both electrodes to be approximately 10 μm, and width W2 of the body of both electrodes to be approximately 150 μm. For detection of the detection target substance, probe of the measuring device is touched to a portion of the source electrode and drain electrode which is not covered by the sample solution 28.

1-3. Ultra Fine Fiber

The source electrode and drain electrode disposed on the first insulating film are electrically connected by the ultra fine fiber. The ultra fine fiber, which connects the source electrode and drain electrode, serves as a channel.

The ultra fine fiber is a fiber body having electric conducting property and is several nm in diameter. Although the ultra fine fiber is not specifically limited, for example, CNT, DNA, conductive polymer, silicone fiber, silicone whisker, grapheme, or the like are mentioned. Among them, CNT is preferable.

The ultra fine fiber which connects the source electrode and drain electrode may be single or multiple. Status of the ultra fine fiber which connects the source electrode and drain electrode can be confirmed by AFM. A gap may be present between the ultra fine fiber and substrate.

When ultra fine fiber is CNT, although CNT may be either single-walled CNT or multi-walled CNT, single-walled CNT is preferred. Further, CNT in which a defect is incorporated may be used. "Defect" denotes such a state where five-membered carbon ring or six-membered carbon ring constituting CNT is open. Actual structure of CNT incorporating a defect is not evident although it is presumed to have a structure connected barely. Although the method of introducing a defect to CNT is not specifically limited, for example, annealing of CNT is mentioned.

To prevent damage occurrence, the ultra fine fiber may be protected by an insulating protective film. Covering of the ultra fine fiber by the insulating protective film allows ultrasonic washing of whole FET, washing with the use of strong acid or strong base. Further, damage to the ultra fine fiber is prevented by providing the insulating protective film and therefore, operating life of FET can be lengthened remarkably.

With ultra fine fiber including CNT, CNT interacts easily with various molecules including water and causes changes in electron state thereof. Changes in electron state appear as changes in source-drain current, and therefore, they may act as noise source depending on aspects of sensors. Therefore, whole CNT, and part of or whole source electrode, drain electrode may be covered by the insulating protective film, as necessary. With this consideration, interaction of CNT and sample solution with vapor or the like is prevented, whereby noises can be reduced.

Although the insulating protective film is not particularly limited, for, example, a film formed by insulating adhesive agent and passivation film are mentioned. When the insulating protective film is made of silicone oxide film, detection target substance capturing molecule (e.g., antibody) can be bound easily to the insulating protective film.

FIG. 10 is a view showing one example of back-gate FET of the present invention in which ultra fine fiber is protected by insulating protective film. In FIG. 10A, whole ultra fine fiber 7612 is protected by insulating protective film 8501. In FIG. 10B, connection part between ultra fine fiber 7612 and source electrode 7610, connection part between ultra fine fiber 7612 and drain electrode 7611 are protected by insulating protective film 8501. In this case, detection target substance capturing molecule 7613 can be bound directly to ultra fine fiber 7612 (described later), and therefore, sensitivity when used as a biosensor is improved, whereby unimolecular detection is made possible. Further, by protecting contact part which is vulnerable to damages, prolongation of operating life and prevention of noises can be accomplished.

1-4. Method for Connecting Interval Between Source Electrode and Drain Electrode by Ultra Fine Fiber The source electrode and drain electrode may be electrically connected by the ultra fine fiber by arbitrary method. A method for electrically connecting the source electrode and drain electrode by the ultra fine fiber will be explained herein for a case where the ultra fine fiber includes CNT.

The method for electrically connecting the source electrode and drain electrode by CNT is not specifically limited.

For example, (A) vapor deposition method, (B) improved scattering method, or the like are mentioned.

The following description explains the method of (A) and (B).

(A) Vapor Deposition Method

Connection by the vapor deposition method is carried out according to the following procedures: (1) A catalyst is disposed at portion on a substrate where source electrode and drain electrode are scheduled to be formed. (2) CNT is produced by placing the substrate on which catalysts are disposed under the presence of hydrocarbon gas (e.g., methane gas) that is used as raw material of CNT (on this occasion, voltage may be impressed between catalysts). (3) Electrodes are formed.

Schematic view of connection by the vapor deposition method is shown in FIG. 11. In FIG. 11, reference number 1 denotes support substrate, 2 denotes first insulating film, 9a and 9b denote catalytic layer made of iron or the like, 10 denotes reaction chamber, and 11 denotes hydrocarbon gas to be used as raw material of CNT. Temperature at reaction may be from 700 to 900° C. Desired CNT 7 can be formed by adjusting appropriately material and shape of the catalyst, voltage impressed, type and volume of hydrocarbon gas. CNT 7 is several μm in length (e.g., about 3 μm) and several nm in diameter, and has ultra fine fibrous structure.

Although the method for disposing the catalysts at portion where the source electrode and drain electrode are scheduled to be formed is not specifically limited, for example, a metal may be vapor-deposited by electron beam lithography. Catalyst is a metal to become growth nuclei of CNT. Although the metal to become catalyst is not specifically limited, for example, transition metals such as iron, nickel, cobalt, molybdenum, tungsten are mentioned.

FIG. 12 is a view showing one example for connecting interval between catalysts by vapor deposition method. Reference number 1 denotes first insulating film, 9a and 9b denote catalyst, 22a and 22b denote source electrode and drain electrode to be formed later, and 7 denotes CNT formed. In this way, a pair of catalysts 9a, 9b is disposed on the substrate at a predetermined interval, CNT is caused to grow from catalyst 9a and catalyst 9b, and both are connected.

FIG. 13 is a view showing one embodiment of structure of the catalyst disposed on the substrate in the vapor deposition method. As shown in FIG. 13, catalyst 9 may take three-layer structure including support layer 25, middle layer 26, and top layer 27. Support layer 25 is made of silicone or the like and may have thickness of approximately 50 nm. Middle layer 26 is made of transition metals such as molybdenum, tantalum, tungsten, and may have thickness of approximately 10 nm. Top layer 27 is made of transition metals such as iron, nickel, cobalt, and may have thickness of approximately 3 nm. Total height H of catalyst 9 may be approximately 63 nm, and diameter D may be approximately 2 μm. Catalyst 9 of three-layer structure may be formed using film forming technology such as vapor deposition, sputtering, ion plating.

FIG. 14 is a view showing another embodiment for connecting interval between catalysts by vapor deposition method. In this example, a plurality of catalysts 9a-1, 9a-2, . . . 9a-n and 9b-1, 9b-2, . . . 9b-n opposed thereto are formed at portions where source electrode 22a and drain electrode 22b are scheduled to be formed. In this way, by providing a plurality of catalyst pairs thickly to allow growth of CNT 7, connection of catalyst 9a and catalyst 9b is made much easier.

FIG. 15 is a view showing arrangement of example of catalyst 9a and catalyst 9b in the embodiment shown in FIG. 14. Although distance L1, an interval between adjacent catalysts (e.g., interval between 9a-1 and 9a-2) is not specifically limited, it may be approximately 2 μm. Further, although distance L2 between rows of catalysts (interval between row of 9a-1, 9a-2, . . . 9a-n and row of 9b-1, 9b-2, . . . 9b-n) is not specifically limited, it may be approximately 4 μm.

Structure, number of pieces and position of arrangement act as important factors for connecting the interval between electrodes by CNT. For example, to improve connection rate between electrode pairs, the number of catalysts per portion where a pair of electrodes are scheduled to be formed is simply increased. Further, to improve yield rate of conductivity (rate of electrode pairs having conductivity to present on one substrate), the number of electrode pairs per one substrate is simply increased.

Size of the electrode (this relates to number of catalysts per portion where a pair of electrode is scheduled to be formed) and number of electrode pairs are limited by size of the substrate and restrictions on manufacturing technology. According to the preliminary experiment carried out by the present inventors, yield rate of conductivity could be improved from 20% level to maximum 87.5%, while the number of electrode pairs per one substrate was set to 24 pairs, and the number of catalysts per portion where one electrode was scheduled to be formed was increased from one piece to three pieces. The number of electrode pairs and the number of catalysts as mentioned can be attained within stable control limit of ordinary lithography.

Procedures for connecting an interval between electrodes by CNT by vapor deposition method will be explained hereafter in greater detail.

First, a substrate on which are disposed catalysts is heated in a reaction chamber from room temperature to 900° C. for 15 minutes. During heating, argon gas is introduced to the reaction chamber at 1000 sccm (gas flow rate per one minute). Upon completion of heating, methane at the flow rate of 1000 sccm and hydrogen at 500 sccm are introduced while the temperature is maintained at 900° C. Following this, it is cooled to room temperature over 120 minutes, and argon is introduced to the reaction chamber at the flow rate of 1000 sccm during cooling.

After an interval between catalysts is connected by CNT, a source electrode and drain electrode are formed by vapor deposition or the like. The electrode can be formed by direct vapor deposition of a target metal such as gold onto the substrate, or other metal such as titanium is vapor-deposited and then its surface is covered by target metal such as gold. According to the forming by the latter, peeling of electrode from substrate and crack generation can be suppressed. Width of the electrode may be approximately 10 μm.

Meanwhile, vapor deposition method may be combined with improved scattering method which will be described later. That is, such a connection may be made that after interval between electrodes is connected by CNT by vapor deposition method, CNT prepared separately may be further provided on the substrate to ensure the connection (improvement of yield rate of conductivity).

FIG. 16 is a schematic view (birds-eye view) for explanation of connection by combination of vapor deposition method and improved scattering method. In FIG. 16A, reference number 3 and 4 denote source electrode and drain electrode, 44 denotes CNT formed (grown) by the vapor deposition method. In FIG. 16B, it is shown that CNT 43 presented by the improved scattering method connects CNTs 44 formed by the vapor deposition method.

(B) Improved Scattering Method

Connection by the improved scattering method is performed by providing CNT prepared separately on the substrate where source electrode and drain electrode are disposed or to be disposed. Commercially available CNT may be used for separately prepared CNT. Further, high-quality CNT prepared by arc discharge (those with fewer defects) may be used.

Different from the vapor deposition method, this method does not require high-temperature conditions (e.g., from 800 to 900° C.) and therefore, preparation of an expensive growth reactor is unnecessary and choice of materials of substrate is widened (e.g., glass may be used).

However, with random arrangement of CNT on the substrate, whether or not connection is made depends on coincidence and controls are difficult. So, for connection by the improved scattering method, CNT affinity substance is preferably used. Specifically, portion on the substrate where electrode is scheduled to be formed is modified by CNT affinity substance, or electrode formed on the substrate is modified by CNT affinity substance, or CNT before presentation is modified by CNT affinity substance. CNT affinity substance binds to CNT and also binds to the substrate or electrode, it is possible to immobilize CNT to the substrate or electrode. Connection by the improved scattering method using CNT affinity substance can improve yield rate in terms of conductivity.

Although CNT affinity substance is not specifically limited, for example, polycyclic aromatic molecule which exhibits π-π interaction with CNT are mentioned. Although polycyclic aromatic molecule is not specifically limited, for example, aromatic hydrocarbon such as pyrene, naphthalene, anthracene, phenanthrene, and aromatic heterocyclic compound are mentioned. For aromatic polycyclic molecule, pyrene is preferable.

Further, CNT affinity substance may be molecule having not less than two aromatic function groups. The CNT affinity substance having not less than two aromatic function groups improves van der Waals force with CNT and therefore, is able to immobilize CNT with stable manner. In addition, CNT affinity substance having not less than two aromatic function groups is able to selectively immobilize CNT having a desired diameter in accordance with an angle between two functional groups. FIG. 17 is a view to explain that a molecule having two aromatic functional groups (bond angle between two functional groups is θ) immobilizes CNT 45a, but does not immobilize CNT 45b having greater diameter. Although molecule having not less than two aromatic function groups is not specifically limited, for example, such one that bridges bimolecular pyrene via lysine is mentioned.

Further, CNT affinity substance, in which functional group is introduced for binding to substrate surface or source electrode and drain electrode surface, is preferably used. For example, when amino group is present on substrate surface or electrode surface, it is preferable that carboxyl group or ester group is introduced to CNT affinity substance. When carboxyl group is present on the substrate or electrode surface, it is preferable that amino group is introduced to CNT affinity substance. Although CNT affinity substance to which carboxyl group is introduced is not specifically limited, for example, 1-pyrenebutyric acid is mentioned. Although CNT affinity substance to which ester group is introduced is not specifically limited, for example, 1-pyrenebutyric acid N-hydroxysuccinimide ester is mentioned. Although CNT affinity substance to which ester group is introduced is not specifically limited, for example, 1-pyrenemethylamine is mentioned.

Although a method for introducing carboxyl group to substrate surface is not specifically limited, for example, such a method may be used that substrate surface is treated by silane coupling agent containing functional group that can be converted to carboxyl group, and this functional group is converted to carboxyl group. Besides, although a method for introducing amino group to the substrate is not specifically limited, for example, substrate surface may be treated by aminosilane. Although aminosilane is not specifically limited, for example, 3-aminopropyltriethoxysilane (APS) is mentioned.

Although a method for introducing carboxyl group to electrode surface is not specifically limited, for example, surface of gold electrode may be treated with thiocarboxylic acid. Although thiocarboxylic acid is not specifically limited, for example, 11-mercaptoundecanoic acid is mentioned. Further, although a method for introducing amino group to electrode surface is not specifically limited, for example, surface of gold electrode may be treated with aminothiol. Although aminothiol is not specifically limited, for example, 11-amino-1-undecanthiol or the like are mentioned.

Although CNT presented in the improved scattering method may be either single-walled CNT or multi-walled CNT, single-walled CNT is preferably used. Average length of CNT to be presented is normally 0.5 μm or more, more preferably 1.0 μm or more. Although upper limit of average length is not specifically limited, it needs only to be 10 μm or less, preferably 5 μm or less, more preferably 3 μm or less. In either case, length of CNT is preferably not less than interval between the source electrode and drain electrode. Average length of CNT can be measured by AFM. CNT presented is, for example, single-walled CNT supplied by Carbon Nanotechnologies INC.

CNT presented may be acid treated one. Although acid treatment of CNT is not specifically limited, for example, CNT may be treated by sulfuric acid, nitric acid, or mixture thereof, and may be further subjected to ultrasonic washing. Carboxyl group is introduced to CNT surface by acid treatment. Hydrophilicity of CNT after acid treatment is improved, and hence its dispersibility in the water is improved. Therefore, presentation of CNT dispersed in the water becomes easier.

Connection by the improved scattering method is classified, for example, as follows:
[A] (1) Portion on the substrate where source electrode and drain electrode are scheduled to be formed is modified by CNT affinity substance, (2) CNT is presented to the modified portion where the electrode is scheduled to be formed, and (3) Source electrode and drain electrode are formed.
[B] (1) Source electrode and drain electrode are formed on substrate, (2) Source electrode and drain electrode are modified by CNT affinity substance, and (3) CNT is presented to modified source electrode and drain electrode.
[C] (1) CNT is modified by CNT affinity substance, (2) Source electrode and drain electrode are formed on the substrate, and (3) Modified CNT is presented to electrodes on the substrate.
[D] (1) CNT is modified by CNT affinity substance, (2) Modified CNT is presented to portion on the substrate where the electrode is scheduled to be formed, and (3) Source electrode and drain electrode are formed on the substrate.

In order to modify a portion where electrode is scheduled to be formed by CNT affinity substance in the embodiment of [A], for example, such a method may be used that region other than the portion on the substrate where electrode is scheduled to be formed is subjected to masking by lithography or the like, functional group (e.g., amino group) is introduced to not-masked portion where electrode is scheduled to be formed, and CNT affinity substance having functional group (e.g., ester group) capable of reacting with the functional group introduced to the portion where the electrode is scheduled to be formed is presented.

Although material of resist film is not specifically limited, for example, PMMA is mentioned. Thickness of the resist film may be from 1 μm to 3 μm.

A method for introducing amino group to a portion where electrode is scheduled to be formed is not specifically limited. For example, such a method may be used that aminosilane solution such as APS is dropped onto the portion where electrode is scheduled to be formed and it is dried. A film thus formed is a condensation product of such as APS, and its thickness may be from 1 nm to 1 μm.

CNT affinity substance can be presented being dissolved in organic solvent such as DMF. In particular, for example, a small amount of solution of CNT affinity substance dissolved in organic solvent may be added bit by bit to a solvent (e.g., aqueous solution) to which the substrate is dipped. Solvent remained on the substrate at washing after reaction is preferably removed by drying it under inert gas (this is applicable to other embodiments).

In Embodiment [A], in order to present CNT to a modified portion where electrode is scheduled to be formed, for example, dispersion solution of CNT prepared separately is presented to the portion where electrode is scheduled to be formed. In order to present the dispersion solution of CNT to the portion where electrode is scheduled to be formed, dispersion solution of CNT may be dropped on the substrate or the substrate may be dipped into dispersion solution of CNT. Although solvent of the dispersion solution is not specifically limited, for example, organic solvent such as DMF and water are mentioned. With acid treated CNT, dispersibility into water is enhanced through introduction of carboxyl group or other method. Therefore, presentation of acid treated CNT is preferably performed being dissolved into aqueous solvent. The pH of the dispersion aqueous solution is adjusted to not less than pKa of carboxyl group (approximately 4), preferably from 7 to 8.

The concentration of CNT in CNT dispersion solution is preferably from 0.001 mg/ml to 0.1 mg/ml. When the concentration is greater than 0.1 mg/ml, CNT is easily aggregated resulting in difficulty of preparation of dispersion solution.

When CNT is presented to modified portion, at least a part of it is immobilized to the substrate thereby causing connection of the source electrode and drain electrode. However, whole CNT presented is not necessarily immobilized to the portion on the substrate where electrode is scheduled to be formed. Therefore, it is preferable to remove CNT not immobilized by washing after CNT is presented and before the electrode is formed. Washing of the substrate is carried out by washing of the substrate by solvent (e.g., DMF) or ultrasonic washing of the substrate in a solvent.

In Embodiment [A], in order to form a source electrode and a drain electrode, a metal may be vapor-deposited using, for example, lithography. The electrode and channel can be integrated by welding a portion where the source electrode or drain electrode, and channel are overlapped by way of locally impressed electric field that uses high field electron beam or STM/AFM (this also applies to other cases mentioned below).

Further, in Embodiment [A], CNT on the substrate may be further vapor deposited after CNT is presented (more preferably after washing). For vapor deposition of CNT, previously mentioned treatment may be performed after a substrate to which CNT is presented is placed in a furnace for vapor deposition.

Detailed procedures of Embodiment [A] will be shown in "detailed example A" described later.

In Embodiment [B], in order to form a source electrode and a drain electrode on a substrate, a metal may be vapor-deposited using lithography.

In Embodiment [B], in order to modify a source electrode and a drain electrode by CNT affinity substance, such a method may be used that, for example, a functional group (e.g., carboxyl group or amino group) is introduced to electrode surface by forming self-assembled film on electrode surface making use of metal-thiol bond, and CNT affinity substance having a functional group (e.g., amino group or ester group) reacting with the functional group introduced to the electrode surface is presented. In order to introduce a functional group to electrode surface, for example, electrode surface may be treated by a compound (e.g., thiol carboxylic acid or amino thiol) having a functional group (e.g., thiol group) specifically reacting with electrode material.

CNT affinity substance can be presented being dissolved into organic solvent such as DMF. On this occasion, a reagent (e.g., carbodiimide) accelerating reaction between the functional group (e.g., carboxyl group) introduced to electrode and functional group of CNT affinity substance (e.g., amino group) may be used, as necessary.

In Embodiment [B], in order to present CNT to the modified source electrode and drain electrode, a dispersion solution in which CNT is dispersed in organic solvent such as DMF or water may be presented to modified portion. Likewise Embodiment [A], acid treated CNT is preferably presented being dispersed into water. Further, the dispersion solution may be added to the substrate or the substrate may be dipped into dispersion solution.

In Embodiment [B], likewise Embodiment [A], all of CNTs presented are not necessarily immobilized to the substrate. It is therefore preferable to wash the substrate after CNT presentation to remove CNT not immobilized. For washing of the substrate, for example, the substrate may be washed by solvent or subjected to ultrasonic washing in a solvent.

In Embodiment [B], after CNT is presented (more preferably after washing), an electrode is preferably formed on the electrode already formed on the substrate by further vapor-depositing a metal. Further vapor deposition of the metal after CNT presentation ensures stable flowing of an appropriate source-drain current (e.g., about from 0.1 to 1.0 µA). In addition, elements through which electric current of about from 0.1 to 1.0 VA flows are resistant to breakage even after washed several times with water or the like.

Further, in Embodiment [B], likewise Embodiment [A], CNT on the substrate may be vapor-deposited after CNT is presented (more preferably after washing).

Detailed procedures of Embodiment [B] will be shown in "detailed example B" described later.

In Embodiment [C] or [D], in order to modify CNT by CNT affinity substance, for example, CNT may be added to a solution containing CNT affinity substance (solvent is ethanol). When CNT is modified by CNT affinity substance, whole surface of CNT can be covered by CNT affinity substance. When CNT is treated by pyrene that is one example of CNT affinity substance to add hydrophilicity, dispersibility of CNT in aqueous solution is improved, whereby CNT can be dispersed more uniformly on the substrate.

In Embodiment [C], CNT affinity substance for modifying CNT preferably has functional group to allow binding to electrode surface. For example, when carboxyl group is introduced to electrode surface, CNT may be modified by CNT affinity substance to which amino acid is introduced.

In Embodiment [D], CNT affinity substance for modifying CNT preferably has a functional group binding to substrate surface (preferably a portion where electrode is scheduled to be formed). For example, when carboxyl group is introduced to substrate surface, CNT may be modified by CNT affinity substance to which amino acid is introduced.

In Embodiment [C] or [D], in order to present modified CNT to the substrate or electrode, dispersion solution of CNT may be dropped onto the substrate or electrode, or the substrate may be dipped into dispersion solution of CNT. Further, in Embodiment [C] or [D], likewise Embodiment [A], it is preferable to remove CNT not immobilized by washing of the substrate after CNT is presented, or CNT on the substrate may be vapor-deposited. Further, in Embodiment [C], likewise Embodiment [B], after CNT is presented (more preferably after washing), an electrode is preferably formed on the electrode already formed on the substrate by further vapor-depositing a metal.

Detailed procedures of Embodiments [C] and [D] will be shown in "detailed example C" and "detailed example D" described later.

Detailed Example A of Improved Scattering Method

Silicon oxide film (first insulating film: about 300 nm thickness may be sufficient) on silicon substrate (support substrate) is washed with 50% sulfuric acid at room temperature for 30 minutes, and then washed with water.

Photoresist film (OEPR-800) is spin coated on the silicon oxide film thus washed by spin coating method. Photoresist film in a pair of regions where the source electrode and drain electrode are scheduled to be formed is removed using photolithography.

2% of 3-aminopropyltriethoxy silane is added on the substrate from which photoresist film in a pair of regions is removed. This is heated at 45° C. for 30 minutes to allow evaporation of the solvent and is further heated at 110° C. for 5 minutes. After heating, it is washed with sufficient amount of water (this operation introduces amino group on substrate surface).

The substrate thus treated is dipped into mixed solution of ethanol and water (volume ratio 1:4, 50 ml) and heated to 65° C. 1.0 mg of 1-pyrenebutyric acid N-hydroxysuccinimide ester is dissolved into 20 µl of dimethylformamide. 10 µl of the solution thus obtained is dropped onto the mixed solution into which the substrate is dipped, and is caused to react at 65° C. for 1 hour (this operation allows binding of pyrene onto substrate surface).

After the substrate thus obtained is heated at 115° C. for 5 minutes, it is dipped into DMF to remove the photoresist film.

After 0.5 mg of single-walled CNT (Carbon Nanotechnologies INC) is washed with mixed solution of sulfuric acid and nitric acid, it is dispersed into 1 ml of buffer solution. The solution thus obtained is centrifuged, residues obtained are caused to suspend in mixed solvent of sulfuric acid and hydrogen peroxide solution, and subjected to ultrasonic treatment for one hour. Black solution obtained is diluted with water, and dialyzed in distilled water for neutralization of the solution. CNT solution obtained (subjected to ultrasonic treatment prior to use) is dropped onto previously mentioned substrate, allowed to stand for one hour to immobilize CNT to pyrene modified region. The substrate thus treated is washed with DMF and further washed with ethanol. Status of the region where CNT is immobilized is observed by AFM in AC mode to confirm if interval between portions where electrodes are scheduled to be formed are connected by CNT.

A pattern for forming the source electrode and drain electrode is generated on the substrate obtained. For particular method to be used, the same method as used for patterning of pyrene mentioned previously may be used. Pt film with 30 nm thickness and Au film with 100 nm thickness are caused to be vapor-deposited using EB vapor deposition method to form the source electrode and drain electrode. Interval between both electrodes is maintained at about 3 μm.

Detailed Example B of Improved Scattering Method

A gold electrode is formed by vapor deposition on the silicon oxide film (first insulating film: about 300 nm thickness may be sufficient) of the silicon substrate (support substrate). The substrate on which the gold electrode is formed is dipped into 11-mercaptoundecanoic acid solution (0.5 mM) and allowed to stand at room temperature for 10 hours. After washed with ethanol, nitrogen gas is sprayed thereto for drying (carboxyl group is introduced on gold electrode surface by this treatment).

To mixed solution (volume ratio 1:1) of DMF and buffer solution (pH 8) are dissolved water-soluble carbodiimide and 1-pyrenemethylamine hydrochloride (1 mM). The substrate mentioned previously is placed in the solution thus obtained and left at 35° C. for two hours. Following this, it is washed with DMF and pure water (this operation allows binding of pyrene onto gold electrode).

After washing, dimethylformamide solution (0.5 mg/ml) of CNT is dropped onto the substrate and allowed to stand for 10 hours. Following this, subjected to ultrasonic washing in DMF, washed with ethanol, and then nitrogen gas is sprayed to whole substrate for drying.

The gold electrode formed on the substrate according to this method is preferably vapor deposited sufficiently so as to allow flowing of electric current of approximately from 0.1 to 1.0 μA. This is to obtain elements which actuate in stable fashion. Although elements with excessively low source-drain current cause changes in their continuity during operation, thereby loosing continuity, elements which allow flowing of electric current of approximately 0.1 μA exhibit stable continuity even after washed with water.

Detailed Example C of Improved Scattering Method 1.0 mg of 1-pyrenebutyric acid N-hydroxysuccinimide ester is dissolved into 20 μl of dimethylformamide. The solution obtained is added to a solution (0.6 mg of 11-amino-1-undecanethiol is dissolved into 100 μl DMF), and is caused to react at room temperature for one hour. The reaction solution obtained is added to 0.05 mg/ml of dispersion aqueous solution (500 μl) of acid treated CNT, and stirred at room temperature for 12 hours. A substrate on which gold electrode is formed is placed in the solution thus obtained and is caused to react at room temperature for 12 hours to immobilize CNT to the substrate.

Detailed Example D of Improved Scattering Method

DMF solution of 1-pyrenebutyric acid (5 mg/ml, 50 μl) is added to DMF dispersion solution of CNT (0.01 mg/ml, 500 μl), and subjected to ultrasonic treatment at room temperature for two hours. To the solution (100 μl) obtained are added 50 μl of tetraethylene diamine, 50 μl of ethanol, 25 μl of water to obtain dispersion solution. The dispersion solution obtained is filtered by a filter to remove large excess 1-pyrenebutyric acid. Water-ethanol (1:1) mixed solution is added to the filtrate to make 1 ml, and CNT dispersion solution is obtained. Dispersion solution of CNT modified by 1-pyrenebutyric acid is immobilized to a portion subjected to aminosilane treatment where an electrode is scheduled to be formed using condensing reagent such as carbodiimide.

With regard to the method for connecting electrodes by CNT by improved scattering method, array of CNT can be controlled by that CNT presented is set in array along with atomic step on crystal surface of the substrate or by that set in array in a constant direction by electrophoresis. With these considerations, the source electrode and drain electrode can be connected by CNT more efficiently and with good repeatability.

1-5. Gate Electrode

As mentioned previously, FET of the present invention has gate electrode. The gate electrode is disposed so as to be capable of generating polarization in the substrate, where the source electrode and drain electrode are disposed, due to movement of free electrons, by impressing a voltage to the gate electrode. "Polarization due to movement of free electrons" denotes that a region heavily loaded with positive electric charge and a region heavily loaded with negative electric charge are formed respectively in the substrate due to movement of free electrons in the substrate. In a case of a substrate including a support substrate composed of semiconductor or metal and an insulating film, polarization due to movement of free electrons occurs in the support substrate having electric conductivity. Whether or not a substrate is polarized can be confirmed by measurement of potential difference across both sides of the substrate, or the like.

Although material of the gate electrode is not specifically limited, for example, metals such as gold, platinum, titanium, brass are mentioned. Among them, gold is particularly preferable. This is because gold has higher conductivity and errors due to current leakage are less. The gate electrode is formed by vapor deposition of these metals.

Size of the gate electrode is not specifically limited and may be determined with regard to size of ultra fine fiber element (source electrode, drain electrode and ultra fine fiber to become channel). When size of the gate electrode is too small with regard to ultra fine fiber element, control of source-drain current by the gate electrode becomes difficult in some cases. For example, when interval between the source electrode and drain electrode is from 2 to 10 μm, size of the gate electrode may be about 0.1 mm×0.1 mm or more.

The gate electrode disposed so as to polarize the substrate is divided into aspects of (A) Back-gate electrode, (B) Side-gate electrode, and (C) Separate-gate electrode.

(A) Back-Gate Electrode

The back-gate electrode is disposed on the second insulating film of the substrate. Since this gate electrode is disposed at reverse side of the substrate with regard to the source electrode, drain electrode and channel, this is also referred to as back-gate electrode. The back-gate electrode may be disposed in direct contact with the second insulating film or may be disposed apart physically from the second insulating film.

The back-gate electrode may be disposed with regard to a part of the second insulating film or to whole area of the second insulating film. When FET of the present invention is used as the biosensor, and if the gate electrode is formed with regard to whole area of second plane of the substrate, it is possible to bond detection target substance capturing molecule to whole area of the second insulating film.

With conventional back-gate FET, in order to control source-drain current by the back-gate electrode, the back-gate electrode was disposed in direct contact with the support substrate (composed of semiconductor or metal), thereby obtaining interaction.

On the other hand, the present inventors found that direct contact of the gate electrode with support substrate is not necessarily needed. In other words, the present inventors found that, even if an insulating film is provided between the gate electrode and support substrate, source-drain current can be controlled. It is considered that, when a voltage is impressed to the gate electrode, polarization attributable to the presence of free electrons in the support substrate occurs in the support substrate (composed of semiconductor or metal), and source-drain electrode is eventually controlled. Although polarization due to movement of free electrons includes capacitive coupling factor, other factors should be taken into considerations.

(B) Side Gate Electrode

The side-gate electrode is disposed on the first insulating film of the substrate. This electrode is disposed on the same plane of the substrate with regard to the source electrode, drain electrode, and channel, and hence, is referred to as side-gate electrode. The side-gate electrode may be disposed in direct contact with the first insulating film or may be disposed apart physically from the first insulating film.

With FET of the present invention, an interval between the side-gate electrode disposed on the same plane of the substrate and ultra fine fiber can be set to 10 μm or more, further, 100 μm or more, further, 1 mm or more. Upper limit is, although not specifically limited, not more than several centimeters. "Interval between gate electrode and ultra fine fiber" denotes a shortest distance for the both.

With conventional side-gate FET, it was considered that in order to control source-drain current by gate electrode, direct interaction was necessary between side-gate electrode and source electrode, drain electrode and channel. Therefore, with conventional side-gate FET, interval between side-gate electrode and channel was designed to be as short as possible (about 1 μm at the longest).

Meanwhile, the present inventors found that it is not necessarily required to bring side-gate electrode close to source electrode, drain electrode and channel. It is considered that even if the side-gate electrode and source electrode, drain electrode and channel are formed on the same insulating film, when a voltage is impressed to the side-gate electrode, polarization attributable to presence of free electrons in the support substrate occurs in the support substrate (composed of semiconductor or metal) under the insulating film, and source-drain current is controlled by this polarization. Although polarization includes factors due to capacitive coupling, other factors should be taken into considerations.

The side-gate FET of the present invention is, as will be described later, applied to biosensors in some cases. In this case, the side-gate electrode is bound with detection target substance capturing molecule and in some cases, sample solution is dropped thereon. With side-gate FET of the present invention, interval between the side-gate electrode and source electrode, drain electrode and channel can be widened, and therefore, contamination of ultra fine fiber element by sample solution can be prevented.

(C) Separate-Gate Electrode

Separate-gate electrode is, although separated from substrate on which are disposed source electrode, drain electrode and channel, disposed on a second substrate which is electrically connected thereto. The second substrate can be a substrate including a support substrate composed of semiconductor or metal, and having insulating film formed on at least one of planes of the support substrate, or a substrate including an insulating body, while the former substrate is preferable.

The second substrate on which is disposed gate electrode is separated from substrate on which are disposed source electrode, drain electrode and channel. An interval between substrate on which are disposed source electrode, drain electrode and channel and second substrate on which is disposed gate electrode is not specifically limited, and can be 3 mm or more, further 10 mm or more, further 15 mm or more, or more than that.

As mentioned previously, the second substrate, on which is disposed gate electrode, is electrically connected to the substrate on which are disposed source electrode, drain electrode and channel. "Electrically connected" is meant by, for example, (a) Substrate and second substrate are mounted on the same conductive substrate, or (b) Substrate and second substrate are mounted on different conductive substrate, respectively, and each conductive substrate is connected by conductive member. Embodiment (a) is shown in FIG. 4 and Embodiment (b) is shown in FIG. 5.

Although conductive substrate is not specifically limited, for example, glass substrate with gold thin film vapor-deposited thereon or substrate composed of materials such as brass are mentioned. Although conductive member is not specifically limited, for example, conductive wires such as copper wire are mentioned.

As will be described later, separate-gate FET of the present invention is in some cases applied to biosensors. In this case, separate-gate FET of the present invention has higher degree of freedom of structure since the substrate on which are disposed source electrode, drain electrode and channel can be separated from the second substrate on which is disposed gate electrode. Therefore, separate-gate FET of the present invention can contribute to preparation of biosensors with higher practical utility.

1-6. Characteristics of Field Effect Transistor of the Present Invention

FIG. 18 is a view showing characteristics of the back-gate FET of the present invention. A graph showing relationship between voltage to be impressed to the gate electrode (hereafter referred to as "gate voltage": Vgate) and source-drain current (Isd) (hereafter referred to as "I-V characteristics") is depicted for a case where source-drain voltage is fixed to 1 V. In the FET used for measurement, the support substrate was silicon substrate with 500 μm thickness, the first insulating film and second insulating film were silicon oxide with 300 nm thickness, the ultra fine fiber was single-walled CNT, area of the source electrode and drain electrode is from 0.20 to 0.25 $mm^2$, respectively, area of the substrate was 1 $cm^2$ (1 cm×1 cm). Further, it was confirmed by AFM that the source electrode and drain electrode were connected by several CNTs. With the FET of the present invention, as shown in FIG. 18, source-drain current of approximately several hundred nA is observable with gate voltage in a range from −20V to −5V.

Further, with FET of the present invention, source-drain current changes sensitively with regard to changes in electric charge (technically, "electron state") on the channel (ultra fine fiber), or changes in difference between the channel, and the source electrode and drain electrode (technically, chemical potential). These changes are induced by changing potential of the gate electrode disposed on the substrate, and source-drain current changes sensitively with regard to changes in electric state of the gate electrode. Although reasons explaining this are not exactly identified yet, it is presumed that, with substrate structure of the present invention, an interface contacting with the insulating film, which covers surface of the support substrate composed of semiconductor or the like, changes depending on electric state of the gate electrode and induces changes of channel part by effects of polarization due to presence of free electrons in the support substrate and to capacitive coupling via insulating film.

In other words, it is presumed that, when a strong electric field is applied to the support substrate covered by the insulating film by gate voltage, density distribution of carrier in the support substrate around the interface with regard to insulating film changes depending on voltage difference between the electrode and support substrate. This presumption is supported by findings shown below.

With n-type semiconductor MOS (metal-oxide semiconductor) diode, when potential of a metal is lowered, free electrons in the semiconductor are kept away from the interface and depletion layer becomes thicker, and therefore, capacitance across the metal and semiconductor is reduced. However, if potential of the metal is lowered further, p-type MOS inversion layer is generated at the interface between n-type semiconductor and oxide, and capacitance is then increased again. (For the above, see, for example, "Rikagaku-jiten", Ver. 5. Iwanami Shoten Publishers, p. 1380). "Depletion layer" is meant by a thin layer where a little free electrons or holes are present at pn-junction plane of semiconductor and in semiconductor of MOS structure. Thickness of the depletion layer changes sensitively by the voltage impressed.

Further, "MOS inversion layer" is meant by a layer with conduction type opposite to that of the inside which appears on the surface while a great number of carriers around the surface are pushed into semiconductor inside, when a metal film is attached to semiconductor surface via insulating film (composed of oxide or the like). Thickness of the inversion layer is also changed by the voltage impressed.

That is, that interface with insulating film of the support substrate is actuated likewise variable capacitance diode by gate voltage is equivalent to that thickness of the depletion layer or inversion layer of the support substrate changes by gate voltage.

Therefore, when detection target substance capturing molecule is bound to gate electrode, ultra fine fiber, interface between gate electrode and insulating film, or insulating film surface in the vicinity of ultra fine fiber, image charge in support substrate of the detection target substance capturing molecule is generated to gate electrode, source electrode, drain electrode, and depletion layer or inversion layer in the vicinity of channel (interfacial state appears). This results in changes in capacitance across gate electrode and source electrode (hereafter referred to as "gate-source capacitance"), changes in capacitance across the gate electrode and drain electrode (hereafter referred to as "gate-drain capacitance"), and changes in capacitance across the gate electrode and channel (hereafter referred to as "gate-channel capacitance"), respectively. These changes result in changes in potential of the channel and as a result, source-drain current changes.

That is, an interface between support substrate composed of semiconductor or the like and insulating film covering the support substrate is actuated in variable capacitance diode fashion by gate voltage. In other words, thickness of the depletion layer or inversion layer in the support substrate changes. Then, image charge is generated depending on thickness of the depletion layer or inversion layer, potential of the channel and electric charge on the channel change due to image charge generated, and source-drain current changes accordingly.

According to the presumption, with FET of the present invention, when an electric field not less than a certain threshold is applied in the substrate, changes in source-drain current with regard to changes in potential of the channel or in electric charge on the channel become large, and as the biosensor, changes in electron state induced by molecules on the element can be reflected to the channel. In other words, as the biosensor, molecular interaction on the element (e.g., antigen-antibody reaction and enzyme reaction) can be detected with higher accuracy by changes in source-drain current.

Moreover, according to the presumption, new I-V characteristics and I-Vg characteristics (relationship between gate voltage and source-drain current) utilizing polarization due to movement of free electrons caused around the interface between the support substrate and insulating film (formation of inversion layer) are predicted. In fact, with FET of the present invention, new characteristics (described later) which exhibit different operations from those of conventional FET and CNT-FET were already obtained.

Here, "inversion layer" denotes a layer induced around surface in the semiconductor (boundary region), when a metal film (electrode) is provided to semiconductor surface via a insulating film and a higher electric field is applied to the semiconductor surface, as mentioned above, which layer has electric charge opposite to the electric field to cancel it, and is caused around the interface with the insulating film of the support substrate, of polarization due to movement of free electrons.

In the following description, I-V characteristics curve and I-Vg characteristics curve of FET on the present invention using CNT as the ultra fine fiber are shown.

First, I-V characteristics curve and I-Vg characteristics curve of back-gate FET (shown in FIG. 2) of the present invention are shown. In FET used for the measurement, the support substrate was silicon substrate with 500 μm thickness, the first insulating film and second insulating film were silicon oxide with 300 nm thickness, area of the substrate was 1 cm² (1 cm×1 cm), the ultra fine fiber was single-walled CNT, interval between the source electrode and drain electrode was 5 μm, area of the gate electrode was 100 mm². Further, it was confirmed by AFM that the source electrode and drain electrode were connected by several CNTs.

FIG. 19 is a view showing one example of I-V characteristics curve of back-gate FET of the present invention. FIG. 20 is a view showing one example of I-Vg characteristics curve of back-gate FET of the present invention. In FIG. 20, curve "a" is a characteristics curve when source-drain voltage is set to −1V, and curve "b" is a characteristics curve when source-drain voltage is set to +1V.

Next, I-V characteristics curve and I-Vg characteristics curve of side-gate FET (shown in FIG. 3). In FET used for the measurement, the support substrate was silicon substrate with 500 μm thickness, the first insulating film and second insulating film were silicon oxide with 300 nm thickness, area of the substrate was 1 cm² (1 cm×1 cm), the ultra fine fiber was single-walled CNT, interval between the source electrode and drain electrode was 5 μm, area of the gate electrode was 0.25 mm². Further, it was confirmed by AFM that the source electrode and drain electrode were connected by several CNTs.

FIG. 21 is a view showing one example of I-V characteristics curve of side-gate FET of the present invention. FIG. 22 (A) and FIG. 22 (B) are drawings showing one example of I-Vg characteristics curve of side-gate FET of the present invention, where interval between the gate electrode and CNT is set to 50 μm and 1 cm, respectively. Further, I-Vg characteristics curve obtained using back-gate electrode is shown FIG. 22(C). All of these characteristics were measured using the same CNT.

No significant change is noticed with I-Vg characteristics curves shown in FIG. 22. Therefore, it is understood that electric characteristics of a transistor do not change even after an interval between the gate electrode and CNT is varied.

Next, I-V characteristics curve and I-Vg characteristics curve of separate-gate FET of the present invention (shown in FIG. 4) are shown. In FET used for the measurement, the support substrate of both the substrate and second substrate were both silicon substrate with 500 μm thickness, the insulating film covering both sides of the substrate and second substrate were both silicon substrate with 300 nm thickness, area of the substrate and second substrate were both 1 cm² (1 cm×1 cm), the ultra fine fiber was single-walled CNT, interval between the source electrode and drain electrode was 5 μm, area of the gate electrode was 0.1 mm$^2$. Further, it was confirmed by AFM that the source electrode and drain electrode were connected by several CNTs.

FIG. 23 and FIG. 24 are drawings showing one example of I-V characteristics curve and I-Vg characteristics curve of separate-gate FET of the present invention where interval between the substrate and second substrate is set to 3 mm. FIG. 25 and FIG. 26 are drawings showing one example of I-V characteristics curve and I-Vg characteristics curve of separate-gate FET of the present invention where interval between the substrates is set to 10 mm. FIG. 27 and FIG. 28 are view showing one example of I-V characteristics curve and I-Vg characteristics curve of separate-gate FET of the present invention where interval between the substrates is set to 15 mm.

No significant change is noticed with I-V characteristics curves shown in FIG. 23, FIG. 25, and FIG. 27. Similarly, no significant change is noticed with I-Vg characteristics curves shown FIG. 24, FIG. 26, and FIG. 28. Therefore, it is understood that electric characteristics as FET do not change even after an interval between the substrate and second substrate is varied.

When FET of the present invention is applied to biosensors, and if molecules are adhered to the gate electrode or ultra fine fiber (e.g., CNT), electron state of the ultra fine fiber is changed indirectly or directly. Molecules adhered can be detected from changes in source-drain current caused on this occasion. Moreover, when the gate electrode or ultra fine fiber is modified by molecule, it is possible to detect a modified molecule from changes in electric current or to detect a reaction of modified molecule with other molecule. Particularly when the gate electrode or ultra fine fiber is modified by antibody (or antigen), detection of a particular antigen (or antibody) utilizing antigen-antibody reaction is possible, and therefore, microorganism such as viruses and bacteria of infectious diseases can be detected super-sensitively and promptly.

1-7. Application of Field Effect Transistor of the Present Invention

FET of the present invention can be used for arbitrary applications. For example, FET of the present invention can be used in integrated circuits, pH meters, biosensors, or the like, while use in biosensors is preferable. When used for biosensors, it is preferable that a detection target substance capturing molecule which reacts with a detection target substance is bound to FET of the present invention.

2. Biosensor Using FET of the Present Invention

As mentioned previously, FET of the present invention can be applied to biosensors. A biosensor using FET of the present invention (hereafter referred to as "biosensor of the present invention") has FET of the present invention and a detection target substance capturing molecule capable of interacting (e.g., binding) with detection target substance. In this case, the detection target substance capturing molecule is preferably bound onto FET of the present invention.

Although detection target substance capturing molecules are not specifically limited, for example, antibodies, antigens, enzymes, receptors, nucleic acids, cells, microorganisms are mentioned. Further, although detection target substances are not specifically limited, for example, antigens, antibodies, microorganisms (viruses, bacteria), chemical substances (residual agricultural chemicals or the like) are mentioned.

The biosensor of the present invention detects a detection target substance based on changes in source-drain current or source-drain voltage generated by interaction of the detection target substance with detection target substance capturing molecule. Changes in source-drain current can be confirmed by, for example, I-V characteristics curve or I-Vg characteristics curve. I-V characteristics curve is a curve showing relationship between source-drain current and source-drain voltage when gate voltage is maintained at constant. I-Vg characteristics curve is a curve showing relationship between source-drain current and gate voltage when source-drain voltage is maintained at constant.

The biosensor of the present invention needs energization to allow detection operation. Therefore, the biosensor of the present invention preferably has aspects of biosensor device further equipped with power supply or power acquisition member as will be described later.

2-1. Site for Binding Detection Target Substance Capturing Molecule

In the biosensor of the present invention, although a site where a detection target substance capturing molecule is bound to FET of the present invention is not specifically limited, for example, ultra fine fiber which connects the source electrode and drain electrode, insulating protective film which protects ultra fine fiber, second insulating film of the substrate, gate electrode, or the like are mentioned.

In the following description, examples of binding a detection target substance capturing molecule to FET of the present invention are shown.

FIG. 29 through FIG. 33 are drawings showing examples of binding of a detection target substance capturing molecule to back-gate FET of the present invention.

FIG. 29 is a view showing a case where detection target substance capturing molecule is bound to ultra fine fiber. In this example, detection sensitivity can be improved since detection target substance capturing molecule is bound directly to ultra fine fiber that acts as FET channel.

FIG. 30 is a view showing a case where detection target substance capturing molecule is bound to insulating protective film. In this example, noise can be reduced since sample solution has no opportunity to contact directly with ultra fine fiber.

FIG. 31 is a view showing a case where detection target substance capturing molecule is bound to second insulating film. In this example, reuse is easy since second plane of the substrate can be washed without causing damage to ultra fine fiber. Further, it is possible to bond relatively large number of detection target substance capturing molecules since detection target substance capturing molecules can be bound onto whole second plane of the substrate.

Figure 31A:
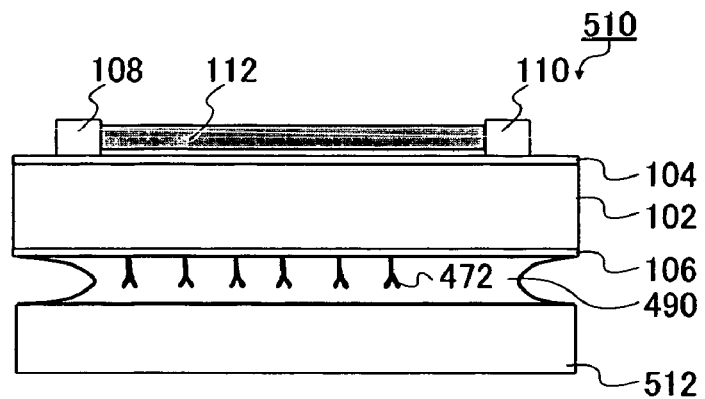
Figure 31B:
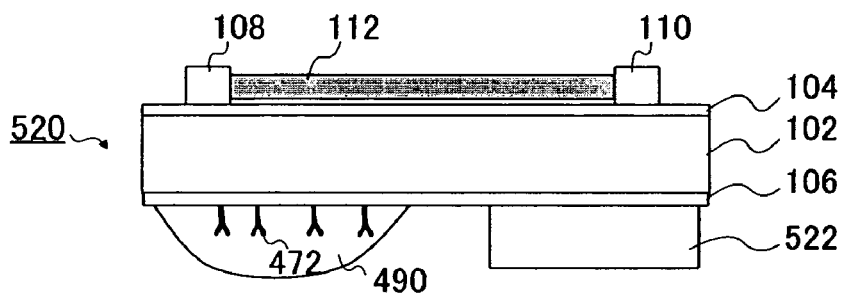
Figure 31C:
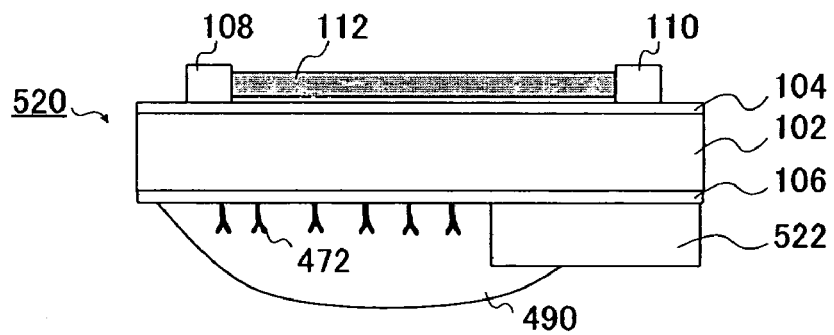
Figure 31D:
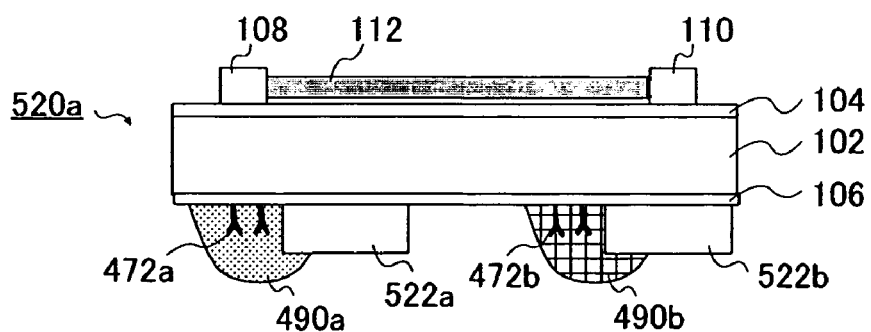

FIG. 31A is a view showing a case where detection target substance capturing molecule is bound to second insulating film when back-gate electrode is disposed without contacting with second insulating film. FIG. 31B and FIG. 31C are drawings showing a case where detection target substance capturing molecule is bound to second insulating film when back-gate electrode is disposed so as to contact with second insulating film. The sample solution may not contact with the back-gate electrode (FIG. 31B) or may contact (FIG. 31C). FIG. 31D is a view showing a case where each of a plurality types of detection target substance capturing molecules is bound to second insulating film when a plurality of back-gate electrodes are disposed on second insulating film.

FIG. 32 is a view showing a case where a concave is formed on second plane of the substrate, and detection target substance capturing molecule is bound to the second insulating film located on the bottom of the concave. Although material of sidewall of the concave is not specifically limited, for example, silicon oxide is mentioned. In this example, it is possible to supply a given volume of sample solution by regulating volume of the concave. In addition, the sample solution being added is hardly scattered and therefore, detection target substance capturing molecule can be held with stably manner at bound site.

Figure 32A:
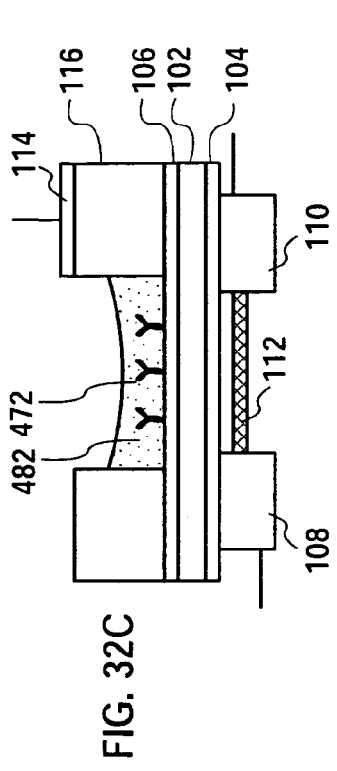
Figure 32B:
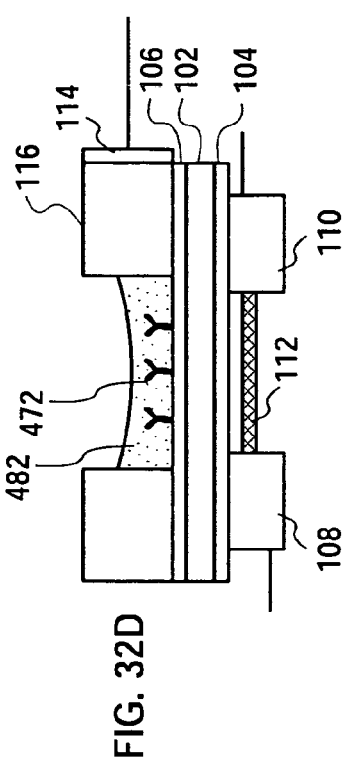
Figure 32C:
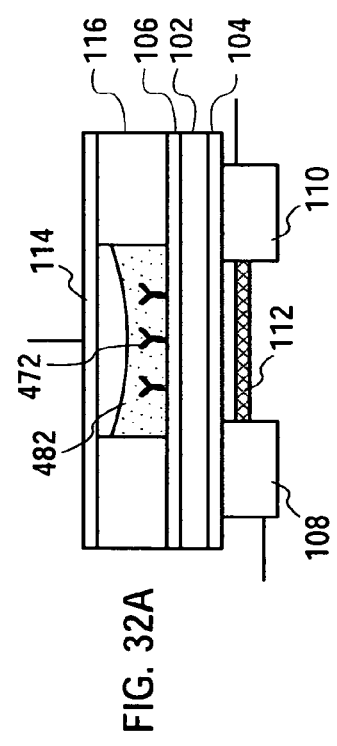
Figure 32D:
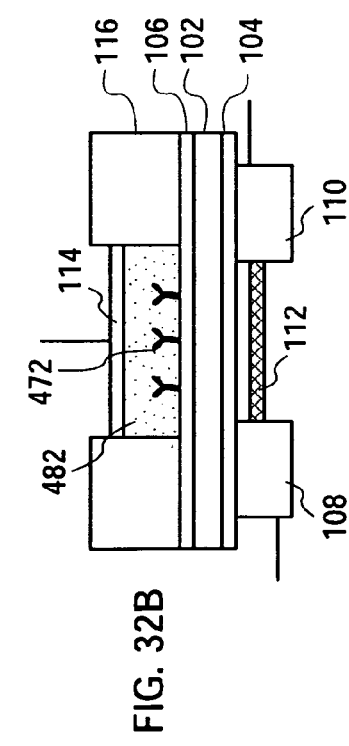
Figure 32E:
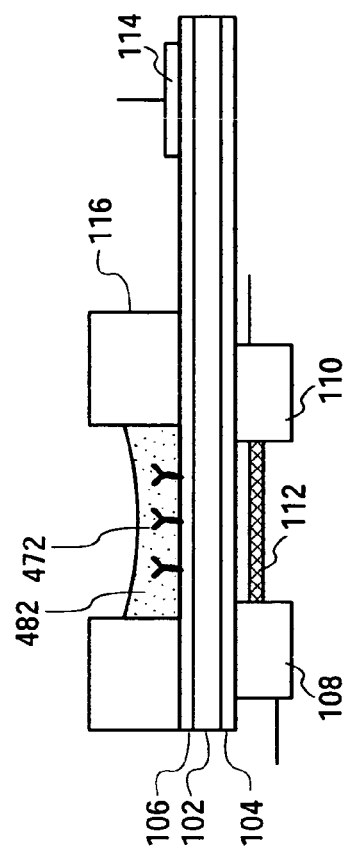

FIG. 32A and FIG. 32B are drawings showing a case where back-gate electrode functions as a cover of concave. FIG. 32C is a view showing a case where back-gate electrode is disposed on the sidewall of the concave. FIG. 32D is a view showing a case where back-gate electrode is disposed on surface of sidewall of the concave. FIG. 32E is a view showing a case where back-gate electrode is disposed on second insulating film outside the concave.

FIG. 33 is a view showing a case where detection target substance capturing molecule is bound to gate electrode. In this example, reuse is easy since second plane of the substrate can be washed without causing damage to ultra fine fiber.

FIG. 33A is a view showing a case where detection target substance capturing molecule is bound to back-gate electrode when one back-gate electrode is disposed. FIG. 32B is a view showing a case where each of a plurality of types of detection target substance capturing molecules is bound to one of back-gate electrodes respectively, when a plurality of the back-gate electrodes are disposed.

FIG. 34 through FIG. 38 are drawings showing a case where detection target substance capturing molecule is bound to side-gate FET of the present invention.

FIG. 34 is a view showing a case where detection target substance capturing molecule is bound to ultra fine fiber. In this example, detection sensitivity can be improved since detection target substance capturing molecule is bound directly to ultra fine fiber that serves as a channel.

FIG. 35 is a view showing a case where detection target substance capturing molecule is bound to insulating protective film. In this example, high-sensitivity sensor can be presented since there is no opportunity for sample solution to contact directly with ultra fine fiber and electrode.

FIG. 35A is a view showing a case where detection target substance capturing molecule is bound to insulating protective film that protects ultra fine fiber. FIG. 35B is a view showing a case where detection target substance capturing molecule is bound to insulating protective film that protects ultra fine fiber and gate electrode.

FIG. 36 is a view showing a case where detection target substance capturing molecule is bound to second insulating film when side-gate electrode is disposed so as to contact with second insulating film. The sample solution may contact with the side-gate electrode (FIG. 36A) or may not contact (FIG. 36B).

FIG. 37 is a view showing a case where a concave is formed on second plane of the substrate, and detection target substance capturing molecule is bound to the second insulating film located on the bottom of the concave. Although material of sidewall of the concave is not specifically limited, for example, silicon oxide is mentioned. In this example, it is possible to position accurately sample solution to the site where detection target substance capturing molecule is bound (i.e., within concave).

FIG. 38 is a view showing a case where detection target substance capturing molecule is bound onto gate electrode.

FIG. 39 through FIG. 44 are drawings showing a case where detection target substance capturing molecule is bound to separate-gate FET of the present invention. In a case of biosensor including separate-gate FET of the present invention, detection target substance capturing molecule is preferably integrated into gate element section.

FIG. 39 is a view showing a case where detection target substance capturing molecule is bound to insulating film when separate-gate electrode is disposed without contacting with insulating film.

FIG. 40 is a view showing a case where detection target substance capturing molecule is bound to insulating film when separate-gate electrode is disposed so as to contact with insulating film. The test solution may contact with separate-gate electrode (FIG. 40A) or may not contact (FIG. 40B). FIG. 40C is a view showing a case where each of several types of detection target substance capturing molecules is bound to insulating film respectively, when a plurality of separate-gate electrodes are disposed.

FIG. 41 is a view showing a case where detection target substance capturing molecule is bound to gate electrode. FIG. 41A is a view showing a case where detection target substance capturing molecule is bound to separate-gate electrode when one separate-gate electrode is disposed. FIG. 41B is a view showing a case where each of a plurality of types of detection target substance capturing molecules is bound to one of separate-gate electrodes respectively, when a plurality of the separate-gate electrodes are disposed.

FIG. 42 is a view showing an example where, when there are a plurality of gate element sections, each of several types of detection target substance capturing molecules is bound to one of the separate-gate electrodes respectively.

FIG. 43 is a view showing a case where each of a plurality of types of detection target substance capturing molecules is bound to insulating film, when ultra fine fiber element section and gate element section are disposed so as to grasp conductive substrate, and a plurality of separate-gate electrodes are disposed on gate element section. In this example, removal of gate element section from ultra fine fiber element section can be made with ease. Therefore, it is possible to replace a plurality of gate element sections for one ultra fine fiber element section.

FIG. 44 is a view showing a case where a plurality of detection target substance capturing molecules are bound to insulating film, when ultra fine fiber element section and gate element section are electrically connected by conductive member, and a plurality of separate-gate electrodes are disposed on gate element section.

2-2. Method for Binding Detection Target Substance Capturing Molecule

As mentioned previously, with biosensor of the present invention, detection target substance capturing molecule is preferably bound to FET of the present invention.

The following description explains four methods for binding detection target substance capturing molecule to substrate, gate electrode, or ultra fine fiber. Particularly, explanation will be given for a case where detection target substance capturing molecule is antibody.

A first method uses His-tag fusion capturing molecule as detection target substance capturing molecule. As one example, a method for binding His-tag fusion antibody to ultra fine fiber (CNT) will be explained referring to FIG. 45. It is possible to bond His-tag fusion antibody to substrate and also to gate electrode using the same method.

Figure 45A:
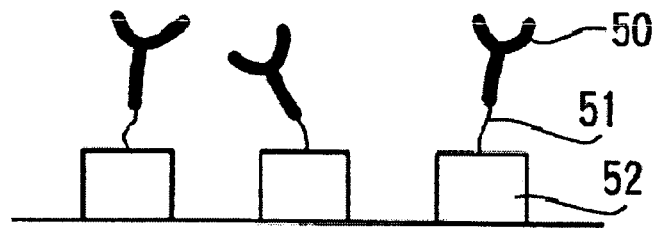
Figure 45B:
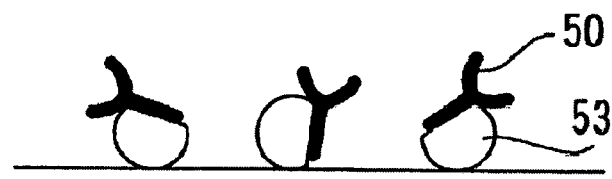

First, antibody 50 in which His-tag 51 is fused by gene manipulation is prepared. Second, ultra fine fiber of FET is directly modified by pyrene. NTA52 is caused to be bound to ultra fine fiber thus modified. Following this, a solution containing transition metal ion (nickel ion, cobalt ion, or the like) is dropped onto ultra fine fiber to cause formation of NTA52 being bound to ultra fine fiber and complex. Further, by dropping a solution containing antibody 50 in which His-tag 51 is fused, antibody 50 is caused to be bound to ultra fine fiber as shown in FIG. 45A. Antibody 50 thus bound has a constant orientation with regard to bound plane.

When NTA52 is immobilized to insulating film of the substrate, a method for treating insulating film with silane coupling agent is effectively used. When NTA52 is immobilized to gate electrode (metal), a method for adding thiol group to N-maleimide group of NTA52 is effectively used. Antibody 50 thus bound has a constant orientation with regard to bound plane.

A second method uses, when detection target substance capturing molecule is IgG antibody, protein A, protein G, protein L, or IgG binding domain thereof are used. The antibody referred to herein includes single-chain antibody having binding capacity specific to antigen.

Protein A, protein G, or Protein A/G (a fusion protein in which IgG binding characteristics thereof are combined) has a capability to bind to Fc region of IgG immunoglobulin. Protein L has a capability to bind to κ chain of light chain of IgG immunoglobulin. Further, any of these proteins has a characteristics easily adhered onto gold surface as well as other proteins.

Utilizing these characteristics, it is possible to orient antibody 50 to some extent by causing protein A, protein G, protein A/G, protein L, or recombinant protein 53 (hereafter referred in some cases to as "IgG binding protein") having IgG binding domain thereof to directly adhere to gate electrode prepared by gold, and by causing IgG antibody 50, which is used as the detection target substance capturing molecule, to bind to IgG binding protein 53 thus adhered. However, since, with the second method, IgG binding protein 53 binds to the electrode in a random manner, sufficient orientation is not obtained in some cases (see FIG. 45B).

A third method is to orient detection target substance capturing molecule (antibody) in similar fashion as the first method by adding his-tag to IgG binding protein and by binding IgG binding protein via NTA-Ni and his-tag. Further, by adding his-tag, detection target substance capturing molecule (antibody) can be also oriented to insulating film or ultra fine fiber, in addition to the gate electrode.

Figure 45C:
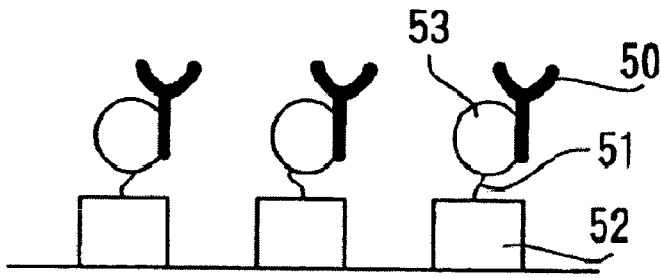

In the following description, a method for binding IgG binding protein, to which his-tag is added, to insulating film will be explained referring to FIG. 45C. It is also possible to bind the same to ultra fine fiber and gate electrode.

First, IgG binding protein to which his-tag 51 is added by gene manipulation is prepared. In IgG binding protein 53, orientation of antibody can be improved by setting his-tag addition site in view of location of antibody binding site. Next, insulating film is treated by silane coupling agent, NTA52 is caused to be bound to modified substrate, a solution containing transition metal ion (nickel ion, cobalt ion, or the like) is dropped onto the substrate to cause formation of complex with NTA52 immobilized on the substrate, further, IgG binding protein 53 is immobilized to insulating film by dropping a solution containing IgG binding protein 53 to which his-tag 51 is added. It is possible to endow orientation to the antibody by binding IgG antibody 50, which acts as the detection target substance capturing molecule, to immobilized IgG binding protein 53.

Figure 45D:
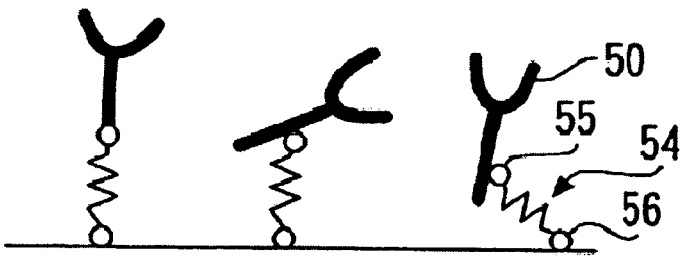

As shown in FIG. 45D, a fourth method is to bind detection target substance capturing molecules to insulating film, gate electrode, or ultra fine fiber via bifunctional crosslinking reagent 54 having two functional groups 55 and 56 which respectively form covalent bonding with functional groups (each may be identical or different). Bifunctional crosslinking reagent 54 includes two functional groups 55 and 56, and hydrophilic polymer chain such as polyethylene glycol or hydrophobic chain such as alkyl chain for binding them. Examples of functional groups 55 and 56 include such a group in which one forms covalent bonding with amino group and the other forms the same with thiol group.

For example, when bound to insulating film; 1) After detection target substance capturing molecule (antibody 50) and bifunctional crosslinking reagent 54 are reacted, unreacted bifunctional crosslinking reagents are removed by dialysis or the like, and "detection target substance capturing molecule—bifunctional crosslinking reagent complex" is reacted with substrate insulating film treated by silane coupling agent for immobilizing, or 2) bifunctional crosslinking reagent 54 are reacted with substrate insulating film plane treated by silane coupling agent, and then detection target substance capturing molecule (antibody 50) is reacted with the substrate for immobilizing.

According to the method using NTA as shown in FIG. 45A, preparation by gene manipulation of detection target substance capturing molecule to which his-tag is attached takes several months of time. When detection target substance capturing molecule is an antibody, hybridoma for secretion of a target antibody is necessary for the sake of preparation of antibody to which his-tag is added. However, procurement of hybridoma is normally difficult and own preparation thereof is very much time-consuming. Therefore, with a method shown in FIG. 45C which uses IgG binding protein 53, if proteins to which are added these his-tags are prepared once, they can be used for IgG antibody, and various detection target substances can be detected in a short time. Further, in a method with bifunctional crosslinking reagent 54 shown in FIG. 45D, gene manipulation for introduction of his-tag is unnecessary, and therefore, detection target substance capturing molecules can be prepared more promptly.

Moreover, when an antibody is used as the detection target substance capturing molecule, while use of polyclonal antibody is difficult with a method using NTA, immobilization method based on bifunctional crosslinking reagent allows use of polyclonal antibody, and therefore, improvement of sensitivity and accuracy as the biosensor can be expected. Further, since the bifunctional crosslinking reagent has hydrophilic polymer chain or hydrophobic chain between the two functional groups 55 and 56, background in detection by the biosensor of the present invention can be reduced.

2-3. Biosensor Device Having Detachable Element Section

The biosensor device of the present invention may be equipped with an element section having detection target substance capturing molecule, which is detachable to and from biosensor device body. When the element section is mounted to the biosensor device body, electrode in the element section (either one of source electrode, drain electrode and gate electrode, or a plurality of them) is electrically connected thereto, thereby allowing detection operation.

FIG. 46 is a schematic view showing one example of the biosensor device according to the present invention having detachable biosensor device. As shown in FIG. 46, the element section is preferably constructed in chip form.

In FIG. 46, the biosensor device includes biosensor device body 7601, and element section 7702 including detection target substance capturing molecule. Biosensor device body 7601 includes display section 7604 on which are displayed results of detection.

Although biosensor device body normally includes power supply, utilization of external power source with a provision of D/A converter, or acquisition of external power through USB interface may be employed. Further, biosensor device body may output results of detection by providing an interface instead of displaying them on display section. Further, a storage section may be provided to biosensor device body for temporal storage of results of detection. With this consideration, centralized management of detection results at aggregation center is made possible while detection results are transmitted by wireless transmission means.

The element section detachable to and from the biosensor device body preferably has at least a detection target substance capturing molecule, and any one of the followings: (A) Back-gate FET of the present invention to which is integrated the detection target substance capturing molecule, (B) Side-gate FET of the present invention to which is integrated the detection target substance capturing molecule, and (C) Gate element section to which is integrated detection target substance capturing molecule in the separate-gate FET of the present invention. The following description explains each of embodiments.

(A) Biosensor Device Having Back-Gate FET of the Present Invention at Element Section In this embodiment, the biosensor device body includes a power supply and display section. The power supply may be substituted with external power acquisition means for acquiring electric power from the outside. Further, the display section may be replaced by external output type.

In the present embodiment, the element section includes back-gate FET of the present invention, and detection target substance capturing molecule being integrated to back-gate FET of the present invention. Back-gate FET of the present invention used in the element section can assume each of embodiments of the back-gate FET. When element section is mounted to the biosensor device body, source electrode, drain electrode, and gate electrode in the element section can be electrically connected to the power supply in the biosensor device body.

Site on the back-gate FET of the present invention to which the detection target substance capturing molecule is bound is, as mentioned previously, ultra fine fiber, insulating protective film (if provided), second insulating film, gate electrode, or the like, while second insulating film is preferable. This is because contamination of the ultra fine fiber can be prevented even if sample solution is added to the site where detection target substance capturing molecule is bound. Further, there is such an advantage that the site where detection target substance capturing molecule is bound can be washed without causing damage to the ultra fine fiber.

The gate electrode may be disposed in direct contact with the second insulating film or may be disposed apart from the second insulating film. When the detection target substance capturing molecule is bound to the second insulating film, the gate electrode is preferably disposed apart from the second insulating film. Further, when the gate electrode is disposed apart from the second insulating film, size of the gate electrode is preferably capable of covering whole area of the second insulating film. This is because the detection target substance capturing molecule can be bound to whole area of the second insulating film. The number of gate electrodes may be, as mentioned previously, one or more.

FIG. 47 is a view showing one example of biosensor device having back-gate FET of the present invention at element section. In FIG. 47, the biosensor device includes biosensor device body 7601 and element section 7602 disposed on the biosensor device body.

Biosensor device body 7601 includes power supply 7603 and display section 7604.

Element section 7602 is detachable to and from biosensor device body 7601, and includes substrate 7609, ultra fine fiber element 7605, gate electrode 7614, and detection target substance capturing molecule 7613.

Substrate 7609 includes support substrate 7608, and first insulating film 7607 and second insulating film 7616. Further, ultra fine fiber element 7605 includes source electrode 7610 and drain electrode 7611 disposed on first insulating film 7607, and ultra fine fiber 7612 for electrically connecting source electrode 7610 and drain electrode 7611. Source electrode 7610 and drain electrode 7611 are, when element section 7602 is mounted to biosensor device body 7601, connected to power supply 7603 and voltage thereof is controllable.

On second insulating film 7616 of substrate 7609 is bound detection target substance capturing molecule 7613 which specifically reacts with a detection target substance. Gate electrode 7614 is spaced apart in vertical direction from second insulating film 7616 to which is bound detection target substance capturing molecule. Further, gate electrode 7614 is, when element section 7602 is mounted to biosensor device body 7601, connected to power supply 7603 and voltage thereof is controllable. FIG. 47 shows a state where sample solution 7615 is present between second insulating film 7616 and gate electrode 7614.

To detect a detection target substance by the biosensor device shown in FIG. 47, sample solution 7615 is dropped onto second insulating film 7616 (and is dried depending on the case may be), element section 7602 to which gate electrode 7614 is disposed is mounted to biosensor device body 7601, and then a voltage is simply applied to the gate electrode and drain electrode, and gate electrode. With these operations, changes in source-drain current of element section 7602 are caused by, for example, molecular interaction on second insulating film 7616. These changes are displayed on display section 7604.

(B) Biosensor Device Having Side-Gate FET of the Present Invention at Element Section In this embodiment, the biosensor device body includes a power supply and a display section. The power supply may be substituted with external power acquisition means for acquiring electric power from the outside. Further, the display section may be replaced by external output type.

In the present embodiment, the element section includes side-gate FET of the present invention, and detection target substance capturing molecule being bound to side-gate FET of the present invention. Side-gate FET of the present invention used in the element section can assume any of the embodiments of the side-gate FET. When element section is mounted to the biosensor device body, source electrode, drain electrode, and gate electrode in the element section can be electrically connected to the power supply in the biosensor device body.

Site on the side-gate FET of the present invention to which the detection target substance capturing molecule is bound is, as mentioned previously, ultra fine fiber, insulating protective film (if provided), gate electrode, or the like, while gate electrode is preferable. This is because when the detection target substance capturing molecule is only on the electrode, image charge thereof is generated only in the electrode, and interference with image charges in other electrodes hardly occur.

The gate electrode may be disposed in direct contact with the first insulating film or may be disposed apart from the first insulating film. When the detection target substance capturing molecule is bound to the gate electrode, the gate electrode is preferably disposed in direct contact with the first insulating film. The number of gate electrodes may be, as mentioned previously, one or more.

FIG. 48 is a view showing one example of the biosensor device having side-gate FET of the present invention at the element section. In FIG. 48A, the biosensor device includes biosensor device body 7601, and element section 7602 disposed at upper part of the biosensor device body. Biosensor device body 7601 includes power supply 7603, and display section 7604.

Element section 7602 is detachable to and from biosensor device body 7601, and includes substrate 7609, ultra fine fiber element 7605, a plurality of gate electrodes 7614, and detection target substance capturing molecule 7613.

Substrate 7609 includes support substrate 7608, first insulating film 7607, and second insulating film 7616. Further, ultra fine fiber element 7605 includes source electrode 7610 and drain electrode 7611 being disposed on first insulating film 7607, and ultra fine fiber 7612 for electrically connecting source electrode 7610 and drain electrode 7611. Source electrode 7610 and drain electrode 7611, and gate electrode 7614 are, when element section 7602 is mounted to biosensor device body 7601, connected to power supply 7603 and voltage thereof is controllable.

On gate electrode 7614 disposed on first insulating film 7607 are bound detection target substance capturing molecules 7613 each specifically reacts with detection target substances. In this case, detection target substance capturing molecules 7613 bound to gate electrode 7614 may be different each other. This allows detection of several types of detection target substances containing one sample solution 7615. FIG. 48A shows a state where sample solution 7615 is present on a plurality of gate electrodes 7614.

To detect a detection target substance by the biosensor device shown in FIG. 48A, sample solution 7615 is dropped on to gate electrode 7614 (and is dried depending on the case may be), element section 7602 is mounted to biosensor device body 7601, and then a voltage is applied to each element. With these operations, changes in source-drain current of element section 7605 are caused by, for example, molecular interaction on gate electrode 7614. These changes are displayed on display section 7604.

FIG. 48B is a view showing one example of element section 7602 of the biosensor device shown in FIG. 48A. Element section 7602 is preferably constructed in chip form. FIG. 48B is a plan view showing chip 7702 of the biosensor device.

Chip 7702 includes case 7703, and element section 7602 which is accommodated therein. Element section 7602 includes four gate electrodes 7614 each disposed adjacently, source electrode 7610, drain electrode 7611, and ultra fine fiber. Each gate electrode 7614 is connected by bonding to conductive pin 7704 fixed to case 7703 side part.

When chip 7702 onto which sample solution is dropped (and is dried depending on the case may be) is mounted to biosensor device body 7601 with conductive pin 7704 located beneath, conductive pins 7704 connected to each of electrodes are connected to power supply 7603 of device body 7601.

As shown in FIG. 48B, when ends of four gate electrode 7614 are disposed adjacently so that all may be located at center part, detection of multiple items can be performed at one time by dropping the sample solution to the center part thereof. Similarly, each of gate electrodes may be disposed in fan shape and assembly of gate electrodes may be disposed to be a nearly circular form.

(C) Biosensor Device Having Gate Element Section of Separate-Gate FET of the Present Invention at Element Section In the present embodiment, the biosensor device body includes a power supply, a display section, and an ultra fine fiber element section of separate-gate FET of the present invention. The power supply may be substituted with external power acquisition means for acquiring electric power from the outside. Further, the display section may be replaced by external output type. The source electrode, drain electrode, and channel in the ultra fine fiber element are electrically connected to the power supply.

In the present embodiment, the element section includes a gate element section of separate-gate FET of the present invention, and a detection target substance capturing molecule bound to the gate element section. The gate element section used in the element section can assume any of the embodiments of gate element section. When the element section is mounted to the biosensor device body, gate electrode in the element section can be electrically connected to the power supply in the biosensor device body, the second substrate can be electrically connected to the substrate of the ultra fine fiber element section in the biosensor device body.

Site on the gate element section of separate-gate FET of the present invention to which the detection target substance capturing molecule is bound is, as mentioned previously, gate electrode, insulating film of first plane (plane onto which gate electrode is disposed) of second substrate, or the like, while gate electrode is preferable. This is because when the detection target substance capturing molecule is only on the electrode, image charge thereof is generated only in the electrode, and interference with image charges in other electrodes hardly occur. Further, as will be described later, detection of multiple items can be performed by providing multiple gate electrodes and by binding each different detection target substance capturing molecules thereto.

The gate electrode may be disposed directly to the second substrate or disposed apart from the second substrate. The number of gate electrodes may be, as mentioned previously, one or more.

FIG. 49 and FIG. 50 are drawings showing one example of the biosensor device having gate element section at element section.

In FIG. 49A, the biosensor device includes biosensor device body 7601, and element section 7802 disposed at upper part of the biosensor device body.

Biosensor device body 7601 includes power supply 7603, display section 7604, and ultra fine fiber element section 7801.

Ultra fine fiber element section 7801 includes substrate 7609 and ultra fine fiber element 7605, and is disposed to conductive substrate 7803b. Substrate 7609 is composed of support substrate 7608, first insulating film 7607, and second insulating film 7616. Further, ultra fine fiber element 7605 is composed of source electrode 7610 and drain electrode 7611 disposed on first insulating film 7607, and ultra fine fiber 7612 electrically connecting source electrode 7610 and drain electrode 7611. Source electrode 7610 and drain electrode 7611 are connected to power supply 7603 and voltage thereof is controllable.

Element section 7802 is detachable to and from biosensor device body 7601, and includes second substrate 7620, a plurality of electrodes 7614, and detection target substance capturing molecule 7613, and is disposed to conductive substrate 7803a. Further, second substrate 7620 is composed of second support substrate 7617, third insulating film 7618 located on first plane of second support substrate 7617, and fourth insulating film 7619 located on second plane of second support substrate 7617. Gate electrode 7614 is, when element section 7802 is mounted to biosensor device body 7601, connected to power supply 7603 and voltage thereof is controllable. Further, when connected to biosensor device body 7601, element section 7802 can be electrically connected to ultra fine fiber element section 7801 via conductive substrates 7803a, 7803b.

On gate electrode 7614 disposed on third insulating film 7618 are bound detection target substance capturing molecules 7613 each specifically reacts with detection target substances. In this case, detection target substance capturing molecules 7613 bound to gate electrode 7614 may be different each other. This allows detection of several types of detection target substances containing one sample solution 7615. FIG. 49A shows a state where sample solution 7615 is present on a plurality of gate electrodes 7614.

To detect a detection target substance by the biosensor device shown in FIG. 49A, sample solution 7615 is dropped on to gate electrode 7614 (and is dried depending on the case may be), element section 7802 is mounted to biosensor device body 7601, and then a voltage is simply applied to each element. With these operations, changes in source-drain current of ultra fine fiber element section 7801 are caused by, for example, molecular interaction on gate electrode 7614. These changes are displayed on display section 7604.

With biosensor device shown in FIG. 49A, ultra fine fiber element section 7801 is separated from gate element section included in element section 7802, and is disposed inside biosensor device body 7601. Since element section 7802 is detachable to and from biosensor device body 7601, ultra fine fiber element section 7801 need not undertake physical and chemical burdens. Therefore, operating life of ultra fine fiber element section 7801 is lengthened remarkably. For this reason, when characteristics of ultra fine fiber element section 7801 are once measured and a calibration curve specific to ultra fine fiber element section 7801 is prepared, it is possible to detect concentration of a detection target substance of unknown sample from the calibration curve. Since a detection target substance can be detected using one ultra fine fiber element section 7801 and replacing detection target substance recognizing element section 7802 in each detection, ultra fine fiber element section 7801 can be used for long time, and detection target substance recognizing element section 7802 can also be handled as disposable.

Position of ultra fine fiber element section 7801 inside biosensor device body 7601 is not specifically limited, as long as, when element section 7802 is mounted, conductive substrate 7803b of ultra fine fiber element section 7801 and conductive substrate 7803b of element section 7802 are electrically connected. For example, such a configuration may be used that ultra fine fiber element section 7801 is disposed in advance at upper part of biosensor device body 7601 with conductive substrate 7803b faced upwardly, and when element section 7802 is mounted, conductive substrate 7803b and conductive substrate 7803a make contact and are connected (see separate-gate FET shown in FIG. 43).

FIG. 49B and FIG. 49C are drawings showing one example of element section 7802 of biosensor device shown in FIG. 49A. Element section 7802 is preferably constructed in chip form. FIG. 49B and FIG. 49C are perspective view and cross-sectional view of chip 7804 of the biosensor device shown in FIG. 49A, respectively.

Chip 7804 includes case 7703 and element section 7802 being accommodated therein. Element section 7802 has four gate electrodes 7614 disposed adjacently and is mounted to conductive substrate 7803. Each of gate electrodes 7614 is connected by bonding to conductive pin 7704 fixed to case 7703 side part, and conductive substrate 7803 is connected to another conductive pin 7704.

When chip 7804 onto which sample solution is dropped (and is dried depending on the case may be) is mounted to biosensor device body 7601 with conductive pin 7704 located beneath, each of conductive pins 7704 is connected to power supply 7603 of biosensor device body 7601 and conductive substrate 7803b to which is mounted ultra fine fiber element section 7801.

As shown in FIG. 49B, since ends of four gate electrode 7614 are disposed adjacently so that all may be located at center part, detection of multiple items can be performed at one time by dropping the sample solution to the center part. Each of gate electrodes may be disposed in fan shape and assembly of the gate electrodes may be disposed to be a nearly circular form. These features will be explained later.

The biosensor device shown in FIG. 50 is composed of biosensor device body 7601, and element section 7802 disposed inside of the biosensor device body. An aspect that biosensor device body 7601 includes ultra fine fiber element section 7801, power supply 7603, and display section 7604 is same as that of the biosensor device shown in FIG. 49. With the biosensor device shown in FIG. 50, element section 7802 is detachable to and from biosensor device body 7601, when moved in arrow A direction.

When element section 7802 is mounted to biosensor device body 7601, gate electrode 7614 can be electrically connected to power supply 7603, and conductive substrate 7803a can be electrically connected to conductive substrate 7803b of ultra fine fiber element section 7801.

FIG. 50B and FIG. 50C are perspective view and cross-sectional view of chip 7804 of the biosensor device shown in FIG. 50A, respectively. Chip 7804 includes case 7703, and element section 7802 accommodated therein. Element section 7802 has four gate electrodes 7614 disposed adjacently and is mounted to conductive substrate 7803a. Each of gate electrodes 7614 is connected to plate electrode 7901 formed on case 7703 side part. Further, conductive substrate 7803a is connected to another plate electrode 7901.

When chip 7804 onto which sample solution 7615 is dropped (and is dried depending on the case may be) is mounted in insertion fashion to device body 7601 with plate electrode 7901 located front, plate electrode 7901 can be connected to power supply 7603 of device body 7601 and conductive substrate 7803b of ultra fine fiber element section 7801.

As shown in FIG. 50B, since ends of four gate electrode 7614 are disposed adjacently so that all may be located at center part, detection of multiple items can be performed at one time by dropping the sample solution to the center part. Each of gate electrodes may be disposed in fan shape and assembly of the gate electrodes may be disposed to be a nearly circular form. In either case, all gate electrodes 7614 and plate electrode 7901 disposed in parallel at one end of the case are connected, while all pathways from gate electrode 7614 to end plate electrode 7901 are preferably laid outside the assembly of gate electrodes 7614. With this arrangement of the pathways, ends of a plurality of gate electrodes 7614 can be made closer around center part adjoining each other.

[Description of Chip]

As shown in FIG. 49 and FIG. 50, the biosensor device of the present invention may include chip 7804 including gate element section of separate-gate FET of the present invention, which is detachable to and from the biosensor device boy. FIG. 51 is a view showing an example of chip 7804. A detection target substance can be detected by dropping the sample solution to the gate electrode.

Figure 51A:
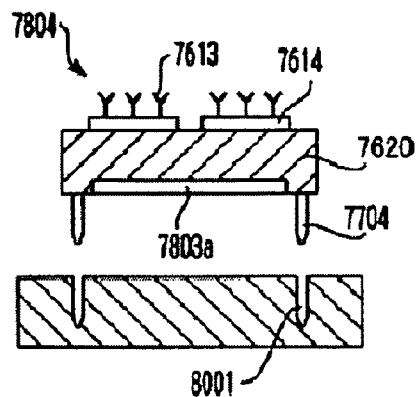

In FIG. 51A, chip 7804 includes conductive substrate 7803a, gate electrode 7614, and detection target substance capturing molecule 7613 bound to electrode 7614. Conductive substrate 7803a and gate electrode 7614 in chip 7804 are electrically connected to connection terminal 8001 of the device body via conductive pin 7704.

Chip 7804 shown in FIG. 51A may include a plurality of gate electrodes 7614. In this case, detection of multiple items for one analyte can be performed by binding each different detection target substance capturing molecules 7613 to one of gate electrodes 7614 and by applying a voltage to each of gate electrodes 7614.

Figure 51B:
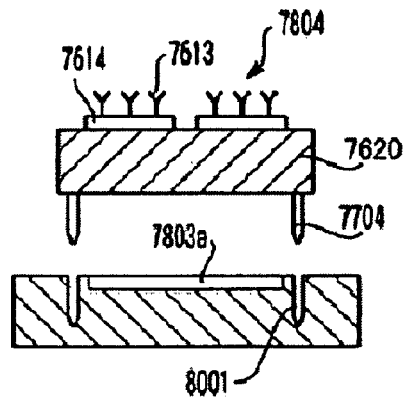

In FIG. 51B, chip 7804 has gate electrode 7614 and detection target substance capturing molecules 7613 bound to gate electrode 7614. Conductive substrate 7803a is disposed to the biosensor device body. Conductive substrate 7803a and gate electrode 7614 in chip 7804 are connected to connection terminal 8001 of the device body via conductive pin 7704. In this example, since conductive substrate 7803a is disposed to the biosensor device body, preparation costs of chip 7804 can be reduced further.

Figure 51C:
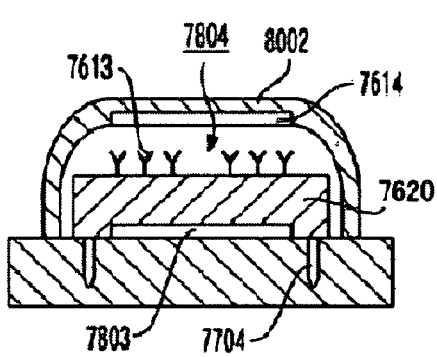

In FIG. 51C, chip 7804 includes conductive substrate 7803a, and detection target substance capturing molecule 7613 bound to second substrate 7620. Gate electrode 7614 is disposed to cover 8002 which covers chip 7804 of the biosensor device body.

Figure 51D:
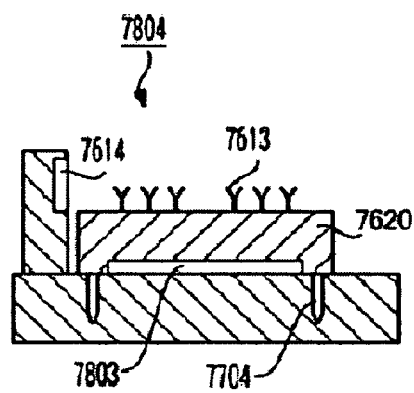

In FIG. 51D, chip 7804 includes conductive substrate 7803a, and detection target substance capturing molecule 7613 bound to second substrate 7620. Gate electrode 7614 is disposed to the biosensor device body so as to be lateral to chip 7804.

The example of the chip shown in FIG. 51 is based on that a small amount of sample solution is dropped with a micropipette and hence, it has plane shape. When the sample solution is large in quantity, there is a possibility that sample solution spills from the chip thereby contaminating surrounding area. Therefore, when quantity of the sample solution is large, profile of the chip is preferably concave in lieu of plane shape.

FIG. 52 is a view showing an example of chip having concave shape. FIG. 52A is a perspective view showing one example of a chip having concave shape. FIG. 52B and FIG. 52C are cross-sectional view showing examples of a chip having concave shape.

In FIG. 52A, chip 8101 has a concave. Four gate electrodes 7614 are disposed on the bottom of the concave, and conductive substrate 7803a is provided thereunder separated by an insulating plate such as plastic. Conductive substrate 7803a may be provided to chip 8101 as shown in FIG. 52B, or provided to the biosensor device body as shown in FIG. 52C.

Different detection target substance capturing molecules may be bound respectively to gate electrode 7614. To detect a detection target substance, for example, a voltage is simply applied to gate electrode 7614 and source-drain current is then measured. Detection of multiple items for one analyte is possible by performing the same measurement for each of four gate electrodes 7614.

When each of gate electrodes 7614 of the chip shown in FIG. 51A is connected sequentially to one ultra fine fiber element section, detection can be made sequentially for different detection target substances. Further, when each of gate electrodes 7614 is connected at once to each of a plurality of ultra fine fiber element sections, several types of detection target substances can be detected simultaneously.

A chip having a concave is able to hold sample solution on the gate element section with stable manner, and is preferably applied to portable biosensor apparatus which is used outdoor or at routine clinical practice. Further, when a chip is marked with a scale, it is possible to add a constant amount of sample without the use of micropipette. Moreover, when a cover is provided to the chip, evaporation of the sample can be prevented, and noises generated can be reduced by exerting a pressure to sample solution by the cover.

In addition, the chip may be of microplate chip. The microplate chip enables detection of multiple items of multiple analytes. FIG. 53 is a view showing an example of microplate chip.

FIG. 53A is a perspective view showing one example of microplate chip with 24-wells. In FIG. 53A, four gate electrodes are provided on the bottom of each well of chip 8201, and a conductive substrate is provided thereunder separated by an insulating plate such as plastic. Each gate electrode and conductive substrate are electrically connected to a conductive pin, respectively. By inserting chip 8201 into socket 8202 of the biosensor device body, each gate electrode is electrically connected to the power supply in the biosensor device body, and each conductive substrate can be electrically connected to conductive substrate of the ultra fine fiber element section.

FIG. 53B is a perspective view showing another example of microplate chip with 24-wells. As shown in FIG. 53B, when electric connection part 8203 with the biosensor device body is provided at side surface of chip 8201, chip 8201 can be inserted to side part of the biosensor device body.

FIG. 53C is a cross-sectional view showing one example of wirings in chip 8201 shown in FIG. 53B. Since a voltage should be impressed at different times, all gate electrodes 7614 need specific electric circuit. Meanwhile, conductive substrate 7803b may require one common circuit.

To four gate electrodes 7614 present in each of wells of microplate chip 8210 with 24-wells is bound each different detection target substance capturing molecules 7613. To detect a detection target substance, for example, a voltage is simply impressed to one gate electrode 7614 and source-drain current is then measured. Detection of four items becomes possible for each of 24 analytes by performing this measurement for each of gate electrodes.

Further, different detection target substances can be detected sequentially by connecting sequentially each of gate electrodes 7614 to one ultra fine fiber element section. Further, simultaneous detection of a plurality of detection target substances is possible by connecting each of gate electrodes 7614 simultaneously to each of a plurality of ultra fine fiber element sections.

Number of wells of microplate chip and of gate electrodes can be selected appropriately. For example, when the number of detection items needs to be increased, the number of gate electrodes per well can be increased. In this case, for example, bottom area can be widened with the use of 6-well microplate instead of 24-wells. If the number of analytes needs to be increased, for example, a microplate with more wells (e.g., 96-well microplate) can be used.

In FIG. 53, although conductive substrate 7803a is included in the microplate, it may be located at biosensor device body side, as long as positioned immediately underneath each of wells.

Further, the chip may include a flow cell that serves as a microchannel and sample solution may be supplied thereto by a pump, or the like. In this case, detection target substance capturing molecule is bound to flow cell interior surface. With the use of a recognizing chip having flow cell, an integration detection system referred to as μ-TAS (Micro Total Analysis System) can be constructed.

FIG. 54A is a view showing one example of a chip including back-gate FET of the present invention, in which a flow cell is provided. Detection target substance capturing molecule 7613 is bound to second insulating film 7616 constituting upper plane of the flow cell. This example illustrates such an aspect that sample solution 7615 is supplied continuously from the left into flow cell by sample solution supplying section such as pump (not shown). Amount of supplying of sample solution 7615 is regulated by sample solution supplying section, and therefore, users are not required to measure the amount of sample solution 7615 using a pipette, or the like, but to supply sufficient amount of sample solution 7615 to the sample solution supplying section.

FIG. 54B is a view showing one example of a chip including gate element section of separate-gate FET of the present invention, in which a flow cell is provided. Detection target substance capturing molecule 7613 is bound on a plurality of gate electrodes 7614 located on the bottom of the flow cell. In this example, detection can be possible for a plurality of items.

In addition, μ-TAS and liquid chromatography may be combined. For example, for fractions after treated by column of liquid chromatography, detection can be made by UV and by the biosensor of the present invention. In this way, with the use of μ-TAS, a same sample is introduced to other detection device or to other detection site of a composite device, and detection of several types of detection target substances can be carried out in succession. Moreover, use of μ-TAS allows chronological detection.

As mentioned previously, the biosensor of the present invention is capable of detecting a detection target substance from changes in source-drain current. Source-drain current necessary for this detection may normally be μA order. Therefore, sufficient detection sensitivity is obtainable with measurement accuracy of ordinary circuit tester (several hundred nA) without the use of expensive instruments such as semiconductor parameter analyzer. Accordingly, biosensor device which can be driven by a battery for notebook type personal computer (see FIG. 55A) or small-sized biosensor driven by a small sized battery (see FIG. 55B) can be produced. Moreover, since special detection device is not required necessarily, it can be downsized to cellular phone size.

2-4. Detection by Biosensor of the Present Invention

As mentioned previously, a detection target substance can be detected with the use of biosensor (device) of the present invention. The biosensor of the present invention detects a detection target substance from changes in source-drain current or source-drain voltage generated by binding the target substance to the detection target substance capturing molecule.

The following description shows outline of detection procedures. Explanation will be given for a case where a solution is used as the sample.

(1) In the biosensor, sample solution is added to a site where detection target substance capturing molecule is bound. For example, sample solution may be added to reverse side of the substrate (on second insulating film) to which is bound detection target substance capturing molecule. When the sample solution includes the detection target substance, interaction between detection target substance and detection target substance capturing molecule (e.g., antigen-antibody reaction) occurs.

(2) Since solvent (e.g., water) contained in the sample solution thus added gives influence on source-drain current, noises may, in some cases, be generated at detection. The following methods are mentioned for reduction of noises:

(2-a) The sample solution added is eliminated by evaporation. Although the method for elimination by evaporation is not specifically limited, for example, blowing using nitrogen gas, or heater or thermoelectric conversion element (Peltier element) may be utilized. With evaporation by blowing, it is preferable to obtain a uniform thin-film state through gentle evaporation while directing blowing thereto. Therefore, spraying with the use of ordinary spray can may be used, but controls of amount of gas and intensity of flow are difficult, in some cases.

(2-b) The sample solution added is cooled. On this occasion, it preferably becomes insulating by being frozen. Although the cooling method is not specifically limited, for example, thermoelectric conversion element (Peltier element) or liquid nitrogen may be employed.

(3) Gate electrode is put to the site where the sample solution is added (preferably, after sample solution is evaporated or cooled) to energize FET. I-V characteristics or I-Vg characteristics are then measured.

Detection method by the biosensor of the present invention and detection results will be explained briefly. In particular, (A) Detection of nickel ion (divalent ion), (B) Detection of anti-hemagglutinin (hereafter referred to as "HA") antibody, (C) Detection of anti-calmodulin (hereafter referred to as "CaM") antibody, will be explained. In either example, back-gate FET of the present invention is used.

Back-gate FET of the present invention used in the following detection examples (A) through (C) has a configuration shown in FIG. 31A. In FET used in the measurement, support substrate was silicon substrate 500 μm in thickness, first insulating film and second insulating film were silicon oxide 300 nm in thickness, area of substrate was 1 cm$^2$ (1 cm×1 cm), ultra fine fiber is single-walled CNT, interval between source electrode and drain electrode was 5 μm, area of second insulating film contacting gate electrode was 1 cm$^2$. Further, it was confirmed by AFM that the source electrode and drain electrode were connected by several CNTs.

(A) Detection of Nickel Ion

First, silicon oxide film surface (1 cm$^2$) of second plane (the plane on which neither source electrode, drain electrode, nor channel is disposed) of back-gate FET substrate prepared was washed with piranha solution and ethanol, and dried. Next, 3 μl of mercaptopropyl trimethoxysilane (S810) was dropped on this silicon oxide film surface, and heated at 180° C. for two hours. After cooled to 30° C., treated with 50 mM of dithiothreitol (DTT) at the same temperature for not less than one hour, and then washed with water.

Here, a probe connected to semiconductor parameter analyzer was connected to the source electrode and drain electrode to measure I-V characteristics. I-V characteristics curve (which shows relationship between source-drain current and source-drain voltage) was obtained with gate voltage set to 0 V.

Next, maleimide-NTA solution (1 mg/ml) prepared using 10 mM of phosphate buffer solution (pH 6.5) was piled-up onto the silicon oxide film surface, and allowed to stand at room temperature for one hour. Following this, the obtained substrate was washed with water and dried under nitrogen gas (dried till water droplet is no more visible). Then, I-V characteristics curve was obtained with a similar manner as mentioned.

Further, 50 μl of NiCl$_2$ solution (50 mM) was dropped onto the silicon oxide film surface. After allowed to stand for 15 minutes, the obtained substrate was washed with water, and dried under nitrogen gas (dried till water droplet is no more visible). Then, I-V characteristics curve was obtained as mentioned.

FIG. 56 shows results obtained. In FIG. 56, "di" means I-V characteristics curve prior to NTA binding, "nta" means I-V characteristics curve after NTA binding, "ni" means I-V characteristics curve after dropping of solution containing nickel ion. As shown in FIG. 56, it is known that, in either case, source-drain current increases as source-drain voltage increases. Further, in either case, changes in source-drain current are less significant while source-drain voltage is around 0 V, and semiconductor specific properties are observed. Further, it is noticed that source-drain current is increased on "ni" as compared to "nta". Accordingly, it is known that nickel ion can be detected by the biosensor of the present invention to which NTA is bound as the detection target substance capturing molecule. Moreover, it is suggested that divalent ion (zinc ion, cobalt ion, or the like), which exhibits interaction with NTA, as well as nickel ion are detectable.

(B) Detection of Anti-Hemagglutinin Antibody

First, recombinant hemagglutinin (hereafter abbreviated as "rHA") protein that is antibody capturing molecule used as the detection target substance capturing molecule was prepared. Specifically, this is a recombinant HA protein, in which histidine tag is added to C-terminal thereof. Expression of proteins truncated at various levels (1-220, 1-250, 1-290, 1-320; numerals denote amino acid residue numbers on the primary sequence) was attempted.

rHA protein expression plasmid corresponding to each level was introduced to 293T cells. Using monoclonal antibody E2/3 and polyclonal antibody, expression of rHA protein in the cells was confirmed. Further, it was confirmed by Western blot method that rHA protein was secreted in supernatant.

Large quantity expression occurred in $rHA_{1-290}$ and $rHA_{1-220}$. Secretions in the supernatant were purified by NTA-$Ni^{2+}$ column, respectively. Fractions containing target rHA protein were confirmed by ELISA and Western blot method, and were fractionated. Fractionates were dialyzed in PBS to yield rHA proteins. Among $rHA_{1-290}$ and $rHA_{1-220}$, $rHA_{1-220}$ was not reactive with monoclonal antibody, and therefore, $rHA_{1-290}$ was used as the detection target substance capturing molecule.

Further, hybridoma culture supernatant stock solution of anti-HA antibody (E2/3) was diluted to $1\times10^{-5}$, $1\times10^{-6}$, $1\times10^{-7}$, $1\times10^{-8}$, $1\times10^{-10}$ to yield dilution solution, respectively.

With a similar manner as used for nickel ion detection, maleimide-NTA was bound to second plane of back-gate FET substrate prepared and was further treated with $NiCl_2$. Here, I-V characteristics curve was obtained as mentioned previously (however, gate voltage was set to −20 V).

Each of HA-antibody dilution solutions (50 μl) mentioned above was added thereto, allowed to stand at 25° C. for 15 minutes, washed with water, and dried under nitrogen gas (dried till water droplet is no more visible). Here, I-V characteristics curve was obtained as mentioned above (however, gate voltage was set to −20 V).

Next, $rHA_{1-290}$ (1.9 μg/ml; 50 μl) obtained as mentioned previously was dropped onto second plane of the substrate treated with $NiCl_2$, and immobilized. Here, I-V characteristics curve was obtained as mentioned above (however, gate voltage was set to −20 V).

Each of the dilution solutions (50 μl) was added onto second plane of the substrate to which is immobilized $rHA_{1-290}$, allowed to stand at 25° C. for 15 minutes, washed with water, and dried under nitrogen gas (dried till water droplet is no more visible). Here, I-V characteristics curve was obtained as mentioned above (however, gate voltage was set to −20 V).

I-V characteristics curves thus obtained are shown in FIGS. 57 through 62.

FIG. 57 shows I-V characteristics curve (dotted line) obtained when second plane of the substrate was treated with $NiCl_2$, and I-V characteristics curve (solid line) obtained when $rHA_{1290}$ was immobilized to second plane of $NiCl_2$ treated substrate.

FIG. 58 shows I-V characteristics curve (dotted line) obtained from a case where second plane of the substrate is treated with $NiCl_2$ and then $1\times10^{-10}$ dilution solution is added to the second plane, and I-V characteristics curve (solid line) obtained from a case where $rHA_{1-290}$ is immobilized to second plane of the substrate treated with $NiCl_2$ and then $5\times10^{-5}$ dilution solution is added to the second plane.

FIG. 59 shows I-V characteristics curve (dotted line) obtained from a case where second plane of the substrate is treated with $NiCl_2$ and then $1\times10^{-8}$ dilution solution is added to the second plane, and I-V characteristics curve (solid line) obtained from a case where $rHA_{1-290}$ is immobilized to second plane of the substrate treated with $NiCl_2$ and then $5\times10^{-8}$ dilution solution is added to the second plane.

FIG. 60 shows I-V characteristics curve (dotted line) obtained from a case where second plane of the substrate is treated with $NiCl_2$ and then $1\times10^{-7}$ dilution solution is added to the second plane, and I-V characteristics curve (solid line) obtained from a case where $rHA_{1-290}$ is immobilized to second plane of the substrate treated with $NiCl_2$ and then $5\times10^{-7}$ dilution solution is added to the second plane.

FIG. 61 shows I-V characteristics curve (dotted line) obtained from a case where second plane of the substrate is treated with $NiCl_2$ and then $1\times10^{-6}$ dilution solution is added to the second plane, and I-V characteristics curve (solid line) obtained from a case where $rHA_{1-290}$ is immobilized to second plane of the substrate treated with $NiCl_2$ and then $5\times10^{-6}$ dilution solution is added to the second plane.

FIG. 62 shows I-V characteristics curve (dotted line) obtained from a case where second plane of the substrate is treated with $NiCl_2$ and then $1\times10^{-5}$ dilution solution is added to the second plane, and I-V characteristics curve (solid line) obtained from a case where $rHA_{1-290}$ is immobilized to second plane of the substrate treated with $NiCl_2$ and then $5\times10^{-5}$ dilution solution is added to the second plane.

As shown in FIG. 57 through FIG. 62, when source-drain voltage is from 0 to 1 V, there is a little difference in source-drain current regardless of the presence or absence of $rHA_{1-290}$ immobilized to second plane of the substrate. Meanwhile, it is known that, when source-drain voltage starts to exceed 1 V, and there is $rHA_{1-290}$ immobilized to reverse side of the substrate, current value sharply increases. This finding suggests that detection of anti-HA antibody is possible even in higher dilution ratio region.

(C) Detection of Anti-Calmodulin Antibody

For anti-CaM antibody, detection results from independent two cases will be shown.

First, recombinant CaM (hereafter abbreviated to as "rCaM"), that is antibody capturing molecule, was prepared to be used as the detection target substance capturing molecule.

rCaM expression vector was constructed by inserting DNA fragment containing cDNA of rat CaM gene into SacI-XbaI site of the expression vector pBAD/gIII (supplied by Invitrogen Inc.). The expression vector thus constructed was introduced into *Escherichia coli* LMG194 strain to yield rCaM expression clone. The clone obtained was inoculated to 2 ml of LB/ampicillin medium and incubated overnight.

5 mL of culture thus obtained was seeded to LB/ampicillin medium and subjected to shaking culture at 37° C. till OD600 became 0.5. Following this, L-arabinose was added to give a final concentration of 0.02% and shaking incubated further at 37° C. for four hours.

Cultures obtained were harvested by centrifugation, suspended in Native Binding Buffer (supplied by Invitrogen Inc.), subjected to ultrasonication, and partly purified using Probond™ Purification System (supplied by Invitrogen Inc.).

Further, purified uniformly in SDS-PAGE fashion using HiLoad 26/60 Superdex 75 pg (Amasham BioScience) to obtain rCaM protein in which histidine tag is added to C-terminal thereof.

In the meantime, a dilution solution of mixed solution of anti-CaM monoclonal antibody 6D4, 1F11 and 2D1 (supplied by Sigma) was prepared using PBS. Dilution series used was $1\times10^{-11}$, $1\times10^{-10}$, $1\times10^{-9}$, $1\times10^{-8}$, $1\times10^{-7}$, $1\times10^{-6}$, $1\times10^{-4}$ of each anti-CaM monoclonal antibody stock solution.

Likewise nickel ion detection case mentioned previously, maleimide-NTA was bound to second plane of the substrate of back-gate FET prepared, and then treated with $NiCl_2$. Here, I-V characteristics curve was obtained as mentioned previously (however, gate voltage was set to $-20$ V)

rCaM protein (12 μg/ml; 50 μl) in PBS was added to second plane treated with $NiCl_2$ and immobilized. Here, I-V characteristics curve was obtained as mentioned previously (however, gate voltage was set to $-20$ V).

Each of the dilution solutions (50 μl) of anti-CaM monoclonal antibody was added to the substrate where rCaM protein was immobilized, allowed to stand at 25° C. for 15 minutes, washed with water, and dried under nitrogen gas (dried till water droplet is no more visible). Here, I-V characteristics curve was obtained as mentioned previously (however, gate voltage was set to $-20$ V).

Meanwhile, as the control, bovine serum albumin (BSA) (34 mg/ml; 50 μl) was added to the substrate where rCaM protein was immobilized, allowed to stand at 25° C. for 15 minute, washed with water, and dried under nitrogen gas (dried till water droplet is no more visible). Here, I-V characteristics curve was obtained as mentioned previously (however, gate voltage was set to $-20$ V).

FIG. 63 shows source-drain current for each of I-V characteristics curves thus obtained when source-drain voltage is 1.5 V. In FIG. 63, "Ni" means source-drain current when treated with $NiCl_2$, "CaM" means source-drain current when rCaM protein is immobilized, "BSA" means source-drain current when bovine serum albumin (control) was added, and "$10^{-11}$ to $10^{-4}$" means source-drain current when antibody dilution solution of each concentration was added.

It is known from FIG. 63 that as concentration of anti-CaM antibody increases ($10^{-11}$ to $10^{-8}$), source-drain current increases. However, when concentration of anti-CaM antibody exceeds a certain level (i.e., higher than $10^{-8}$), association with source-drain current is no more recognized.

Further, as shown in FIG. 63, changes in source-drain current were not noticed when BSA was added. Therefore, it is known that anti-CaM antibody is specifically detected.

FIG. 63 also shows results of detection of anti-CaM antibody using ELISA. Using 100 μl of rCaM solution (5 μg/ml), rCaM was adsorbed and immobilized to each well of the microtiter plate. Mixture of the primary antibodies was diluted to each dilution ratio, placed into each well and allowed to stand for one hour, then washed with PBST (PBS containing 0.2% Triton X-100), secondary antibody diluted 5000-fold (HRP labeled anti-mouse IgG antibody) was then added to each well, allowed to stand again for one hour, washed with PBST, a substrate having absorption wavelength of 450 nm was generated by TMB coloring substance, and then absorbance was measured.

As shown in FIG. 63, it is understood that the detection method of the present invention has detection sensitivity as high as 400 thousand times as compared to detection limit of anti-CaM antibody ($10^{-6}$ dilution solution) by ELISA.

FIG. 64 shows I-Vg characteristics when dilution ratios of the antibody stock solution are varied. In the FIGURE, (a) shows I-Vg characteristics curve for dilution ratio $10^{-10}$ of antibody stock solution, (b) shows I-Vg characteristics curve for dilution ratio $10^{-9}$ of antibody stock solution, (c) shows I-Vg characteristics curve for dilution ratio $10^{-5}$ of antibody stock solution. It should be noted that detection results shown in FIG. 63 and detection results shown in FIG. 64 are obtained by independent experiments, respectively. It is noticed that as dilution ratio of the antibody stock solution increases, source-drain current increases.

3. Measurement of Concentration of Detection Target Substance of the Present Invention The biosensor of the present invention can be used for measurements of concentrations of detection target substances. When a concentration is measured, it is preferable to provide (1) A storage section that stores a calibration curve which shows relationship between concentration of detection target substance and a predetermined characteristic value, and (2) A concentration determination section that determines concentration of detection target substance contained in unknown sample using the calibration curve. "Predetermined characteristic value" may be arbitrary value as long as it is in 1:1 relationship with the concentration.

The present inventors found that a predetermined value in I-V characteristics curve (a curve showing relationship between source-drain current and source-drain voltage when gate voltage is kept at constant) or in I-Vg characteristics curve (a curve showing relationship between source-drain current and gate voltage when source-drain voltage is kept at constant) has a definite correlation with sample concentration. Therefore, example of "predetermined characteristic value" includes predetermined value in I-V characteristics curve or I-Vg characteristics curve. In the example of "predetermined value in I-Vg characteristics curve" is included source-drain current or gate voltage at inflection point of I-Vg characteristics curve.

FIG. 65 shows an example of a graph showing relationship between concentration of a detection target substance in a sample and source-drain current at inflection point of I-Vg characteristics curve obtained from the sample by the biosensor according to the present invention. As shown in FIG. 65, logarithm of the sample concentration and the current value can be proportional relationship. The area in which this proportional relationship is established can be used as a calibration curve.

When concentration of a detection target substance exceeds a certain level, the concentration and the current value no more exhibit proportional relationship. This is because, as shown in FIG. 66, concentration of the detection target substance becomes excessively high with regard to the number of the detection target substance capturing molecules being bound to the biosensor.

The biosensor for concentration measurement is preferably equipped with a concentration determination section that determines a concentration based on the calibration curve. The concentration determination section is preferably equipped with a section that measures "predetermined characteristic value" for unknown sample and a concentration computation section by applying the measured "predetermined characteristic value" to the stored calibration curve.

The biosensor for concentration measurement may be further equipped with a calibration section that obtains a calibration curve. The calibration section obtains a calibration curve using not less than three known samples in which each of concentration is different each other (sample concentration of detection target substance thereof is known). That is, concentration and "predetermined characteristic value" are obtained for three samples, and a calibration curve is obtained therefrom.

FIG. 67 is a view showing one example of biosensor device for measuring concentration of a detection target substance. In FIG. 67, biosensor device 1100 includes biosensor body section 1110, computer 1120, and D/A (digital-analog) converter 1130. Biosensor body section 1110 includes FET of the present invention to which is bound detection target substance capturing molecule. In this example, separate-gate FET of the present invention is included.

Computer 1120 includes, for example, personal computer (PC) or exclusive computing machine, or the like. D/A converter 1130 has functions to convert digital signal to analog signal and to convert analog signal to digital signal. Digital signal from computer 1120 is converted to analog signal by D/A converter 1130 and controls voltages impressed to biosensor body section 1110 (gate voltage, source-drain voltage). Further, drain current value (source-drain current) of biosensor body section 1110 is taken into computer 1120 by D/A converter 1130.

Computer 1120 includes CPU, memory, and display section (not shown), and has calibration function for determining calibration curve and measurement function for measuring unknown sample. In the measurement of unknown sample, concentration of a target in unknown sample is measured.

Now, calibration function of biosensor device 1100 shown in FIG. 67 will be explained.

FIG. 68 is a flowchart showing one example of processing procedures of the calibration function. This flowchart is stored in the memory of computer 1120 as the control program and is executed by CPU.

First, in step S2000, I-Vg characteristics (relationship between source-drain current and gate voltage) are measured. For example, after a sample of known dilution ratio is dropped, source-drain voltage is fixed to a predetermined value (e.g., −1 V), gate voltage is varied every predetermined value (e.g., 0.1 V) within a predetermined range (e.g., from −1 V to +10 V), and source-drain current (Isd) is measured and recorded each time. I-Vg characteristics for certain dilution ratio are obtained by this manipulation. Measurement processing of I-Vg characteristics will be dealt with later referring to FIG. 69.

In step S2100, inflection point of the I-Vg characteristics obtained in step S2000 is determined. This inflection point is one of features of I-Vg characteristics and is inflection point of changes in source-drain current with regard to gate voltage. Changes are most remarkable (sharp inclination) at this inflection point in I-Vg characteristics, and characteristics changes are most intensive at this portion in the dynamic range, and therefore, it is expected that most sensitive detection results may result against changes. Inflection point determination processing will be described later referring to FIG. 70.

In step S2200, whether or not dilution ratio should be changed is determined. This determination is performed according to manual operation by users or according to a signal from μ-TAS system. In other words, not less than three points should be plotted on the graph for determination of a calibration curve, and therefore, measurement of I-Vg characteristics and determination processing of inflection point should be carried out for not less than three samples in which each of dilution ratio is known and different each other. Then, in the step S2000, determination is made for all scheduled known samples whether or not the processing is completed. As a result of the determination, when dilution ratio is changed (S2200: YES), it is determined that unprocessed known sample is present, it returns to step S2000, performs a series of the processing for the unprocessed known sample, and when dilution ratio is not changed (S2200: NO), it is determined that unprocessed known sample is not present, and it proceeds to step S2300.

In step S2300, calibration curve is determined based on results of processing of step S2000 through S2200, thereby completing the flow. Calibration curve determination processing will be described later referring to FIG. 71.

Next, I-Vg characteristics measurement processing (step S2000) will be explained.

FIG. 69 is a flowchart showing one example of processing of I-Vg characteristics measurement. This flowchart is stored in the memory of computer 1120 as the control program and is executed by CPU.

In step S2010, a sample with known dilution ratio is dropped onto a predetermined position of biosensor body section 1110. This processing is performed manually by users or automatically by μ-TAS.

Then, in step 2020, determination is made whether or not the switch is turned ON. Switch ON manipulation is performed manually by users or automatically by μ-TAS.

When the switch is turned ON(S2020: YES), it is determined that the sample is dropped, and it proceeds to next step S2030.

In step S2030, source-drain voltage (Vsd) is set to a predetermined value (e.g., −1 V).

In step S2040, gate voltage (Vg) is set to the initial value (e.g., −10 V).

In step S2050, source-drain current (Isd: hereafter expressed simply as "I" in some cases) at source-drain voltage and gate voltage being set as mentioned are measured and stored (recorded) in the memory.

In step S2060, gate voltage is changed. Specifically, for example, value of gate voltage is renewed by adding 0.1 V to present gate voltage (Vg$_{n+1}$=Vg$_n$+0.1).

In step S2070, determination is made whether or not the processing should be terminated. Specifically, for example, determination is made whether or not gate voltage after renewal exceeds the predetermined range, in other words, as one example, when gate voltage is varied every 0.1 V in the range of −10 V and +10 V, determination is made if gate voltage after renewal is 10.1 V or more. As a result of this determination, when gate voltage after renewal exceeds the predetermined range (S2070: YES), it returns to the main flowchart shown in FIG. 68, thereby completing the flow. Meanwhile, when gate voltage after renewal does not exceed the predetermined range (S2070: NO), it returns to step S2050, and source-drain current at gate voltage after renewal is measured and recorded.

Next, Processing of inflection point determination (step S2100) will be explained.

FIG. 70 is a flowchart showing one example of processing procedure of inflection point determination. This flowchart is stored in the memory of computer 1120 as the control program and is executed by CPU.

First, in step S2110, derivative value (dI/dVg) is calculated every gate voltage (Vg) for the I-Vg characteristics acquired in step S2000.

Then, in step S2120, a maximum value is selected from derivative values calculated in step S2110.

Then, in step S2130, position corresponding to the maximum value selected in step S2120 is considered to be inflection point, current value (source-drain current) at this inflection point is stored (recorded) in the memory, then returns to the main flow shown in FIG. 68, thereby completing the flow.

Next, Processing of calibration curve determination (step S2300) will be explained.

FIG. 71 is a flowchart showing one example of processing procedures of calibration curve determination. This flowchart is stored in the memory of computer 1120 as the control program and is executed by CPU.

In step S2310, plotting to the graph is performed. That is, on the graph where abscissa represents dilution ratio and ordinate represents current value are plotted current values (source-drain current) of the inflection point corresponding to not less than three different dilution ratios acquired in step S2000 through step S2300.

In step S2320, mathematical relations are determined. In particular, for example, a straight line determined by least-square method is drawn in linear region on the graph based on results of plotting in step S2310. In other words, coefficients a and b in y=ax+b are determined. In this example, x represents dilution ratio and y represents current value (source-drain current) at the inflection point. This straight line (y=ax+b) is the calibration curve.

For example, in I-Vg characteristics (I-Vg characteristics when concentration of CaM antigen is changed) shown in FIG. 64, current value ($\times 10^{-6}$) at inflection point when dilution ratio (logarithm) shown by (a) is $-10$ is 2.7, current value ($\times 10^{-6}$) at inflection point when dilution ratio (logarithm) shown by (b) is $-9$ is 2.6, current value ($\times 10^{-6}$) at inflection point when dilution ratio (logarithm) shown by (c) is $-5$ is 2.4. Results thus obtained are plotted on the graph (see FIG. 72A) and a straight line determined by least-square method is drawn to obtain a calibration curve (see FIG. 72B).

To compensate for scattering of measurement results, average value may be used for current values at inflection point for each dilution ratio. To obtain the average value, processing is repeated several times for each dilution ratio and their average is calculated.

A calibration curve using linear range as dynamic range is determined as mentioned above, thereby completing the flow.

FIG. 73 is a flowchart showing one example of processing procedures of alteration of calibration function. In this example, processing procedures of I-Vg characteristics determination (step S2000) and inflection point determination (step S2100) are partly altered. In this example of alteration, as shown in FIG. 73, step S2140 and step S2150 are inserted to the flowchart shown in FIG. 69.

Step S2010 through step S2050 are identical with each step of the flowchart shown in FIG. 69, and therefore, their explanation will not be repeated. However, in this example of alteration, detailed numerical examples are used for explanation. That is, in step S2030, source-drain voltage (Vsd) is set to $-1$ V and in step S2040, gate voltage (Vg) is set to the initial value ($-10$ V).

In step S2140, derivative value (dI/dVg) of source-drain current (I) measured in step S2050 is obtained. Specifically, since increment of gate voltage (dVg) is constant (0.1 V), a difference (dI) between previous measurement and current measurement is obtained to calculate dI/dVg.

In step S2150, a maximum value is selected from derivative values (dI/dVg) calculated till now, and current value at the point corresponding to the maximum value (inflection point) is recorded in renewal fashion together with the maximum value thus selected. Here, selection of the maximum value is performed by, for example, comparison between present maximum value and derivative value calculated currently.

Step S2060 and step S2070 identical with each step of the flowchart shown in FIG. 69, and therefore, their explanation will not be repeated. However, in this example of alteration, detailed numerical examples are used for explanation. That is, in step S2060, gate voltage is renewed by adding 0.1 V to present gate voltage, and in step S2070, determination is made whether or not gate voltage after renewal is 10.1 V or more.

Next, measurement functions of biosensor device 1100 shown in FIG. 67 will be explained.

FIG. 74 is a flowchart showing one example of processing procedures of the measurement functions. This flowchart is stored in the memory of computer 1120 as the control program and is executed by CPU.

In step S3000, measurement of I-Vg characteristics is carried out for an unknown sample. Step S3000 is identical with step S2000 in the flowchart shown in FIG. 68, and therefore, explanation thereof will not be repeated.

In step S3100, inflection point of I-Vg characteristics acquired in step S3000 is determined and current value (source-drain current) at this inflection point is identified. Step S3100 is identical with step S2100 in the flowchart shown in FIG. 68, and therefore, explanation thereof will not be repeated.

Then, in step S3200, concentration of the unknown sample is determined using calibration curve prepared in advance. Specifically, dilution ratio x of the unknown sample is obtained by substituting current value y at the inflection point identified in step S3100 in the mathematical relation y=ax+b (coefficient a, b determined already) which shows calibration curve, and concentration is determined based on the dilution ratio thus obtained.

Meanwhile, when measurement is performed for another unknown sample, processing in step S3000 through step S3200 are simply repeated.

As mentioned above, presence or absence of a detection target substance in an unknown sample as well as concentration can be detected by the biosensor device according to the present invention.

When sample concentration does not fall in a dynamic range, for example, when concentration is too high and goes beyond the dynamic range, several diluted samples are prepared in advance, and concentration can be determined using the biosensor device for multiple analytes.

Further, computer 1120 can display data obtained (e.g., I-Vg characteristics, inflection point, calibration curve, presence or absence of sample, concentration, or the like) on the display section.

The present application is based on Japanese Patent Application No. 2005-174404 filed on Jun. 14, 2005, Japanese Patent Application No. 2005-174408 filed on Jun. 14, 2005, Japanese Patent Application No. 2005-237002 filed on Aug. 17, 2005, and Japanese Patent Application No. 2005-252506 filed on Aug. 31, 2005, the entire content of which is expressly incorporated by reference herein.

INDUSTRIAL APPLICABILITY

FET of the present invention has excellent electric characteristics. Therefore, by applying specifically to biosensors, biosensors exhibiting markedly more excellent detection sensitivity than conventional biosensors can be presented. Further, since the biosensor according to the present invention can be miniaturized, application to outdoor detection which could not be attained by conventional biosensors is possible.

The invention claimed is:
1. A biosensor device including a biosensor device body and an element section which is attachable to and detachable from the biosensor device body, wherein said element section includes a field effect transistor comprising:

a substrate having a first insulating film, a second insulating film and a support substrate composed of a semiconductor material or metal, the support substrate being sandwiched between said first insulating film and said second insulating film;

a source electrode and a drain electrode disposed on the first insulating film;

a channel electrically connecting said source electrode and said drain electrode, and including an ultra fine fiber, said channel being disposed on said first insulating film;

a gate electrode capable of causing a polarization due to a movement of free electrons in said substrate and capable of controlling an electric current flowing through said channel, said gate electrode being arranged on said second insulating film; and molecules immobilized on said second insulating film, said molecules capable of capturing a detection target substance being sandwiched between said second insulating film and said gate electrode, wherein when said element section is mounted to said biosensor device body, the electric current flows through said channel, and said gate electrode controls the electric current flowing through said channel.

2. A biosensor device including a biosensor device body and an element section which is attachable to and detachable from said biosensor device body, wherein said element section includes a field effect transistor comprising:

a substrate, having a support substrate composed of a semiconductor material or metal, and a first insulating film formed on a first plane of said support substrate;

a source electrode and a drain electrode disposed on said substrate;

a channel electrically connecting said source electrode and said drain electrode and including an ultra fine fiber;

a gate electrode capable of causing a polarization due to a movement of free electrons in said substrate and capable of controlling an electric current flowing through said channel; and molecules immobilized directly on said gate electrode and capable of capturing a detection target substance, wherein when said element section is mounted to said biosensor device body, the electric current flows through said channel, and said gate electrode controls the electric current flowing through said channel, said source electrode, said drain electrode, said channel and said gate electrode being arranged on a same surface of said first insulating film.

* * * * *